US009505810B2

(12) United States Patent
Prescott et al.

(10) Patent No.: US 9,505,810 B2
(45) Date of Patent: Nov. 29, 2016

(54) **TOXINS IN TYPE A *CLOSTRIDIUM PERFRINGENS***

(71) Applicant: University of Guelph, Guelph (CA)

(72) Inventors: John Prescott, Guelph (CA); Iman Mehdizadeh Gohari, Guelph (CA); Valeria Parreira Pinto, Guelph (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 14/832,647

(22) Filed: Aug. 21, 2015

(65) Prior Publication Data

US 2016/0052977 A1 Feb. 25, 2016

Related U.S. Application Data

(60) Provisional application No. 62/040,700, filed on Aug. 22, 2014.

(51) Int. Cl.

| | |
|---|---|
| ***A61K 39/08*** | (2006.01) |
| ***C07K 14/33*** | (2006.01) |
| ***C07K 14/245*** | (2006.01) |
| ***C07K 16/12*** | (2006.01) |
| ***G01N 33/569*** | (2006.01) |
| ***C12Q 1/68*** | (2006.01) |
| *A61K 39/00* | (2006.01) |

(52) U.S. Cl.

CPC ............... *C07K 14/33* (2013.01); *A61K 39/08* (2013.01); *C07K 16/1282* (2013.01); *C12Q 1/689* (2013.01); *G01N 33/56911* (2013.01); *A61K 39/00* (2013.01); *A61K 2039/552* (2013.01); *C07K 2317/33* (2013.01); *C07K 2317/76* (2013.01); *C07K 2319/00* (2013.01); *C12Q 2600/158* (2013.01); *G01N 2333/33* (2013.01); *G01N 2469/10* (2013.01)

(58) Field of Classification Search

CPC .................. A61K 2039/55; A61K 2039/552; A61K 39/0258; A61K 39/08; A61K 2039/521; A61K 2039/5252; A61K 2039/545; A61K 2039/70; A61K 39/12; A61K 39/15; A61K 35/20; C07K 14/44

See application file for complete search history.

(56) References Cited

U.S. PATENT DOCUMENTS

2015/0158917 A1 6/2015 Prescott et al.

FOREIGN PATENT DOCUMENTS

WO 2008148166 A1 12/2008
WO 2013173910 A1 11/2013

OTHER PUBLICATIONS

Davis et al. "New Fusion Protein Systems Designed to Give Soluble Expression in *Escherichia coli*", Biotechnology and Bioengineering, vol. 65, No. 4, Nov. 20, 1999, pp. 382-388.

Gohari, Iman Mehdizadeh et al. "A Novel Pore-Forming Toxin in Type A Clostridium perfringens Is Associated with Both Fatal Canine Hemorrhagic Gastroenteritis and Fatal Foal Necrotizing Enterocolitis", PLOS ONE, DOI: 10. 1371, Apr. 8, 2015, pp. 1-27.

Prescott, John et al. "A Novel Pore-Forming Toxin in Type A Clostridium perfringens is Associated with both Fatal Canine Hemorrhagic Gastroenteritis and Fatal Foal Necrotizing Enterocolitis", Abstract, The 3rd Prato Conference on the Pathogenesis of Bacterial Diseases of Animals, https://members.asnevents.com.au/event/1305/abstract/view/19896, Oct. 2014.

"A novel pore-forming toxin in Type A Clostridium perfringens is associated with fatal canine hemorrhagic gastroenteritis and fatal foal necrotizing enterocolitis", Powerpoint, The 3rd Prato Conference on the Pathogenesis of Bacterial Diseases of Animals, Oct. 9, 2014.

Keyburn, A. et al. "NetB, a New Toxin That is Associated with Avian Necrotic Enteritis Caused by Clostridium Perfringens. PLoS Pathogens", Feb. 2008, vol. 4, No. 2, pp. 0001-0011.

Database Genbank [Mar. 30, 2009], retreived on Jul. 9, 2013. Retrieved from NCBI (National Center for Biotechnology Information). Accession No. EU143239.

Database Genbank [Mar. 30, 2009], retreived on Jul. 10, 2013. Retrieved from NCBI (National Center for Biotechnology Information). Accession No. ABW71134.

Gohari, Iman Mehdizadeh, Clostridium Perfringens and its Potential Role in Equine Colitis. Guelph Ontario, Canada. Mar. 2012. Master of Science Thesis.

Gohari, Iman Mehdizadeh, Clostridium Perfringens and its Potential Role in Equine Colitis. Guelph Ontario, Canada. Apr. 19, 2012. Presentation of Master of Science Thesis.

Yan, Xu-Xia et al. Structural and Functional Analysis of the Pore-Forming Toxin NetB from Clostridium Perfringens. mBio, Jan./Feb. 2013, vol. 4, Issue 1, pp. 1-9.

Lepp, D. et al., "Identification of Novel Pathogenicity Loci in Clostridium perfringens Strains That Cause Avian Necrotic Enteritis", PLoS ONE, May 2010, vol. 5, No. 5, e10795, pp. 1-18.

Parreira, V.R. et al., "Sequence of Two Plasmids from Clostridium perfringens Chicken Necrotic Enteritis Isolates and Comparison with C. perfringens Conjugative Plasmids", PLoS ONE, Nov. 2012, vol. 7, No. 11, e49753, pp. 1-11.

Miyamoto, K. et al., "Complete Sequencing and Diversity Analysis of the Enterotoxin-Encoding Plasmids in Clostridium pergringens Type A Non-Food-Borne Human Gastrointestinal Disease Isolates", Journal of Bacteriology, Feb. 2006, vol. 188, No. 4, pp. 1585-1598.

Miyamoto, K. et al., "Sequencing and Diversity Analyses Reveal Extensive Similarities between Some Epsilon-Toxin-Encoding Plasmids and the pCPF5603 Clostridium perfringens Enterotoxin Plasmid", Journal of Bacteriology, Nov. 2008, vol. 190, No. 21, pp. 7178-7188.

*Primary Examiner* — Padma V Baskar
(74) *Attorney, Agent, or Firm* — Bereskin & Parr LLP; Melanie Szweras

(57) ABSTRACT

The present disclosure relates to novel pore-forming toxins of Type A *C. perfringens* and immunogenic compositions and vaccines thereof. The present disclosure further relates to methods and uses of treating or preventing enteric disease and assays for diagnosing enteric disease.

8 Claims, 9 Drawing Sheets

TOXINS IN TYPE A *CLOSTRIDIUM PERFRINGENS*

CROSS-REFERENCE TO RELATED APPLICATION

This application claims benefit under 35 U.S.C. §119(e) to U.S. Provisional Patent Application Ser. No. 62/040,700, filed Aug. 22, 2014, incorporated herein by reference in its entirety.

INCORPORATION OF SEQUENCE LISTING

A computer readable form of the Sequence Listing "6580-P46706US01_SequenceListing.txt" (69,632 bytes), submitted via EFS-WEB and created on Aug. 21, 2015, is herein incorporated by reference.

FIELD

The present disclosure relates to novel *Clostridium perfringens* toxins, nucleic acids, proteins and antibodies thereof as well as compositions, methods, uses and screening assays thereof.

BACKGROUND

*Clostridium perfringens* is an important Gram-positive anaerobic pathogen of humans and animals that is found ubiquitously in soil and the gastrointestinal tract of vertebrates. It causes a number of histotoxic and enterotoxemic diseases. The species produces an array of extracellular toxins, four of which (alpha, beta, epsilon and iota) form the basis for a toxin-typing scheme, which identifies five toxin types (types A, B, C, D or E) (Songer, 1996). In recent years, a novel toxin, NetB, was shown to be produced by the majority of type A isolates recovered from chickens with necrotic enteritis (NE), an important disease in broiler chicken production, and to play a critical role in NE pathogenesis (Keyburn et al., 2008). This advance raises the possibility that type A strains in a number of other poorly understood but clinically and pathologically distinct enteric diseases of different animal species (Songer, 1996) might contain other as-yet-undescribed necrotizing toxin genes (Nowell et al., 2012).

A number of important toxins, including CPB2 (beta2)-toxin, *C. perfringens* enterotoxin (CPE, in non-food-borne strains), and all the typing toxins except for alpha-toxin (CPA), are encoded on a conserved family of large plasmids related to the pCW3 tetracycline-resistance plasmid. These plasmids share a conserved core region that includes the transfer of clostridial plasmid (tcp) locus required for conjugation (Parreira et al., 2012; Li et al., 2013). The transmissible nature of key *C. perfringens* toxin and related virulence genes suggests that virulence of different toxin types can change through plasmid acquisition or loss. However, phylogenetic studies of *C. perfringens* disease strains also suggest a contribution of the chromosomal background to virulence that varies with the source of the strain. For example, clonality has been described for the majority of bovine type E isolates, for porcine type C isolates, and for isolates from chickens with NE (Jost et al., 2006; Hibberd et al., 2011; Xiao et al., 2012; Lepp et al., 2013).

*Clostridium perfringens* type A-associated diarrhea and enteric disease in dogs is not well characterized, but its association with disease may range in severity from mild and self-limiting to the fatal acute hemorrhagic diarrhea (Marks, 2012). The acute hemorrhagic gastroenteritis form of disease is marked by severe necrotizing inflammation of the intestinal tract, especially of the small intestine, by hemorrhage and in some cases by rapid death (Prescott et al., 1978; Sasaki et al., 1999). The presence of large numbers of *C. perfringens* adhering to the necrotic intestinal mucosa is a striking and common feature (Prescott et al., 1978; Sasaki et al., 1999; Schlegel et al., 2012; Unterer et al., 2014). Morbidity may be more common than mortality. Because the infection is not well characterized, no gold standard for diagnosis exists (Marks, 2012). In other species, a recognized predisposing factor for severe *C. perfringens* enteritis is colostrum- or food-associated trypsin-inhibition which prevents pancreatic trypsin proteolysis of secreted toxin (Songer, 1996), but such a possibility of food-associated infection in canine hemorrhagic gastroenteritis is purely speculative. Although not well characterized, acute haemorrhagic gastroenteritis associated with *C. perfringens* occurs particularly in small breed dogs (Burrows, 1977).

The role of type A *C. perfringens* in enteric diseases of horses is also not well understood. There is evidence that CPB2 toxin producing *C. perfringens* plays a role in the fatal progression of colitis in horses (Herholz et al., 1999; Bacciarini et al., 2003). Vilei and others (2005) demonstrated that some out-of-frame cpb2-positive equine disease isolates produced the CPB2 toxin when grown in sub-inhibitory concentrations of gentamicin. They proposed a feasible direct role of these isolates in antibiotic-associated diarrhea in horses, since treatment with aminoglycoside antibiotics allowed translation of the cpb2 mRNA through induction of a ribosomal frame-shift. Anecdotally, there was an association between the isolation of cpb2-positive *C. perfringens* from cases of equine colitis and the use of gentamicin in hospitalized diarrheic horses, which ended when the antibiotic was stopped (Vilei et al., 2005). The correlation between CPB2 with severe and sometimes fatal colitis in horses is intriguing but the association remains unproven (Waters et al., 2005). An apparent association has also been noted between the presence of the *C. perfringens* enterotoxin (CPE) and diarrheal illness in adult horses and in foals, including severe enteric disease (Kanoe et al., 1990; Netherwood et al., 1998; Donaldson and Palmer, 1999; Weese et al., 2001).

Type A *C. perfringens* with cbp2 and (rarely) cpe genes are commonly found in the feces of healthy foals, whereas type C is seldom found in healthy horses (Tillotson et al., 2002). Considerable work has been done on the important role of type C *C. perfringens* in neonatal enterocolitis (Traub-Dargatz and Jones, 1993; East et al., 1998). The role of type A in fatal enterocolitis is less clear, but necrosis of the small intestine and colon in 1-14-day-old foals caused by type A *C. perfringens* has been described in Kentucky (Donahue and Williams, 2002). These isolates possessed cpb2 and cpe (Timoney et al., 2005). Other sporadic case reports associate type A *C. perfringens* with fatal enterocolitis in neonatal foals (Diab et al., 2011; Hazlett et al., 2011).

WO2013/173910 reported isolation of a putative toxin from Type A *C. perfringens*, which was termed NetE and was considered as a likely contributor to necrotizing enteritis/haemorrhagic gastroenteritis in dogs and foals.

SUMMARY

The present inventors have isolated two further putative pore-forming toxins from *C. perfringens*, NetF and NetG, associated with fatal hemorrhagic gastroenteritis of dogs and fatal necrotizing enterocolitis of neonatal foals. The present inventors further showed that NetF by itself has toxicity.

Accordingly, the present disclosure provides an isolated nucleic acid molecule comprising a nucleic acid sequence as shown in SEQ ID NO:1 or SEQ ID NO:2 or variants thereof. Also provided herein is a recombinant expression vector comprising any of the isolated nucleic acid molecules disclosed herein.

In another embodiment, the present disclosure provides an isolated polypeptide encoded by the nucleic acid as shown in SEQ ID NO:1 or SEQ ID NO:2 or variants thereof. In yet another embodiment, the present disclosure provides an isolated polypeptide having the amino acid sequence as shown in SEQ ID NO:3 or SEQ ID NO:4 or variants thereof.

In one embodiment, the isolated polypeptide is toxoided.

In another embodiment, the disclosure provides a fusion protein comprising the isolated polypeptide disclosed herein fused to a solubility protein. In one embodiment, the solubility protein is NusA. In a particular embodiment, the fusion protein comprises the amino acid sequence as shown in SEQ ID NO:5 or SEQ ID NO:6 or variants thereof or is encoded by the nucleic acid sequence as shown in SEQ ID NO:7 or SEQ ID NO:8 or variants thereof.

Further provided is a host cell comprising any of the isolated nucleic acid molecules disclosed herein, any of the recombinant expression vectors disclosed herein, or any of the isolated polypeptides or fusion proteins disclosed herein.

In yet another embodiment, the disclosure provides a binding protein that binds any of the isolated polypeptides disclosed herein. In one embodiment, the binding protein is an antibody or antibody fragment. In an embodiment, the antibody is a monoclonal antibody.

Also provided herein is an immunogenic composition comprising any of the isolated polypeptides disclosed herein, any of the fusion proteins disclosed herein or any of the host cells disclosed herein; and a pharmaceutically acceptable carrier.

Further provided herein is an immunogenic composition comprising supernatant isolated from a NetF-positive *C. perfringens* strain or a NetG-positive *C. perfringens* strain. In an embodiment, the immunogenic composition comprises supernatant isolated from a NetF-positive, NetE-negative *C. perfringens* strain or a NetG-positive, NetE-negative *C. perfringens* strain. In one embodiment, the supernatant is concentrated. In another embodiment, the immunogenic composition comprising supernatant further comprises additional isolated NetF or NetG protein or NetF-solubility fusion protein or NetG-solubility fusion protein.

In one embodiment, the immunogenic composition further comprises an adjuvant.

In another embodiment, the immunogenic composition disclosed herein further comprises an additional *C. perfringens* toxin protein, optionally Cpe, Cpa, NetB, Cpb2, NetE or TpeL. In one embodiment, the additional *C. perfringens* toxin protein is Cpe. In another embodiment, the additional *C. perfringens* toxin protein is NetE. In yet another embodiment, the additional *C. perfringens* toxin protein is NetF (if the immunogenic composition already comprises NetG) or NetG (if the immunogenic composition already comprises NetF).

Also provided herein is a composition comprising plasma from a horse vaccinated with an isolated polypeptide disclosed herein. In an embodiment, the plasma is collected, concentrated or fractionated from the blood.

Also provided herein are methods and uses of any of the immunogenic compositions and binding proteins disclosed herein. In one embodiment, the present disclosure provides a method of treating or preventing Type A *C. perfringens* enteric disease comprising administering an immunogenic composition or binding protein disclosed herein to a subject in need thereof. Also provided herein is a use of an immunogenic composition or binding protein disclosed herein for treating or preventing Type A *C. perfringens* enteric disease in a subject in need thereof. Further provided is an immunogenic composition or binding protein disclosed herein for use in treating or preventing Type A *C. perfringens* enteric disease in a subject in need thereof. Even further provided is use of an immunogenic composition or binding protein disclosed herein in the preparation of a medicament for treating or preventing Type A *C. perfringens* enteric disease in a subject in need thereof.

In one embodiment, the subject is a mammal or bird. In a particular embodiment, the subject is a horse, dog or human. In another embodiment, the enteric disease is haemorrhagic or necrotizing gastroenteritis. In yet another embodiment, the enteric disease is haemorrhagic or necrotizing small intestinal enteritis. In a further embodiment, the enteric disease is typhlocolitis.

Even further provided is a method of making hyperimmune plasma comprising vaccinating a horse with an isolated polypeptide disclosed herein; isolating blood from the horse; collecting, fractionating or concentrating the blood to obtain the hyperimmune plasma.

Further provided herein is a method of monitoring or diagnosing enteric disease in a subject, comprising the steps of:

a) detecting the presence of NetF and/or NetG of *Clostridium perfringens* in a sample from the subject; and b) comparing the expression of the NetF and/or NetG from the sample with a control;

wherein a difference in expression of NetF and/or NetG in the sample from the subject as compared to the control is indicative of enteric disease in the subject.

In one embodiment, the NetF and/or NetG comprises any of the polypeptides disclosed herein or is encoded by any of the nucleic acid molecules disclosed herein.

In an embodiment, the NetF or NetG is detected in step (a) by detecting a nucleic acid molecule encoding the toxin in the sample by hybridization using a probe specific for the toxin or by PCR using primers specific for the toxin, such as the primers as shown in SEQ ID NOs:9, 10, 11 or 12.

In another embodiment, the NetF or NetG is detected in step (a) by detecting a NetF or NetG polypeptide using an antibody that specifically binds the NetF or NetG. In one embodiment, the antibody is a monoclonal antibody.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Figure 1:
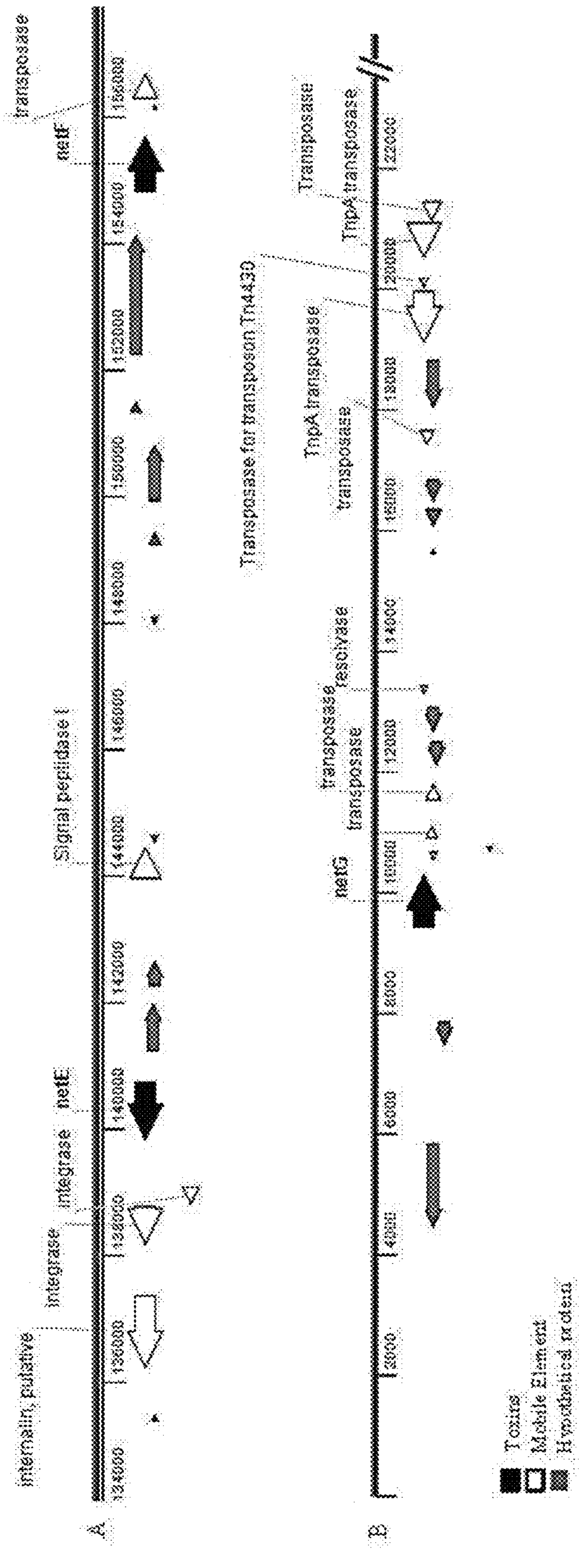
FIG. 1 shows the genetic organization of JP718 scaffolds. The genetic organization of (A) partial view of scaffold00006, (B) partial view of scaffold00012 is shown, each arrow representing a predicted gene and its orientation. Predicted functional annotations and respective positions are shown above each gene, respectively. Genes are shaded in line with their putative role based upon sequence analyses.
Figure 1:
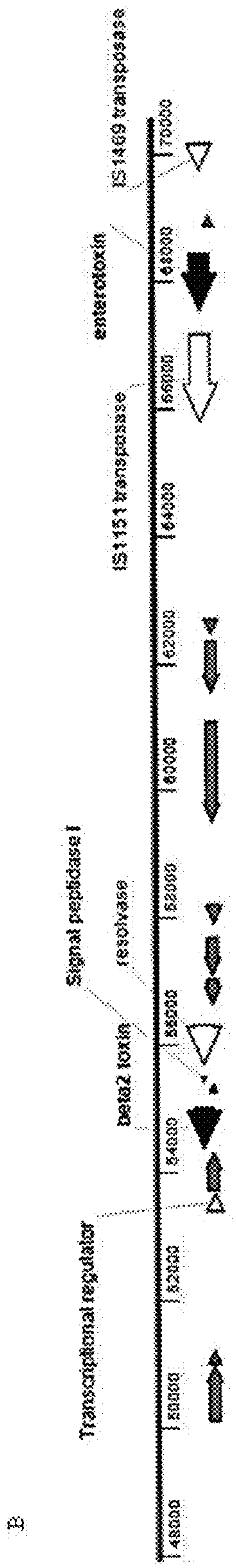

NetF and NetG (Toxin F and G) Nucleic Acids and Proteins

The present inventors have demonstrated that the novel *C. perfringens* toxin NetF as well as supernatants that are NetF positive have cytotoxicity.

Accordingly, the present disclosure provides an isolated nucleic acid molecule comprising a nucleic acid sequence as shown in SEQ ID NO:1 or a variant thereof. In one embodiment, the nucleic acid molecule comprises, consists essentially of or consists of the nucleic acid sequence as shown in SEQ ID NO:1.

The present inventors have also isolated an additional *C. perfringens* putative toxin NetG. Although NetG was not found to be cytotoxic against the cell lines tested herein, it is predicted to be a pore-forming toxin based on sequence homology and, without wishing to be bound by theory, is likely to be toxic in a different chromosomal background or may aid in regulation of other toxin proteins, such as NetF.

Accordingly, the disclosure also provides an isolated nucleic acid molecule comprising a nucleic acid sequence as shown in SEQ ID NO:2 or a variant thereof. In one embodiment, the nucleic acid molecule comprises, consists essentially of or consists of the nucleic acid sequence as shown in SEQ ID NO:2.

The term "isolated" refers to a nucleic acid substantially free of cellular material or culture medium when produced by recombinant DNA techniques, or chemical precursors, or other chemicals when chemically synthesized.

The term "nucleic acid molecule" is intended to include unmodified DNA or RNA or modified DNA or RNA. For example, the nucleic acid molecules or polynucleotides of the disclosure can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

The term "toxF or toxin F" or "NetF" are synonymous and are used herein to refer to one of the novel genes or proteins disclosed herein isolated from Type A *Clostridium perfringens*. Similarly the term "toxG or toxin G" or "NetG" are synonymous and are used herein to refer to the other of the novel genes or proteins disclosed herein isolated from Type A *Clostridium perfringens*.

Variant nucleic acid sequences include nucleic acid sequences that hybridize to the nucleic acid sequence as shown in SEQ ID NO: 1 (or 7 disclosed herein) or SEQ ID NO:2 (or 8 disclosed herein) under at least moderately stringent hybridization conditions, or have at least 78%, at least 80%, at least 85%, at least 90%, at least 95%, or at least 98% sequence identity to the nucleic acid sequence of SEQ ID NO:1 or 2 (or 7 or 8).

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41 (% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In some embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N. Y., 2002, and in: Sambrook et al., Molecular Cloning: a Laboratory Manual, Cold Spring Harbor Laboratory Press, 2001.

Variant nucleic acid sequences or molecules also include analogs of the nucleic acid sequences and molecules described herein. The term "a nucleic acid sequence which is an analog" means a nucleic acid sequence which has been modified as compared to the sequences described herein, wherein the modification does not alter the utility of the sequences described herein. The modified sequence or analog may have improved properties over the sequence shown in SEQ ID NOs:1, 2, 7 or 8. One example of a modification to prepare an analog is to replace one of the naturally occurring bases (i.e. adenine, guanine, cytosine or thymidine) of the sequence with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequences.

The variant nucleic acid sequences further include conservatively substituted nucleic acid sequences. In the context of this specification, the term "conserved" describes similarity between sequences. The degree of conservation between two sequences can be determined by optimally aligning the sequences for comparison. Sequences may be aligned using the Omiga software program, Version 1.13. (Oxford Molecular Group, Inc., Campbell, Calif.). The Omiga software uses the Clustal W Alignment algorithms [Higgins, D. G. and Sharp, P. M. (1989). Fast and sensitive multiple sequence alignments on a microcomputer. CABIOS 5, 151-153; Higgins, D. G., Bleasby, A. J., and Fuchs, R. (1991). CLUSTAL V: improved software for multiple sequence alignment. CABIOS 8, 189-191; Thompson, J. D., Higgins, D. G., and Gibson, T. J. (1994). CLUSTAL W: improving the sensitivity of progressive multiple sequence alignment through sequence weighting, positions-specific gap penalties and weight matrix choice. Nucleic Acids Research 22, 4673-4680]. Default settings used are as follows: Open gap penalty 10.00; Extend gap penalty 0.05; Delay divergent sequence 40 and Scoring matrix—Gonnet Series. Percent identity or homology between two sequences is determined by comparing a position in the first sequence with a corresponding position in the second sequence. When the compared positions are occupied by the same nucleotide or amino acid, as the case may be, the two sequences are conserved at that position. The degree of conservation between two sequences is often expressed, as it is here, as a percentage representing the ratio of the number of matching positions in the two sequences to the total number of positions compared.

Further, it will be appreciated that variants include nucleic acid molecules comprising nucleic acid sequences having substantial sequence homology or identity with the nucleic acid sequence as shown in SEQ ID NO:1, 2, 7 or 8. The term "sequences having substantial sequence homology or identity" means those nucleic acid sequences that have slight or inconsequential sequence variations from these sequences, i.e., the sequences function in substantially the same manner to produce functionally equivalent proteins.

Nucleic acid sequences having substantial homology include nucleic acid sequences having at least about 78, at least about 80 or at least about 85 percent identity with a nucleic acid sequence of SEQ ID NO:1, 2, 7 or 8. The level of homology, according to various aspects of the disclosure is at least about 90 percent; at least about 95 percent; or at least about 98 percent. Methods for aligning the sequences to be compared and determining the level of homology between the sequences are described in detail above. In an embodiment, the NetF variants encode proteins that are not altered at position 204, 270 and/or 275, i.e. the amino acid at position 204 of a variant NetF is a tyrosine residue and the amino acids at positions 270 and 275 of a variant NetF are tryptophan residues. In an embodiment, the NetG variants encode proteins that are not altered at position 205, 271 and/or 276, i.e. the amino acid at position 205 of a variant NetG is a tyrosine residue and the amino acids at positions 271 and 276 of a variant NetG are tryptophan residues.

Sequence identity can be calculated according to methods known in the art. Sequence identity is most preferably assessed by the algorithm of BLAST version 2.1 advanced search. BLAST is a series of programs that are available online at http://www.ncbi.nlm.nih.gov/BLAST. The advanced blast search (http://www.ncbi.nlm.nih.gov/blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656.

Variants further include nucleic acid sequences which differ from the nucleic acid sequence shown in SEQ ID NO:1, 2, 7 or 8 due to degeneracy in the genetic code. Such nucleic acids encode functionally equivalent proteins but differ in sequence from the above mentioned sequences due to degeneracy in the genetic code.

An isolated nucleic acid molecule of the disclosure which comprises DNA can be isolated by preparing a labelled nucleic acid probe based on all or part of the nucleic acid sequences as shown in SEQ ID NO:1, 2, 7 or 8 and using this labelled nucleic acid probe to screen an appropriate DNA library (e.g. a cDNA or genomic DNA library).

An isolated nucleic acid molecule of the disclosure which is DNA can also be isolated by selectively amplifying the nucleic acid using the polymerase chain reaction (PCR) methods and cDNA or genomic DNA. It is possible to design synthetic oligonucleotide primers from the nucleic acid sequence as shown in SEQ ID NO:1 or 2 (or 7 or 8) for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294 5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the disclosure which is RNA can be isolated by cloning the cDNA into an appropriate vector which allows for transcription of the cDNA to produce an RNA molecule which encodes NetF or a variant thereof or NetG or a variant thereof. For example, a cDNA can be cloned downstream of a bacteriophage promoter, (e.g., a T7 promoter) in a vector, cDNA can be transcribed in vitro with T7 polymerase, and the resultant RNA can be isolated by standard techniques.

A nucleic acid molecule of the disclosure may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

In another embodiment, the present disclosure provides an isolated polypeptide encoded by the nucleic acid as shown in SEQ ID NO:1 or a variant thereof or an isolated polypeptide having the sequence as shown in SEQ ID NO:3 or a variant thereof.

In one embodiment, the isolated polypeptide comprises, consists essentially of or consists of SEQ ID NO:3.

In yet another embodiment, the present disclosure provides an isolated polypeptide encoded by the nucleic acid as shown in SEQ ID NO:2 or a variant thereof or an isolated polypeptide having the sequence as shown in SEQ ID NO:4 or a variant thereof.

In one embodiment, the isolated polypeptide comprises, consists essentially of or consists of SEQ ID NO:4.

The term "isolated polypeptide" refers to a polypeptide substantially free of cellular material or culture medium when produced by recombinant DNA techniques, or chemical precursors or other chemicals when chemically synthesized.

In one embodiment, the isolated polypeptide is toxoided.

The term "toxoided" refers to inactivating the toxicity of the polypeptide. In one embodiment, the isolated polypeptide is a toxoided NetF protein. In another embodiment, the isolated polypeptide is a toxoided NetG protein. Approaches to toxoiding are known in the art and include, without limitation, inactivation with formalin in the procedure outlined by Ito, A. 1968. Alpha-toxoid of *Clostridium perfringens*. I. Purification and toxoiding of alpha-toxin of *C. perfringens*. Jpn. J. Med. Sci. Biol. 21:379-391. An alternative approach is a genetic approach to toxoiding similar to that described by Yan X-X, Porter C C, Hardy S, Steer D, Smith I A, et al. Structural and functional analysis of the pore-forming toxin NetB from *Clostridium perfringens*. mBio 2013; 4: 1-9. This approach involves using either cytotoxicity or hemolysis as a screen, and then using site directed mutagenesis of NetF or NetG to remove the cytotoxic activity of the toxin while retaining its immunogenicity. The formalin inactivation involves progressive treatment of the NetF/NetG or rNetF-NusA/rNetG-NusA protein to remove toxicity.

Even further included herein is a fusion protein comprising the NetF and/or NetG protein disclosed herein fused with a solubilizing partner (also sometimes termed solubility partner). In one embodiment, the solubilizing partner is bacterioferritin (BFR) or heat shock protein (GrpE). In another embodiment, the solubilizing partner is NusA. In one embodiment, the NusA-NetF fusion protein comprises the amino acid sequence as shown in SEQ ID NO:5 or a variant thereof. In another embodiment, the NusA-NetG fusion protein is encoded by the nucleic acid sequence as shown in SEQ ID NO:6 or a variant thereof. In a particular embodiment, the fusion protein comprises, consists essentially of or consists of the amino acid sequence as shown in SEQ ID NO:5 or the amino acid sequence as shown in SEQ ID NO:6.

The term "NusA" as used herein refers to the NusA protein from any species or source. In one embodiment, the NusA protein is from *E. coli* and has the GenBank accession number: AAC76203.1 GI:1789560.

A person skilled in the art will appreciate that the disclosure includes variants to the amino acid sequences disclosed herein, including chemical equivalents. Such equivalents include proteins that perform substantially the same function in substantially the same way. For example, equivalents include, without limitation, conservative amino acid substitutions, deletions and insertions.

A “conservative amino acid substitution” as used herein, is one in which one amino acid residue is replaced with another amino acid residue without abolishing the protein's desired properties.

Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course, it would also be expected that the greater the percentage of homology, i.e., sequence similarity, of a variant protein with a naturally occurring protein, the greater the retention of its activity. Of course, as protein variants having the activity of NetF or NetG as described herein are intended to be within the scope of this disclosure, so are nucleic acids encoding such variants.

In one embodiment, the variant amino acid sequences have at least 65%, at least 70%, at least 75%, at least 80%, at least 85%, at least 90% or at least 95% identity to the amino acid sequence as shown in SEQ ID NO:3 or 4 or to the amino acid sequence encoded by the nucleic acid sequence as shown in SEQ ID NO:1 or 2. In an embodiment, the NetF variants are not altered at position 204, 270 and/or 275, i.e. the amino acid at position 204 of a variant NetF is a tyrosine residue and the amino acids at positions 270 and 275 of a variant NetF are tryptophan residues. In an embodiment, the NetG variants are not altered at position 205, 271 and/or 276, i.e. the amino acid at position 205 of a variant NetG is a tyrosine residue and the amino acids at positions 271 and 276 of a variant NetG are tryptophan residues.

The term “sequence identity” as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

Variants of the NetF or NetG gene or protein or fusion protein disclosed herein may be prepared by introducing mutations in the nucleotide sequence encoding the protein. Mutations in nucleotide sequences constructed for expression of analogs of a protein of the disclosure must preserve the reading frame of the coding sequences. Furthermore, the mutations will optionally not create complementary regions that could hybridize to produce secondary mRNA structures, such as loops or hairpins, which could adversely affect translation of the mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins described above (including truncations, analogs, etc.) may be prepared using recombinant DNA methods. These proteins may be purified and/or isolated to various degrees using techniques known in the art. Accordingly, nucleic acid molecules of the present disclosure having a sequence which encodes a protein of the disclosure may be incorporated according to procedures known in the art into an appropriate expression vector which ensures good expression of the protein. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the disclosure and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic acid.

The disclosure therefore contemplates a recombinant expression vector of the disclosure containing a nucleic acid molecule of the disclosure, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The recombinant expression vectors of the disclosure may also contain a selectable marker gene that facilitates the selection of host cells transformed or transfected with a recombinant molecule of the disclosure. Examples of selectable marker genes are genes encoding a protein which confers resistance to certain drugs, such as G418 and hygromycin. Examples of other markers which can be used are: green fluorescent protein (GFP), β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the disclosure and in particular to determine the effect of a mutation on expression and phenotype. It will be appreciated that selectable markers can be introduced on a separate vector from the nucleic acid of interest.

The recombinant expression or cloning vectors of the disclosure may also contain genes which encode a fusion moiety which provides increased expression of the recombinant protein; increased solubility of the recombinant protein, such as NusA described herein; and aid in the purification of a target recombinant protein by acting as a ligand in affinity purification, such as a His-tag. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformed host cell" is intended to include prokaryotic and eukaryotic cells which have been transformed or transfected with a recombinant expression vector of the disclosure. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium chloride mediated transformation. Nucleic acid can be introduced into mammalian cells via conventional techniques such as calcium phosphate or calcium chloride co precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Accordingly, further provided is a host cell comprising any of the isolated nucleic acid molecules disclosed herein, any of the recombinant expression vectors disclosed herein, or any of the isolated polypeptides or fusion proteins disclosed herein.

Suitable host cells include a wide variety of prokaryotic and eukaryotic host cells. For example, the proteins of the disclosure may be expressed in bacterial cells such as *E. coli*, insect cells (using baculovirus), yeast cells or mammalian cells, COS1 cells. Other suitable host cells can be found in Goeddel, Gene Expression Technology: Methods in Enzymology 185, Academic Press, San Diego, Calif. (1991).

The disclosure includes a microbial cell that contains and is capable of expressing a heterologous nucleic acid molecule having a nucleotide sequence as encompassed by the disclosure. The heterologous nucleic acid molecule can be DNA.

The disclosure also contemplates a process for producing a NetF or NetG toxin protein as defined by the disclosure. The process includes such steps as:

preparing a DNA fragment including a nucleotide sequence which encodes said protein;

incorporating the DNA fragment into an expression vector to obtain a recombinant DNA molecule which includes the DNA fragment and is capable of undergoing replication;

transforming a host cell with said recombinant DNA molecule to produce a transformant which can express said protein;

culturing the transformant to produce said protein; and recovering said protein from resulting cultured mixture.

More particularly, the disclosure provides a method of preparing a purified protein of the disclosure comprising introducing into a host cell a recombinant nucleic acid encoding the protein, allowing the protein to be expressed in the host cell and isolating and purifying the protein. Optionally, the recombinant nucleic acid is a recombinant expression vector. Proteins can be isolated from a host cell expressing the protein and purified according to standard procedures of the art, including ammonium sulfate precipitation, column chromatography (e.g. ion exchange, gel filtration, affinity chromatography, etc.), electrophoresis, and ultimately, crystallization [see generally, "Enzyme Purification and Related Techniques", *Methods in Enzymology,* 22, 233-577 (1971)].

Alternatively, the protein or parts thereof can be prepared by chemical synthesis using techniques well known in the chemistry of proteins such as solid phase synthesis [Merrifield, J. Am. Chem. Assoc. 85:2149-2154 (1964); Frische et al., J. Pept. Sci. 2(4): 212-22 (1996)] or synthesis in homogeneous solution [Houbenweyl, Methods of Organic Chemistry, ed. E. Wansch, Vol. 15 I and II, Thieme, Stuttgart (1987)].

In yet another embodiment, the disclosure provides a binding protein that binds any of the isolated polypeptides disclosed herein.

The term "binding protein" as used herein refers to a protein that specifically binds to another substance. In an embodiment, the binding proteins are antibodies or antibody fragments thereof. In a further embodiment, the binding proteins are monoclonal antibodies or fragments thereof. In one embodiment, the binding protein is an antibody or antibody fragment that binds to a protein having the amino acid sequence of SEQ ID NO:3 or SEQ ID NO:4 or variants thereof or to a protein encoded by the nucleic acid sequence as shown in SEQ ID NO:1 or SEQ ID NO:2 or variants thereof.

The present inventors have shown that polyclonal antibodies raised to NetF recognized rNetF over 3× more specifically than binding to rNetE or rNetG. Furthermore, the neutralizing titres for polyclonal antibodies raised to NetF were about 5 to 10-fold greater when the antigen was rNetF compared to rNetE and rNetG (see Table 6). Accordingly, in an embodiment, the binding protein that binds specifically to NetF does not bind to other Net proteins or binds with at least 3×, at least 4×, at least 5×, at least 6×, at least 7×, or at least 8× higher affinity compared to binding to other Net proteins. In an embodiment, the binding protein that binds specifically to NetG does not bind to other Net proteins or binds with at least with at least 3×, at least 4×, at least 5×, at least 6×, at least 7×, or at least 8× higher affinity compared to other Net proteins.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', $F(ab')_2$, scFv, dsFv, ds-scFv, dimers, minibodies, diabodies, and multimers thereof and bispecific antibody fragments. Antibodies can be fragmented using conventional techniques. For example, $F(ab')_2$ fragments can be generated by treating the antibody with pepsin. The resulting $F(ab')_2$ fragment can be treated to reduce disulfide bridges to produce Fab' fragments. Papain digestion can lead to the formation of Fab fragments. Fab, Fab' and $F(ab')_2$, scFv, dsFv, ds-scFv, dimers, minibodies, diabodies, bispecific antibody fragments and other fragments can also be synthesized by recombinant techniques.

Conventional methods can be used to prepare the antibodies. For example, by using a peptide of a protein of the disclosure, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)); the EBV-hybridoma technique to produce human monoclonal antibodies (Cole et al. Monoclonal Antibodies in Cancer Therapy (1985) Allen R. Bliss, Inc., pages 77-96); and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the disclosure also contemplates hybridoma cells secreting monoclonal antibodies with specificity for a protein of the disclosure.

Chimeric antibody derivatives, i.e., antibody molecules that combine a non-human animal variable region and a human constant region are also contemplated within the scope of the disclosure. Chimeric antibody molecules can include, for example, the antigen binding domain from an antibody of a mouse, rat, or other species, with human constant regions. Conventional methods may be used to make chimeric antibodies containing the immunoglobulin variable region which recognizes a NetF or NetG protein of the disclosure (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the disclosure as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982); and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments reactive against a protein of the disclosure may also be generated by screening expression libraries encoding immunoglobulin genes, or portions thereof, expressed in bacteria with peptides produced from nucleic acid molecules of the present disclosure. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)).

The disclosure also contemplates the use of "peptide mimetics" for the binding proteins. Peptide mimetics are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of the binding proteins of the disclosure. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to the binding proteins of the disclosure.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Compositions, Methods and Uses

Further provided herein is a composition comprising a binding protein disclosed herein; and a pharmaceutically acceptable carrier.

Also provided herein is an immunogenic composition comprising any of the isolated polypeptides or fusion proteins disclosed herein or any of the host cells disclosed herein; and a pharmaceutically acceptable carrier.

Even further provided is an immunogenic composition comprising supernatant isolated from a NetF-positive *C. perfringens* strain or a NetG-positive *C. perfringens* strain or combinations thereof. In an embodiment, the supernatant is isolated from a NetF-positive, NetE-negative strain or a NetG-positive, NetE-negative strain. Even further provided is an immunogenic composition that further comprises additional NetF, NetG or other *C. perfringens* toxin proteins as disclosed herein.

A person skilled in the art would readily be able to determine whether a particular strain for example, from a case of canine haemorrhagic gastroenteritis or of equine severe necrotizing enteritis, particularly in foals, is NetF-positive or NetG-positive, for example, by using PCR primers to amplify the NetF or NetG nucleic acid sequence or using antibodies that specifically recognize the NetF or NetG protein. Methods for testing for NetF and NetG are disclosed herein.

Methods for preparing *C. perfringens* supernatants from NetF- or NetG-positive strains isolated from canine haemorrhagic gastroenteritis or equine severe necrotizing enteritis, particularly of foals, are known in the art and include the method described in the Examples section.

In one embodiment, the immunogenic composition comprises a concentrated supernatant from a NetF-positive *C. perfringens* strain. In another embodiment, the concentrated supernatant is from a NetF-positive, NetE-negative strain. In another embodiment, the immunogenic composition comprises a concentrated supernatant from a NetG-positive *C. perfringens* strain. In yet another embodiment, the concentrated supernatant is from a NetG-positive, NetE-negative strain.

The term "concentrated" as used herein refers to increasing the percentage of proteins relative to broth in the supernatant and includes a supernatant that has been concentrated at least 5 times, 10 times, 20 times, 30 times, 50 times, 100 times or more compared to a supernatant without concentration.

The term "immunogenic composition" as used herein refers to a composition that is able to elicit an immune response, including without limitation, production of antibodies or cell mediated immune responses, against an antigen present in the composition.

In one embodiment, the immunogenic composition is a vaccine. The term "vaccine" as used herein refers to an immunogenic composition that is capable of eliciting a prophylactic and/or therapeutic response that prevents, cures or ameliorates disease.

In one embodiment, the immunogenic composition comprises a NetF toxin protein disclosed herein and a NusA-NetF fusion protein disclosed herein, and a pharmaceutically acceptable carrier. In another embodiment, the immunogenic composition comprises a NetG toxin protein disclosed herein and a NusA-NetG fusion protein disclosed herein, and a pharmaceutically acceptable carrier.

In a further embodiment, the immunogenic composition further comprises an antibiotic or anti-diarrheal medication.

In an alternate embodiment, there is provided a composition comprising plasma obtained from a horse vaccinated with NetF or Net G. In an embodiment, the plasma is concentrated, for example, by isolation and filtering of blood to create plasma with elevated concentration of antibodies. In another embodiment, the plasma is collected plasma. In a further embodiment, the plasma is fractionated.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylarnino ethanol, histidine, procaine, etc.

In one embodiment, the immunogenic composition further comprises an adjuvant. The term "adjuvant" as used herein refers to a substance that is able to enhance the immunostimulatory effects of the antigen described herein but does not have any specific antigenic effect itself. Typical adjuvants include, without limitation, Freund's complete or incomplete adjuvant, aluminium salts, squalene, oil-based adjuvants, selected toll-like receptor ligands, Ribi's adjuvant, ISCOMs, Keyhole Limpet Hemocyanin (KLH) and others.

In another embodiment, the immunogenic compositions disclosed herein further comprise an additional *C. perfringens* toxin protein. In one embodiment, the additional *C. perfringens* toxin protein is *Clostridium perfringens* enterotoxin (Cpe), *Clostridium perfringens* alpha toxin (Cpa), necrotic enteritis toxin B-like (NetB), necrotic enteritis toxin E (NetE), beta2 toxin (Cpb2) or Toxin of *Clostridium perfringens* Large (TpeL).

The Cpe, Cpa, NetB, NetE, Cpb2 or TpeL can be from any species or source. For example, NetB can be that described in GenBank EU143239, GI:158524053; Cpe can be that described in GenBank M98037.1, GI:144927; Cpb2 can be that described in GenBank AY609161.1, GI:51949825; TpeL can be that described in GenBank EU848493, GI:194338410 and Cpa can be that described in GenBank X17300.1, GI:40619; NetE can be that shown in SEQ ID NO:47.

In one embodiment, the additional *C. perfringens* toxin protein is NetG, if the first *C. perfringens* toxin protein is NetF. In another embodiment, the additional *C. perfringens* toxin protein is NetF, if the first *C. perfringens* toxin protein is NetG.

Also provided herein are methods and uses of any of the immunogenic compositions or binding proteins disclosed herein. In one embodiment, the present disclosure provides a method of treating or preventing Type A *Clostridium perfringens* enteric disease comprising administering an immunogenic composition or binding protein disclosed herein to a subject in need thereof. Also provided herein is a use of an immunogenic composition or binding protein disclosed herein for treating or preventing Type A *Clostridium perfringens* enteric disease in a subject in need thereof. Further provided is an immunogenic composition or binding protein disclosed herein for use in treating or preventing Type A *Clostridium perfringens* enteric disease in a subject in need thereof. Even further provided is use of an immunogenic composition or binding protein disclosed herein in the preparation of a medicament for treating or preventing Type A *Clostridium perfringens* enteric disease in a subject in need thereof.

The "subject in need thereof" as used herein refers to a subject that is at risk of infection or is infected with Type A *Clostridium perfringens* and that has a chromosomal background or is otherwise susceptible to the NetF and/or NetG toxin.

"Type A *Clostridium perfringens* enteric disease" as used herein refers to a disease of the intestine caused by type A *Clostridium perfringens* infection and includes, without limitation, a serious *Clostridium perfringens* toxin-induced inflammation of the intestine associated with death (necrosis) of intestinal mucosal lining cells, and in cells underneath the mucosa, with inflammation in these structures sometimes marked by haemorrhage, and with serious impairment of intestinal function that may lead to death.

Accordingly, in another embodiment, the enteric disease is haemorrhagic or necrotizing gastroenteritis. In yet another embodiment, the enteric disease is haemorrhagic or necrotizing small intestinal enteritis. In a further embodiment, the enteric disease is typhlocolitis.

The term "administering a protein" includes both the administration of the protein as well as the administration of a nucleic acid sequence encoding the protein to an animal or to a cell in vitro or in vivo. The term "administering" also includes the administration of a cell that expresses the protein.

The term "treating" or "treatment" as used herein means administering to a subject a therapeutically effective amount of the compositions of the present disclosure and may consist of a single administration, or alternatively comprise a series of applications.

As used herein, and as well understood in the art, "treatment" or "treating" is also an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, spread of disease, delay or slowing of disease progression, amelioration or palliation of the disease state, and remission (whether partial or total), whether detectable or undetectable. "Treatment" can also mean prolonging survival as compared to expected survival if not receiving treatment. Further any of the treatment methods or uses described herein can be formulated alone or for contemporaneous administration with other agents or therapies. "Treatment" or "treating" can also include preventing the onset of disease.

The term "subject" or "animal" as used herein includes all members of the animal kingdom including birds and mammals, such as humans (patients), horses, lambs, dogs, black-footed ferrets, mice, minks, muskrats, camels, birds and rabbits. In one embodiment, the subject is a mammal such as a horse, lamb, dog, or human.

The term "subject in need thereof" as used herein refers to a subject or animal as defined above that is susceptible to or shown to be colonized by NetF or NetG positive *C. perfringens* bacteria.

NetF has been shown herein to be cytotoxic to horses and dogs and NetG has been isolated from horses and dogs infected with Type A *C. perfringens*. Accordingly, in a particular embodiment, the subject is a horse. In another particular embodiment, the subject is a dog.

As discussed herein, without wishing to be bound by theory, the chromosomal background of the subject may determine whether a particular pore-forming toxin has cytotoxicity. It is known that NetB, another related toxin, has cytotoxicity in chickens and, as shown herein, NetF has cytotoxicity in horses and dogs. Although the type of subject to which NetE and NetG are possibly toxic is not yet identified, a person skilled in the art can test if the NetF or NetG pore-forming toxin has cytotoxicity in a particular subject using the methods disclosed herein.

In accordance with the methods disclosed herein, the compositions disclosed herein may be administered to a patient in a variety of forms depending on the selected route of administration, as will be understood by those skilled in the art. For example, the compositions may be administered by oral or parenteral administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration.

The current treatment for enteric disease is almost exclusively antibiotics but it could include anti-diarrheal medications. Accordingly, in another embodiment, the methods and uses include co-administration with antibiotics or anti-diarrheal medications.

The term "co-administering" as used herein means that the immunogenic compositions and the current treatment are administered contemporaneously. The term "contemporaneous administration" of two substances to an individual means providing each of the two substances so that they are both biologically active in the individual at the same time. The exact details of the administration will depend on the pharmacokinetics of the two substances in the presence of each other. In one embodiment, the immunogenic composition is administered prior to the current treatment. In another embodiment, the immunogenic composition is administered at the same time as the current treatment. In yet another embodiment, the immunogenic composition is administered after the current treatment.

The dosage of the compositions disclosed herein can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compositions may be administered initially in a suitable dosage that may be adjusted as required, depending on the clinical response.

Even further provided is a method of making hyperimmune plasma comprising vaccinating a horse with an isolated polypeptide disclosed herein; isolating blood from the horse; collecting, fractionating or concentrating the blood to obtain the hyperimmune plasma. A person skilled in the art would readily know the appropriate timing of vaccination(s) and would follow techniques known in the art to isolate and concentrate plasma from blood.

Diagnostic Methods

Further provided herein is a method of monitoring or diagnosing enteric disease in a subject, comprising the steps of:

a) detecting the presence of NetF or NetG toxin of *Clostridium perfringens* in a sample from the subject; and b) comparing the expression of the NetF or NetG toxin from the sample with a control;

wherein a difference in expression of NetF or NetG toxin in the sample from the subject as compared to the control is indicative of enteric disease in the subject.

In one embodiment, the NetF or NetG toxin comprises any of the polypeptides disclosed herein or is encoded by any of the nucleic acid molecules disclosed herein.

In another embodiment, the method further comprises obtaining a sample from a subject prior to (a).

In an embodiment, the NetF or NetG toxin is detected in step (a) by detecting a nucleic acid molecule encoding the toxin in the sample by hybridization using a probe specific for the toxin or by PCR using primers specific for the toxin, such as the sequences shown in SEQ ID NOs:9, 10, 11 or 12.

In another embodiment, the NetF or NetG is detected in step (a) by detecting a NetF or NetG polypeptide using an antibody that specifically binds the NetF or NetG. In one embodiment, the antibody is a polyclonal antibody. In another embodiment, the antibody is a monoclonal antibody.

The term "control" as used herein refers to a sample from a subject or a group of subjects, which do not have enteric disease. The control can also be a predetermined standard.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

Examples

Results

Identification and Analysis of Novel Putative Necrotizing Toxins.

The automated annotation of the draft genome sequences of *C. perfringens* canine strain JP718 were used to isolate three putative toxin genes, initially denominated as Panton-Valentine leukocidins (PVLs). Two PVL open reading frames (ORF) were located in scaffold00006 (nucleotides 139809-140777 [−] and 154804-155721[+]), while the third was in scaffold00012 (nucleotides 9399-10319 [+]), both surrounded by transposon-related sequences. Interestingly, both scaffolds (00006 and 00012) contained mainly plasmids genes, suggesting that these sequences were associated with a transposable element and/or plasmid (Table 8). The newly identified toxin genes were named netE, netF and netG. The predicted proteins (NetE, NetF and NetG) encoded by these three ORFs showed 79%, 48% and 52% amino acid identity with the pore-forming toxin NetB from *C. perfringens* (EU143239), respectively (Table 1 and FIG. 7). NetF has 60% identity with NetG and 51% with NetE, whereas NetG has 52% identity with NetE. NetE has been previously described in PCT publication WO2013/173910. Scaffold 00006 harbors netE and netF toxin genes among 140 ORFs. Immediately upstream of the netE and netF genes, which are 14,027 nt apart, are two mobile element proteins classified as an integrase (*C. botulinum* BKT015925) and a transposase (*C. perfringens*), whereas downstream of netF gene there is another integrase (*C. botulinum* BKT015925) (FIG. 1A, Table 8). Scaffold 00012 harbors the netG gene as well as the cpb2 (CPB2 toxin) (54351-55052) and cpe (67515-68474) genes (FIG. 1B, Table 8).

Figure 2:
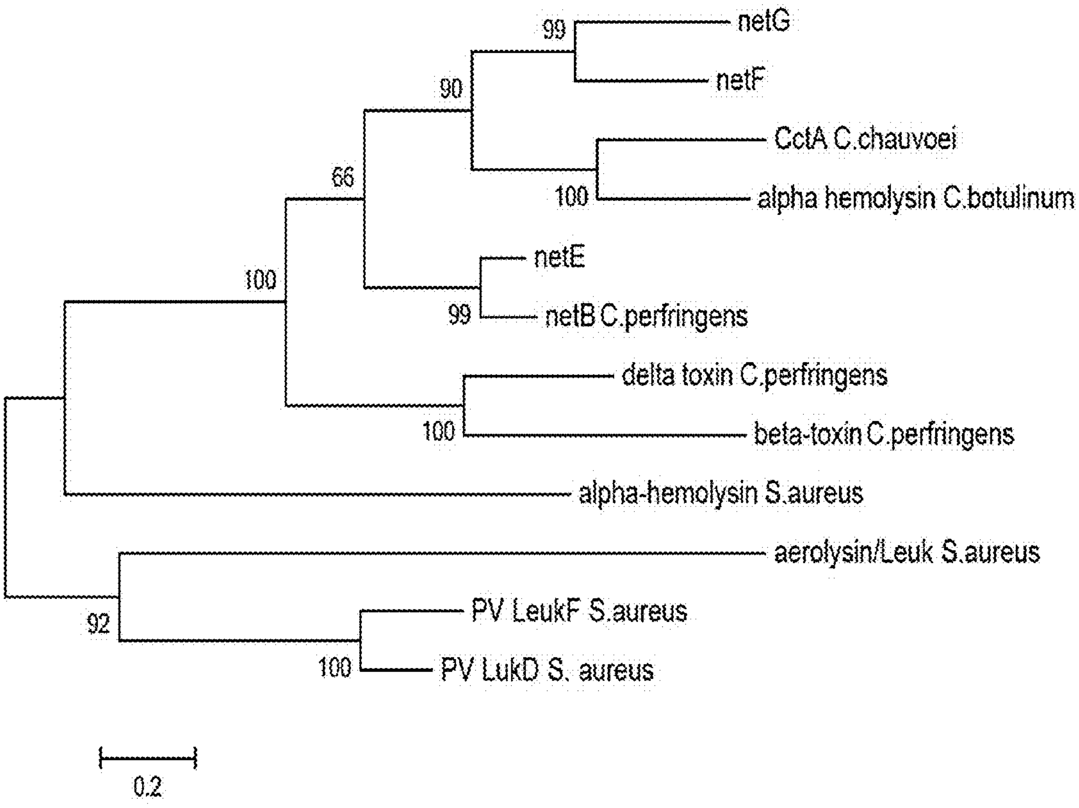
FIG. 2 shows phylogenetic analysis of representative members of the the Leukocidin/Hemolysin superfamily. The phylogenetic tree was built by the Neighbor-joining algorithm using (1000 interactions) MEGA5 software (Saitou and Nei, 1987). The tree is drawn to scale, with branch lengths in the same units as those of the evolutionary distances used to infer the phylogenetic tree. Toxins that were used included: alpha-hemolysin of *C. botulinum* (YP_004394739.1), hemolysin II of *B. cereus* (YP_002447023.1), alpha-hemolysin of *S. aureus* (WP_001788633), putative CctA of *C. chauvoei* (WP_021874975) and beta-toxin of *C. perfringens* (CAA58246.1).

Sequence analyses of these ORFs were performed using BLAST, BLASTP, the Conserved Domains Database (CDD) (Marchler-Bauer et al., 2009), SignalP (Dyrløv Bendtsen et al., 2004), pSortB (Gardy et al., 2005), and InterProScan (Zdobnov and Apweiler, 2001) (Table 1). Analysis against the CDD conserved domain database showed these newly described net genes to belong to the Leukocidin/Hemolysin superfamily. InterProScan analysis and classification also confirmed the presence of the Leukocidin/Hemolysin domain (IPR001340) and classified them as members of the bi-component staphylococcal toxin gene family (IPR003963). The genes were predicted by pSortB and SignalP to encode extracellular proteins. netE encodes a putative 322 amino acid (aa) protein with a signal peptide region of 30 residues, netF encodes a 305 aa protein, and netG encodes a 306 aa protein, both with a signal peptide region of 24 residues. The predicted respective molecular size of the mature NetE toxin is 32.9 kDa, and of NetF and NetG are 31.7 kDa. The close relationship of the Net toxins to other members of the Leukocidin/Hemolysin pore-forming toxin family is shown through the Clustal W alignment (FIG. 7) and phylogenetic tree (FIG. 2) (Saitou and Nei, 1987). For NetE, the closest ortholog (79% identity) is NetB from *C. perfringens*, whereas NetF and NetG were placed in their own branch (FIG. 2).

The VirR/VirS two-component signal transduction system regulates several virulence genes in *C. perfringens*, including cpa (alpha-toxin or phospholipase C), pfoA (perfringolysin O or theta-toxin) and colA (kappa-toxin or collagenase) (Ohtani et al., 2010). Analysis of the upstream region of net genes revealed the presence of potential VirR boxes in the promoter region of netE and netG, but not of netF (Table 9).

Cytotoxicity of *Clostridium perfringens* Type A Isolates.

To determine whether *C. perfringens* type A strains isolated from fatal cases of canine hemorrhagic enteritis and foal necrotizing enteritis produced a distinct secreted toxin, sterile culture supernatants of strains JP718 (canine origin) and JP728 (equine origin) were tested for cytotoxicity against 10 cell lines derived from 9 animal species (Table 2). The culture supernatants of the two strains showed potent cytotoxic effects for an equine ovarian cell line (EO) at a dilution of 1:128, with far less or no toxicity against other cell lines tested (Table 2). By contrast, supernatants derived from NCTC3110 (cpb positive), JP564 (cpb2 and cpe positive), SM101 (cpe positive) and CW504 (cpa positive) displayed mild or no cytotoxic effects on EO cells, indicating that toxicity of JP728 and JP718 strains was caused by a secreted component(s) distinct from other known toxins (Table 3).

PFGE Analysis and Southern Blot (SB).

Figure 3:
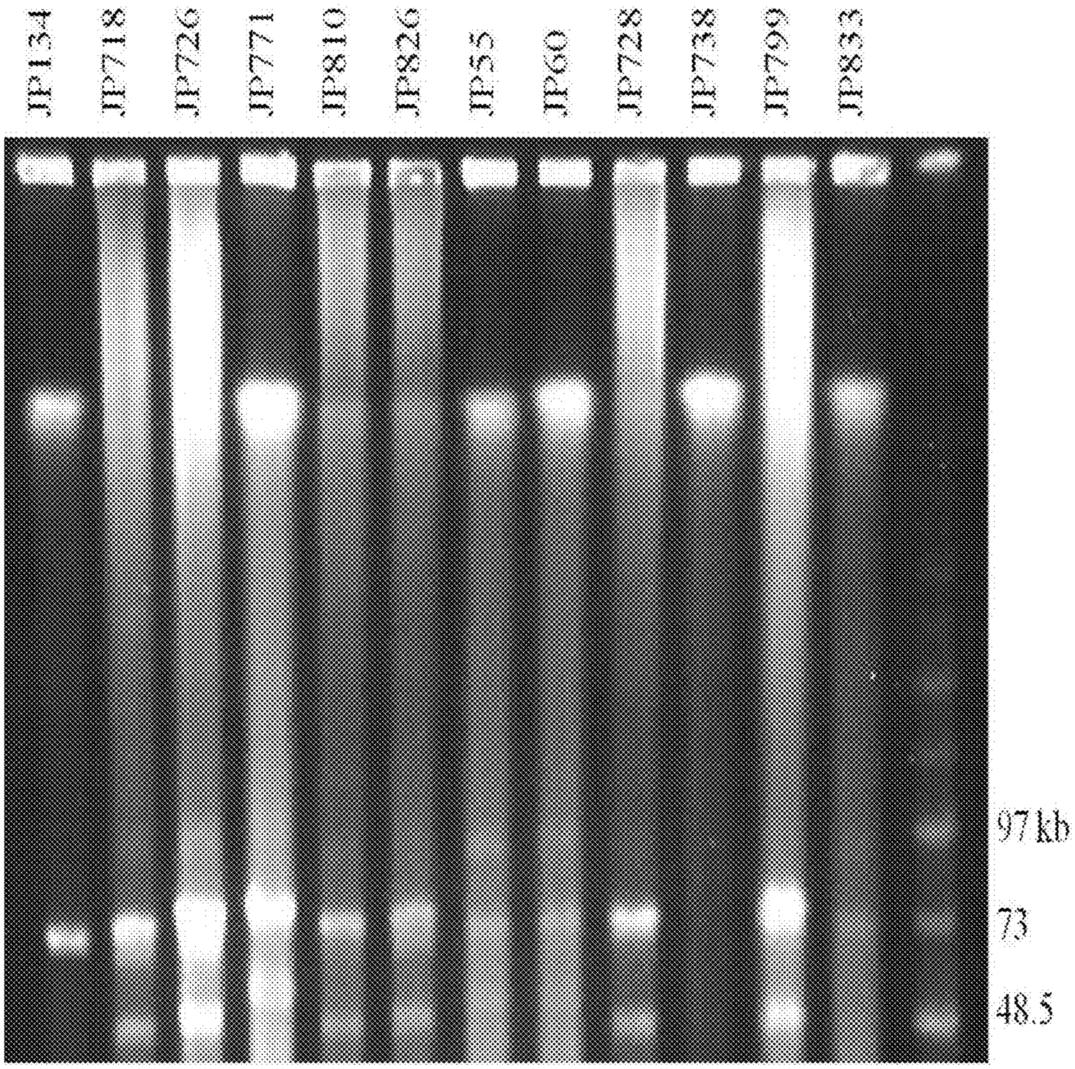
FIG. 3 shows PFGE analyses of plasmids from canine and equine *C. perfringens* strains. Agarose plugs containing DNA from each specified isolate were digested with NotI and subjected to PFGE and staining with ethidium bromide. Line numbers indicate isolate numbers M: Mid-Range II PFG molecular DNA ladder (Kb).
Figure 4:
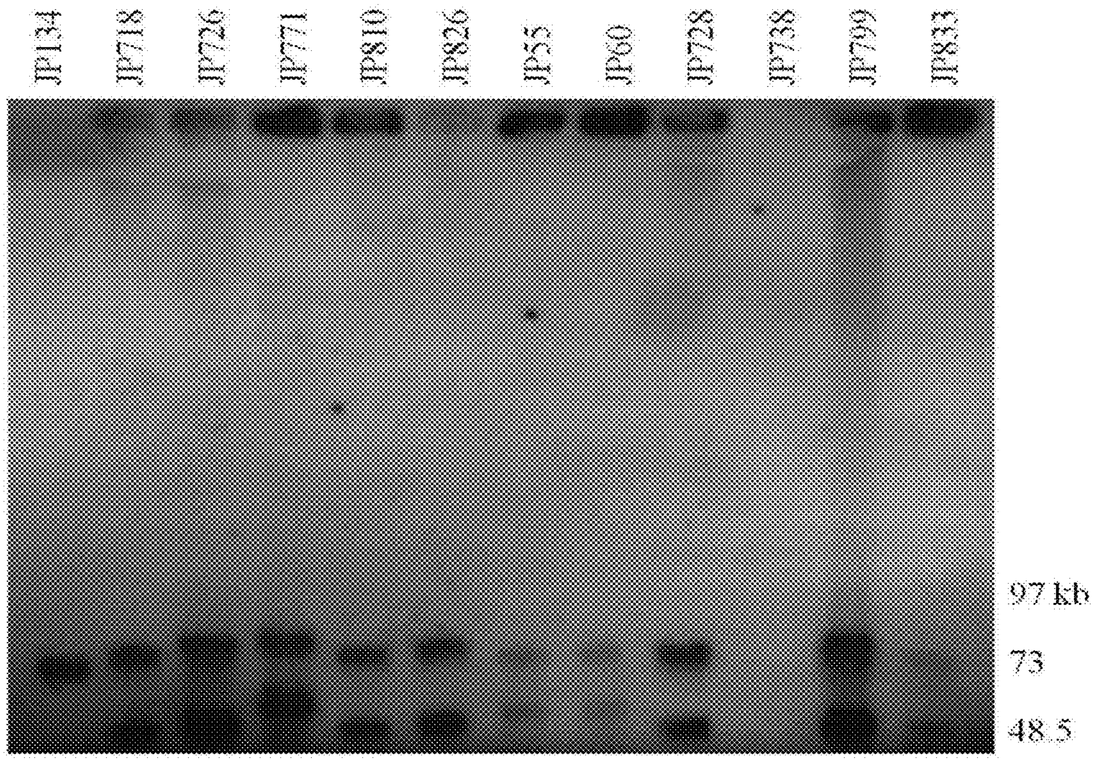
FIG. 4 shows PFGE-Southern blot of plasmids from canine and equine *C. perfringens* strains. Southern blotting of PFGE was performed with DIG-labelled probes for netE and cpe genes. Results from both netE and cpe probes are shown overlayed. In all lanes with two bands, the upper band represents netE and the lower band cpe. M: Mid-Range IIPFG molecular DNA ladder (Kb).

To determine the presence of large plasmids in equine and canine type A *C. perfringens* isolates, DNA from six canine and six equine isolates (Table 4) were subjected to PFGE. The PFGE profiles of the canine and equine *C. perfringens* strains digested with NotI revealed the presence of two to three large plasmids ranging in size from 45-97 kb in all strains (FIG. 3, Table 5). PFGE analysis (FIG. 3) shows the diversity of plasmids among these type A isolates and their marked size variations, which were confirmed by PFGE/SB studies (FIG. 4). Specifically, the sequenced canine type A *C. perfringens JP*718 strain carried three large plasmids (FIG. 3) in which the netE and cpe genes were on a distinct plasmid (FIG. 4). The SBs showed the presence of tcpF in all the large plasmids. In addition, cpb2 was identified by SB in the netG plasmid as described in the scaffold 00012 confirming the hypothesis that these two scaffolds represent two distinct plasmids. The non-cytotoxic strains JP134 (canine) and JP738 (equine) which showed one and no large plasmids, respectively, were also PCR negative for netE, netF and netG genes, while the cpe gene was positive only in JP134.

PFGE Analysis of netF-Positive and Negative Canine and Equine Type A *C. perfringens.*

Figure 5:
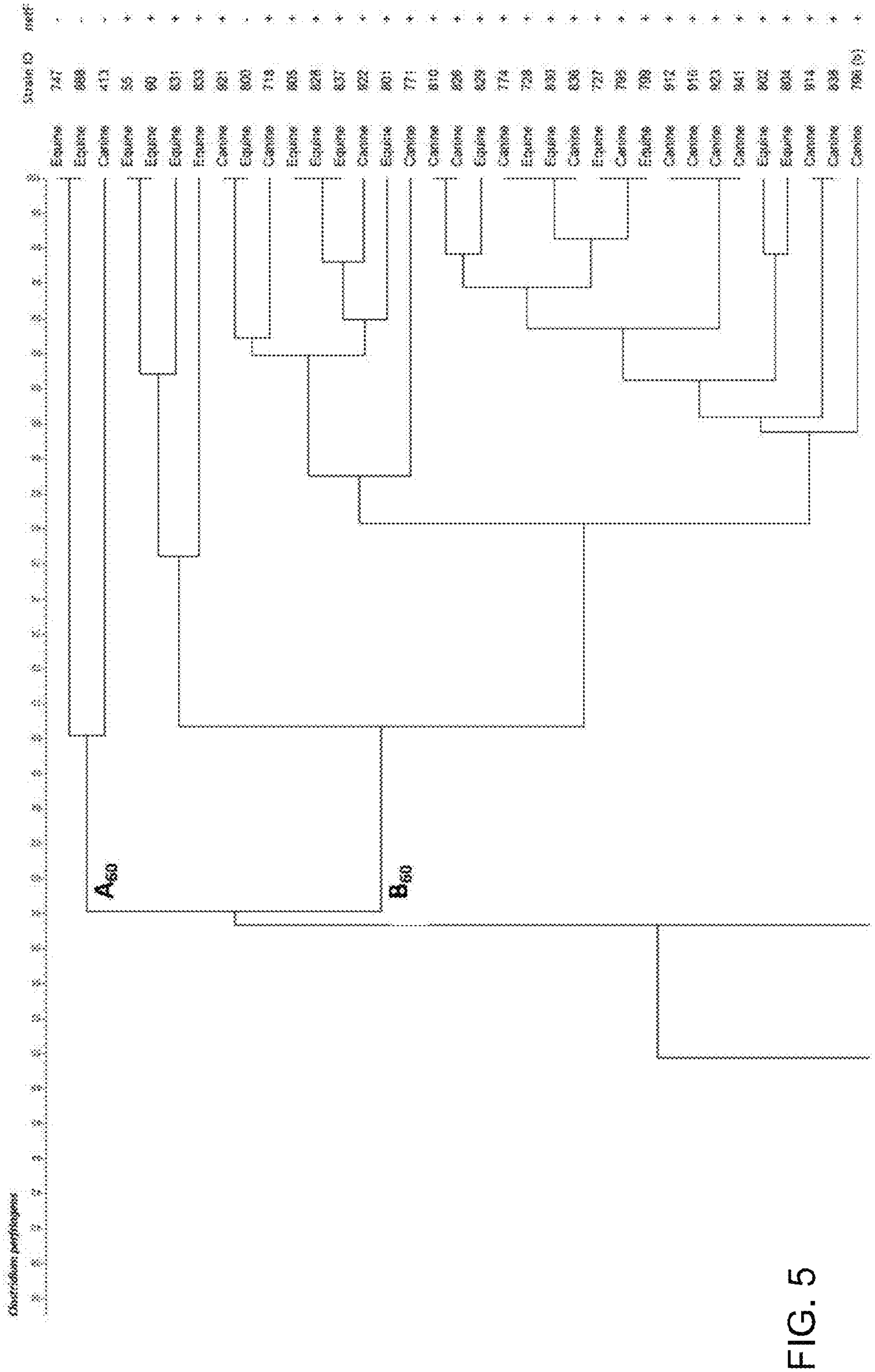
FIG. 5 shows a dendogram of *Clostridium perfringens* isolates. Dendogram of *C. perfringens* isolates typed by pulsed-field gel electrophoresis and analysed using BioNumerics software. The BioNumerics software used was version 7.1 from Applied Maths, Austin, Tex.
Figure 5:
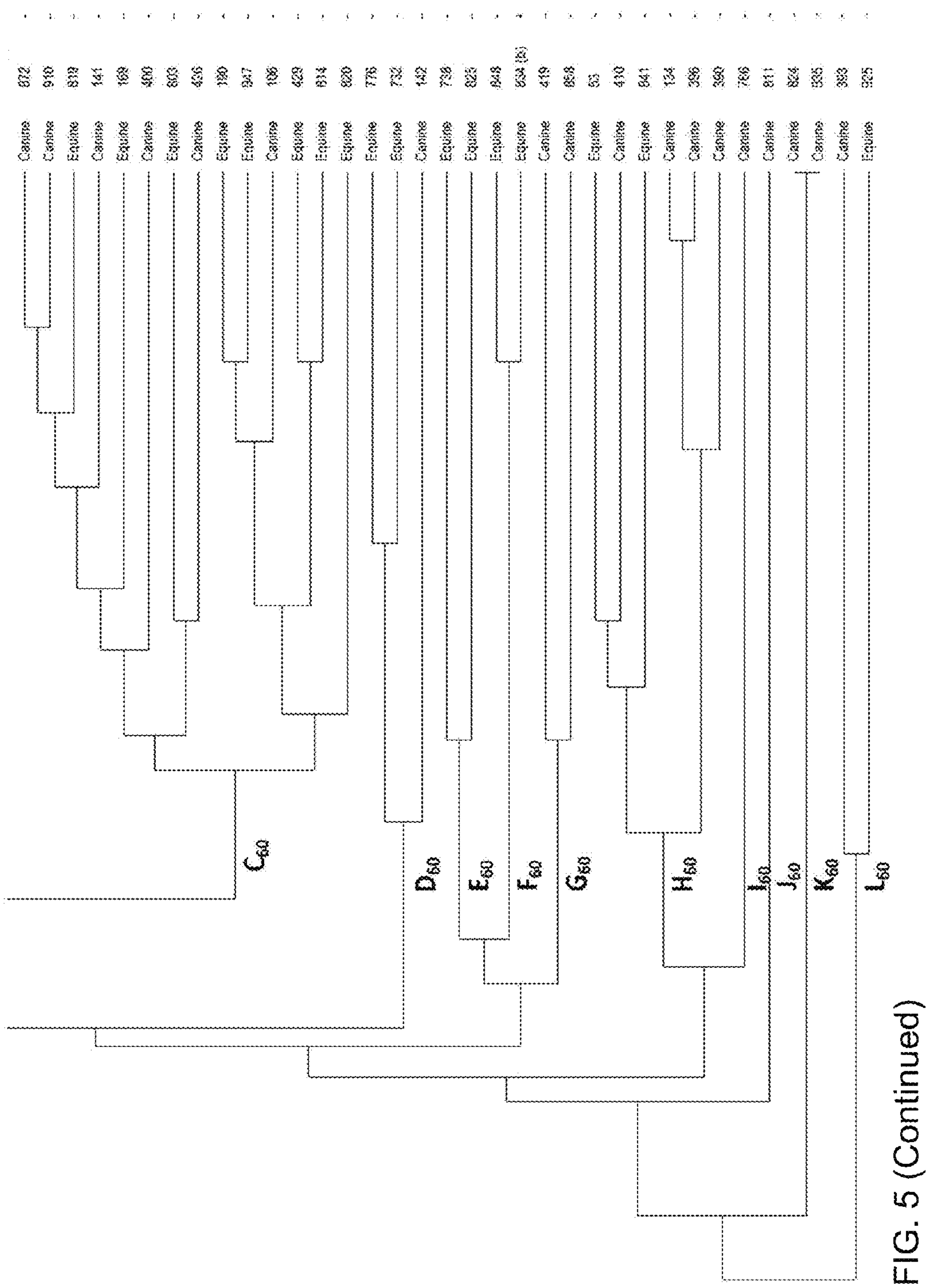

The PFGE analysis and the dendogram are shown in FIG. 5. Out of the 70 isolates (35 equine and 35 canine) typed by PFGE, 56 (80%) individual pulse types were identified based on an identical banding pattern (genetic similarity of 100%). Eighteen of these 56 were positive for netF, 37 were negative for netF, and one type contained both netF+ and netF− isolates that were equivalent. There was no distinguishable pattern of equine versus canine types (FIG. 5).

Twelve genotypes (A to L) were distinguished using the criterion of 60% genetic similarity (FIG. 5). All but one of the netF+ strains belonged to one genotype when using this relatedness criterion (FIG. 5). The netF− isolates comprised a wider diversity of genotypes (FIG. 5). Only one netF+ isolate, JP834, was included in one of these netF− genotypes.

Mutation of netE, netF and netG and Conjugation.

The netE, netF and netG genes were insertionally inactivated in strain JP838, resulting in the mutant strains JP838E-05, JP838F-05 and JP838G-07, respectively. The insertion of ErmB-carrying introns into each of the three target genes was confirmed by PCR using primers flanking the insertion site. Resistance to erythromycin was subsequently used as a mutant or conjugation selection marker.

Plasmids (pNetE/NetF, pNetG) were transferred to the recipient strain in conjugation assays. Erythromycin-resistant transconjugants were confirmed by specific PCR amplifications of netE, netF and netG genes; the ermB gene was amplified from the transconjugants but not from the wild-type or donor strain. Culture supernatants of each transconjugant were tested for cytotoxicity on EO cells. The transconjugant T504-05ΔnetE, which harboured only the pΔnetE/netF plasmid, showed cytotoxicity, which was similar to that of the wild-type JP838 strain. This suggested that the NetF toxin was producing the cytotoxic effect To show that the cytotoxicity was related entirely to NetF and not to any other protein in the pNetE/NetF plasmid, the netF gene amplified by PCR was cloned into the shuttle vector pJIR750Cm$^R$ and electroporated into *C. perfringens* strain JIR325. This recombinant strain, JPnetF, which expressed only the NetF toxin, was found to have cytotoxicity for EO cells similar to that of wild-type strain JP838.

Complementation of *C. perfringens.*

Figure 6:
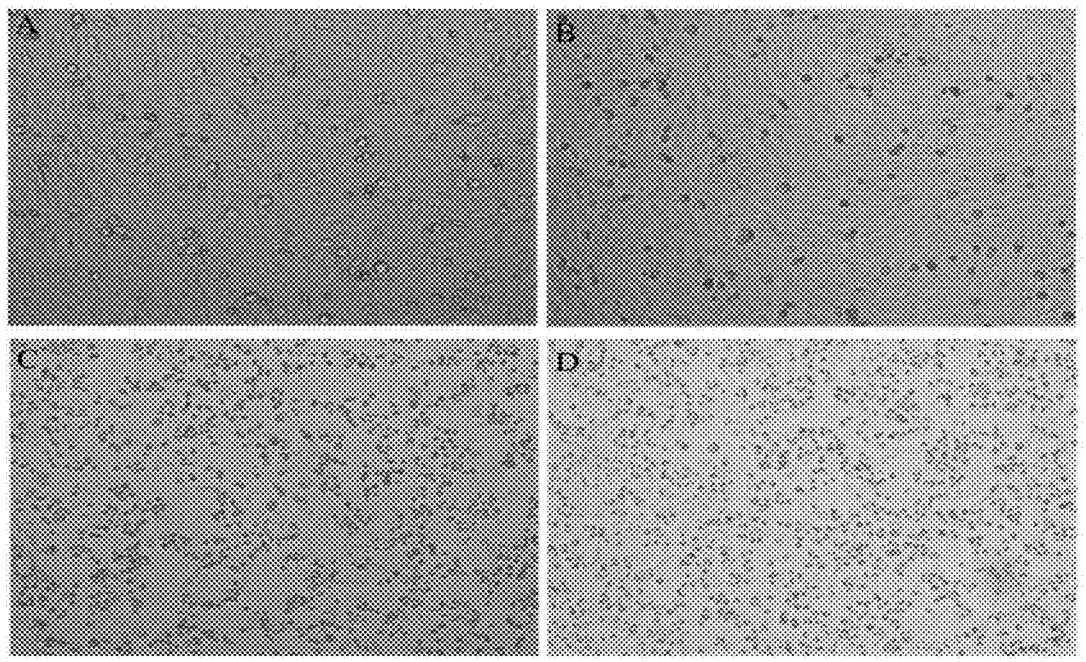
FIG. 6 shows infection and cytotoxic effects on equine ovarian (EO) cells by supernatant from JP838 and its isogenic derivatives. Confluent EO cell cultures were infected for 8 h at 37° C./5% CO2. Filter-sterile broth culture supernatants were used for these infections: (A) Typical morphology of EO cells, (B) JP838-F05 (netF null mutant), (C) Wild-type JP838, (D) Complementing strain VN-22C. Cytotoxic effects to EO cells in these conditions were cell rounding, detachment and death of cell in the cell plate, seen in FIGS. 6C and 6D. Magnification×100.

The non-cytotoxic mutant strain JP838F-05 was complemented in trans with pNetF-07, which contains the wild-type netF gene. The netF gene in the pNetF-07 restored the cytotoxicity of the JP838 netF mutant (JP838F-05) to that of the wild-type JP838 (FIG. 6). This is additional evidence that, of the three net genes found in these cytotoxic strains, netF is responsible for the cytotoxic activity.

Prevalence of net Genes and their Association with Foal Necrotizing Enteritis and Canine Hemorrhagic Enteritis, and with Cytotoxicity.

The netF gene was identified in 11 of 15 isolates (74%) from different foals with fatal necrotizing enteritis whereas it was not found in 11 foals with undifferentiated diarrheal disease ($p<0.00019$; MUE=31.45, CI=5.35-∞). The netF gene was only identified in 4 of 58 (6.8%) isolates from adult horses with undifferentiated diarrheal disease ($p<0.0000004$; CMLE≈33.63, CI=6.58-170.95). In canine fatal hemorrhagic gastroenteritis, the netF gene was found in 8 of 11 isolates (73%) compared to 8 of 81 (10%) undifferentiated canine diarrheal isolates ($p<0.000000081$; CMLE≈40.44, CI=8.01-204.72).

PCR analysis of equine and canine netF-positive isolates (n=31) showed that the netF gene was always (100%) found in association with both the netE gene and the cpe enterotoxin gene, but in fewer (55%) isolates with the netG gene. netG was found in 5 of 11 (46%) isolates from canine hemorrhagic gastroenteritis compared to 7 of 81 (9%) isolates from dogs with undifferentiated diarrheal disease (p<0.0049; CMLE≈8.46, CI=2.05-36.36). netG was only identified in 7 of 15 (47%) of foal necrotizing enteritis isolates compared to none of 11 foals with undifferentiated diarrheal disease (p<0.01; MUE=11.15, CI=1.9-∞) and none of 58 adult horses with undifferentiated diarrheal disease (p<0.000004, MUE=59.95, CI=10.75-∞).

None of 24 caprine, 28 ovine and 47 bovine different source isolates tested was netE, netF or netG positive.

Subsequent PCR amplifications of the netE, netF and netG genes from three canine hemorrhagic enteritis isolates and three other foal necrotizing enteritis isolates and DNA sequencing showed these genes to be fully conserved at the nucleotide level.

The supernatant of 29 of 31 canine and equine netF-positive isolates was as toxic as that of JP728 for the EO cell line. Of 176 different *C. perfringens* isolates tested, 29 of 31 netF-positive strains were cytotoxic compared to none of 145 netF-negative strains; immunoblots of the two nontoxic netF-positive strains revealed that NetF was not produced in these two strains.

Recombinant Net Toxins.

Recombinant Net toxins (rNetE, rNetF and rNetG) were engineered without the signal peptide (SP) sequence and, because of solubility problems, were purified under denaturing conditions using 8 M urea. To obtain soluble recombinant Net toxins, rNet proteins were constructed with the *E. coli* fusion protein NusA (45 kDa). SDS-PAGE and immunoblot results showed that the fusion proteins were expressed at a high level in a soluble form.

To determine whether rNet proteins were active, EO cells were treated with purified rNet-NusA proteins; purified rNusA protein was used as a negative control. Cytotoxicity of the purified recombinant Net-NusA proteins was low in comparison to that of the positive control strain: JP728 1:128; rNetE-NusA 1:2; rNetF-NusA 1:8; rNetG-NusA 1:2. rNet-NusA proteins were also tested for hemolytic activity with horse red blood cells (Yan et al., 2013). JP838 supernatant was hemolytic for horse RBC, whereas rNet-NusA toxins were inactive.

Cytotoxin Neutralization by Equine Polyclonal Antibodies.

Immunoblotting of SDS-PAGE separated rNetE-NusA, rNetF-NusA or rNetG-NusA showed cross-reactivity of sera prepared against each of the recombinant proteins. Cross-reactivity similar to that noted in immunoblotting was also apparent in ELISA when these sera were tested against individual rNet-NusA proteins (Table 6), with the titer (and immunoblot cross-reactivity) being highest against the homologous protein. Only horses immunized with rNetF-NusA showed a high degree of cytotoxin neutralizing activity when tested against supernatant from wild-type (netE/F/G) positive strains (Table 6).

To determine the specificity of antibodies produced in horses to the individual rNet-NusA proteins, immunoblot of culture supernatants of two type B (cpb-positive), two type C (cpb-positive) and two type A netB-positive strains was performed using horse sera prepared against rNet-NusA proteins. Antisera prepared against each of the recombinant proteins interacted weakly with NetB but not with the CPB toxin in type B or C strains.

Discussion

This study advances understanding of type A *C. perfringens* as an enteric pathogen of animals by identifying a novel pore-forming toxin within the Leukocidin/Hemolysin superfamily, NetF, and the association of a clonal population expressing this toxin with two distinct severe enteric diseases, canine hemorrhagic gastroenteritis and foal necrotizing enteritis.

A partial genome sequence identified three distinct genes within the Leukocidin/Hemolysin pore-forming superfamily to which the α-toxin of *Staphylococcus aureus* and β-toxin and NetB of *C. perfringens* belong. Immunoblotting showed that each of the three putative toxin genes, which were named netE, netF, and netG, were expressed. Confirmation that NetF was the cytotoxic factor in the supernatant of isolates with these genes was in three ways. Firstly, only mutation of netF removed the cytotoxic effect, which was complemented by netF gene replacement (FIG. 6); secondly, only netF introduced into a laboratory strain of *C. perfringens* produced cytotoxicity in the bacterial supernatant, which was also found to be equivalent to wild-type cytotoxicity; and, thirdly, only antiserum produced against recombinant NetF protein neutralized the cytotoxicity of supernatants at high titer (Table 3).

The initial choice of an equine cell line (EO) to screen the supernatants of isolates from foal necrotizing and canine hemorrhagic enteritis was fortuitous since it is considerably more susceptible than cell lines obtained from other species (Table 3). The susceptibility of the EO cells may relate to specific receptors or factors other than those relating simply to the animal host of origin of the cell line. Others have found marked differences between chicken cell lines in susceptibility to NetB, a related pore-forming toxin important in the pathogenesis of necrotic enteritis of chickens (Keyburn et al., 2008).

The advantage to these netF-positive strains of expressing three different β-pore-forming toxins is unclear, but, without wishing to be bound by theory, they might contribute to the ability to cause disease in specific hosts other than dogs and horses. It is possible that other, not yet identified cell lines, will be susceptible to NetG (and NetE) toxins. An alternate possibility is that NetE and NetG might have cytotonic effects, such as proinflammatory effects, as has been shown with pore-forming Leucocidins of *Staphylococccus aureus* (Alonzo and Torres, 2014). There may also be synergism with other toxin molecules (Alonzo and Torres, 2014).

Figure 7:
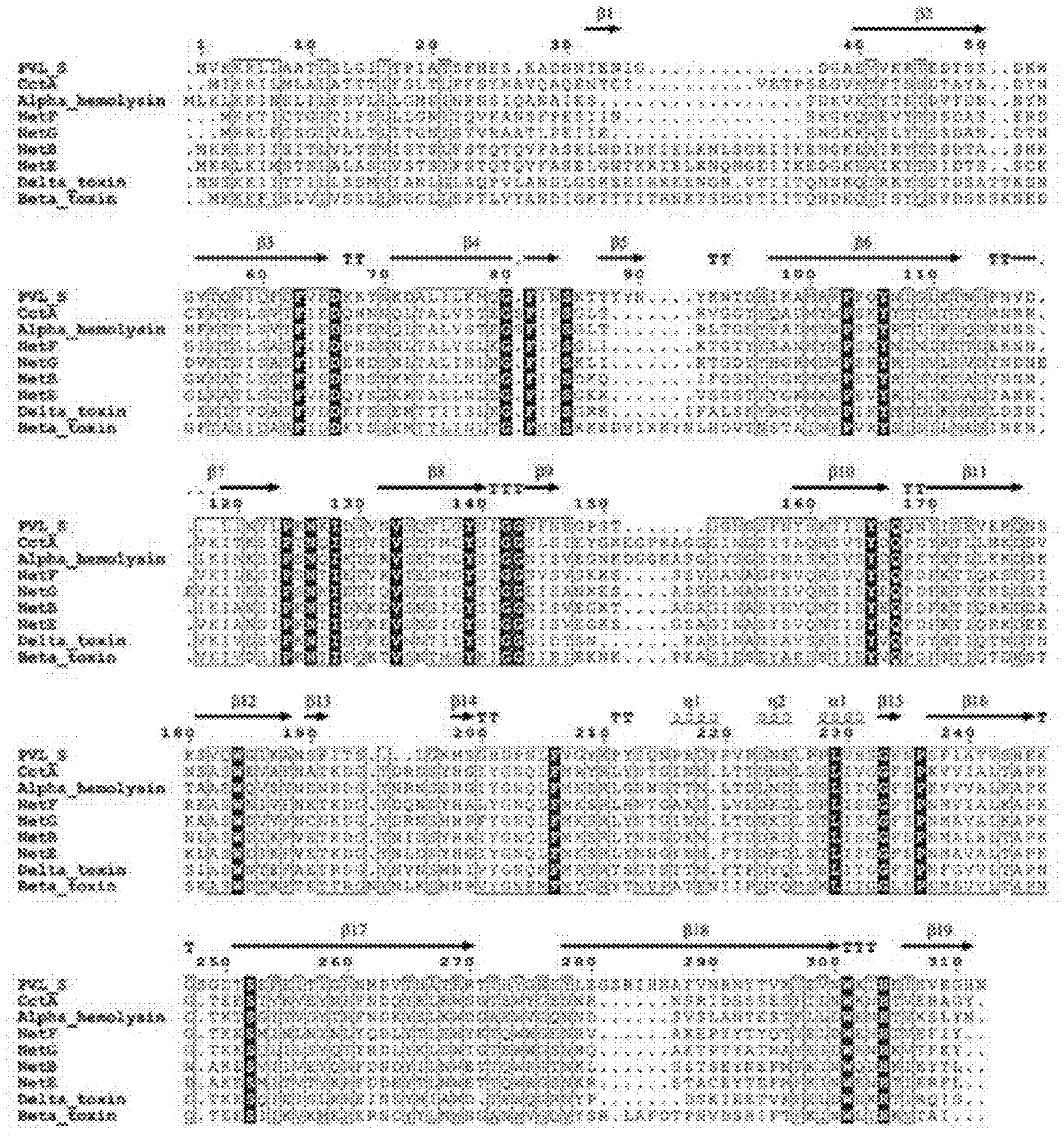
FIG. 7 shows sequence alignment of toxins from *Clostridium perfringens*. Residue numbers for individual proteins are given on the top of the sequences. Filled-in boxes represent identical residues, whereas outlined boxes represent similar residues. The secondary structure is shown on top based on their respective crystallographic structures (β=beta-strand, $\eta=3_{10}$ helix, α=alpha-helix, strict β-turns=TT and strict α-turns=TTT). The alignment was performed using ClustalW of the toxins Panton-Valentine leukocidin S of *Staphylococcus aureus* (AHC29058) (SEQ ID NO:50), putative CctA of *C. chauvoei* (WP_021874975) (SEQ ID NO:51), alpha-hemolysin of *C. botulinum* (YP_004394739.1) (SEQ ID NO:52), NetE (KJ606985) (SEQ ID NO:47), NetF (KJ606986) (SEQ ID NO:3), NetG (KJ606987) of *C. perfringens* (SEQ ID NO:4), NetB of *C. perfringens* (EU143239) (SEQ ID NO:53) and Delta toxin of *C. perfringens* (EU652406) (SEQ ID NO:54) and Beta-toxin of *C. perfringens* (CAA58246.1) (SEQ ID NO:55). The figure was created using the ESPript 2.2.program.

Pore-forming toxins (PFTs) to which these Net proteins belong, are potent cytolytic agents secreted by pathogenic bacteria that protect microbes against the cell-mediated immune system, disrupt epithelial barriers, and liberate materials necessary to sustain growth and colonization. Produced by Gram-positive and Gram-negative bacteria alike, PFTs are released as water-soluble monomeric or dimeric species, bind specifically to target membranes, and assemble transmembrane channels leading to cell damage and/or lysis (De and Olsen, 2011). De and Olsen (2011) have shown that distantly related toxins from different organisms adopt a similar pore-forming architecture and that conservation of many of the key amino acids seems to be essential for their function (FIG. 7). Savva et al. (2013) have identified conserved and non-conserved amino acid positions that affect binding and toxicity of NetB. Interestingly tyrosine at one position (NetB:Tyr-202) is only conserved in the clostridial toxins. Thus the clostridial and staphylococcal members of the β-PFTs family may bind to host membranes using different mechanisms involving interactions with different lipids. The structure of the β-PFTs shows a ring-shaped complex which resembles a mushroom; on the rim domain Trp-257 and Trp-262 have been shown to be involved in cell binding (Savva et al., 2013). Substitution to alanine at either position reduced NetB cytotoxicity and hemolysis on LMH cells and on RBCs, respectively. These residues are highly conserved in β-barrel PFTs of *S. aureus* and *C. perfringens*, as well as in NetE, NetF and NetG (FIG. 7), although these toxins were not hemolytic in RBCs. The identification of three new members of the Leukocidin/Hemolysin family of β-barrel PFT may provide additional proteins with which to explore the receptor-based selectivity and specificity of members of this family (Huyet et al., 2013; Yan et al., 2013).

Clonal expansion and niche specialization is well recognized in particular types of *C. perfringens* (Popoff and Bouvet, 2013), such as cpe-bearing type A food poisoning isolates (Xiao et al., 2012), porcine cna and cpb2-containing isolates (Jost et al., 2006), and cpb2 and netB-containing poultry isolates (Chalmers et al., 2008; Hibberd et al., 20114). The clonality of the canine and equine netF-positive strains identified herein, and the lack of any immediately obvious common infectious source relationship between dogs and neonatal foals, might suggest that they are infected by strains adapted to a common environmental source rather than to dogs or horses. The close relatedness, or in some cases the identity, of canine and equine isolates identified by PFGE was mirrored in the complete nucleotide conservation of the net genes, though size differences were noted in the plasmids encoding these genes (FIG. 3).

The virulence of *C. perfringens* is dependent on its remarkable ability to produce a variety of toxins, of which some of the most toxic are found on the large family of conjugative tcp plasmids (Bannam et al., 2011; Parreira et al., 2012; Li et al., 2013). Although strains may carry up to three different large plasmids, the present inventors only found two in the majority of pNetF-positive isolates, one carrying netE and netF, and the other consistently carrying the cpe enterotoxin gene and often the netG gene. *Clostridium perfringens* virulence plasmids share a conserved backbone sequence which contains among other genes the tcp conjugation locus (Parreira et al., 2012). The tcp locus is present on all known conjugative plasmids from *C. perfringens* and consists of 11 genes (tcpA to tcpJ), of which two (tcpF, tcpH) are essential for conjugative transfer (Bannam et al., 2006). pNetF and pNetG plasmids carried tcpF genes as shown by SB, and conjugation assays suggest that both plasmids are also conjugative. This study has added further to understanding of the role of these plasmids in the adaptability and flexibility of virulence in *C. perfringens* (Li et al., 2013). The likely basis of the presence of independently conjugative plasmids with large common genetic regions has been suggested (Bannam et al., 2011) and identified (Parreira et al., 2012; Lepp et al., 2013). Although toxin gene-bearing large plasmids are recognized to be critical in the virulence of *C. perfringens*, more recent understanding has focused on the importance of the chromosomal background in which these plasmids exist (Lepp et al., 2013), since chromosomal genes may serve to enhance both the host specificity and the virulence of the strain. The netF-positive strains were almost entirely clonal (FIG. 5), suggesting that the chromosomal background may be important for maintenance of these plasmids and/or for virulence. As such, NetG may be an important toxin in a different chromosomal background or may have an effect in a different animal host species, i.e. in a host with a different chromosomal background (for example, other than the horse or dog species tested herein). A feature of the netF-positive strains identified herein was that they always contained one plasmid with netE and netF and another with cpe and usually, but not always, with netG. The relatedness of strains carrying a plasmid-encoded cpe has been noted previously (Deguchi et al., 2009) but not at the degree of conservation identified herein.

Many toxin genes in *C. perfringens* are positively regulated at exponential phase by the two-component VirR/VirS system that is a major regulator of virulence in *C. perfringens* (Ohtani et al., 2010). The present inventors found that netE and netG genes have a putative VirR box upstream of their start site, and it is therefore possible that these toxin genes are regulated by the VirR/VirS system as are many other *C. perfringens* toxins. Obana and Nakamura (2011) have shown that CPE1447 and CPE1446 control target genes as transcriptional regulators as novel transcriptional regulators. This might also be the case in the regulation of NetF toxin, since no VirR box was found. In other words, without wishing to be bound by theory, NetG and NetE may be toxin regulators of NetF.

Canine hemorrhagic gastroenteritis has long been a poorly understood disease of dogs, known to be often associated with *C. perfringens* and characterized by its dramatic and sometimes fatal nature (Burrows, 1977; Unterer et al., 2014). The pathology of fatal cases of *C. perfringens*-associated canine hemorrhagic gastroenteritis is characterized by coagulative necrosis in the small intestine, a disease process typically associated with pore-forming toxins in *C. perfringens*. This study associates netF-producing strains with this disease, and may contribute to improved diagnosis, treatment and control. In the light of the current advance in understanding the basis of canine hemorrhagic gastroenteritis, the well-recognized association of this disease with small breed dogs (Burrows, 1977; McGavin and Zachary, 2007; Unterer et al., 2014) may be explained by the increased incidence of pancreatitis in small rather than in large breed dogs (Chase et al., 2009), since pancreatitis will disrupt pancreatic trypsin production. By analogy, fatal type C *C. perfringens* enteritis has commonly been associated with trypsin inhibition by foods such as cassava, or by trypsin inhibitory factors in colostrum, with the consequence that CPB toxin produced in the small intestine is not destroyed by the proteolytic action of trypsin but rather initiates intestinal necrosis and cascading clostridial disease (Songer, 1996).

Enterocolitis in neonatal foals associated with types A and C *C. perfringens* is associated with high mortality (East et al., 2000), but the role of type A isolates has not been defined. This study clearly identified the association of type A strains producing the novel pore-forming toxin NetF with this disease, and opens the way for control based on immunoprophylaxis or for measures based on future understanding of the epidemiologic basis of the disease (East et al., 2000; Tillotson et al., 2002). Most foals with *C. perfringens*-associated enterocolitis have been younger than three days of age (Traub-Dargatz and Jones, 1993), also thus supporting a role for the trypsin-inhibitory action of colostrum (Quigley et al., 1995) in interfering with the breakdown of *C. perfringens* toxins as an important feature of its pathogenesis.

Materials and Methods

Bacterial Strains, Plasmids and Growth Media.

Bacterial strains and plasmids used are described in Tables 4 and 7, respectively. *Clostridium perfringens* strains were grown overnight at 37° C. under anaerobic conditions (80% $N_2$, 10% $H_2$, 10% $CO_2$) on either TPG medium (5% Tryptone [Becton, Dickinson and Company, Sparks, Md.], 0.5% proteose peptone [Fisher Scientific, ON], 0.4% glucose [Fisher Scientific], and 0.1% thioglycolic acid [Sigma-Aldrich, St. Louis, Mo.]) or Brain Heart Infusion (BHI) agar (Becton, Dickinson and Company). All *C. perfringens* isolates were also cultivated in blood agar (Trypticase Soy Agar [Fisher Scientific] with 5% sheep blood) plates aerobically to confirm purity. *Escherichia coli* strains DH5α (Stratagene, La Jolla, Calif.) was used as the host for plasmid construction, *E. coli* BL21-Star (DE3) pLysS (Invitrogen, Carlsbad, Calif.) was used for the overexpression of histidine-tagged fusion proteins, and *E. coli* CA434 for conjugation assays (Table 4). *Escherichia coli* strains were grown on Luria-Bertani (LB) broth or agar plates (Becton, Dickinson and Company) overnight at 37° C. All strains were stored at −70° C. in lyophilizing medium (25 g powdered skim milk [Fisher Scientific], 18.75 g glucose, 25 g sucrose [Sigma-Aldrich], 2.5 g bovine albumin [Sigma-Aldrich] in 250 ml distilled water).

Identification of Necrotizing Toxin Genes.

The identification of necrotizing toxin genes netE, netF and netG was made possible by the sequencing of a canine strain of *C. perfringens* (JP718) carried out by the McGill University and Genome Quebec Innovation Centre (Montreal, QC). The pseudochromosome, plasmid fragments, and unplaced contigs were automatically annotated by Rapid Annotation using Subsystem Technology (RAST). BLASTN and BLASTX analyses were performed to compare the established sequences to known *C. perfringens* sequences in the NCBI database.

Genomic and Plasmid DNA Isolation.

A 1 ml aliquot of TPG medium cultured at 37° C. overnight was spun down at 12,000 rpm and DNA of the samples were extracted using InstaGene Matrix (Bio-Rad Laboratories, Mississauga, ON) following the manufacturer's directions. Plasmid DNA was purified using midi-Qiagen columns (Qiagen, Mississauga, ON) following the manufacturer's instructions.

PCR Amplifications for Toxin Genes.

Detection of various toxin genes was carried out by PCR amplification of each *C. perfringens* isolate. The presence of the netE, netF and netG toxin genes was detected by PCR amplification, using primers designed from the *C. perfringens* JP718 sequences. PCR-based toxin gene identification of cpa, cpb2 and cpe was also done. Primers used are described in Table 10. Amplifications were performed in a 25 μl total volume containing the following: 5 μl of template DNA; 1×PCR buffer with $Mg^{2+}$ (New England BioLabs, Pickering, ON); 0.2 mM deoxynucleoside triphosphate mixture; 2.5 units of TaqDNA polymerase (New England BioLabs); and 200 nM of each primer. The PCR program for netF was: 94° C. for 3 min, 30 cycles of 94° C. for 30 sec, 45° C. for 30 sec, extension at 72° C. for 1 min, and finally, 72° C. for 5 min. The PCR programs for netE and netG were similar with the exception of the annealing temperature, 48° C. for 30 sec/cycle. PCR product sizes were determined by agarose gel electrophoresis and visualized by ethidium bromide staining and photographed under UV light.

Prevalence of netE, netF and netG Genes in *C. perfringens* Isolates from Different Animal Species.

*Clostridium perfringens* type A isolates examined were from a collection of equine (n=84), canine (n=92), bovine (n=47), caprine (n=24) and ovine (n=28) origin. Some isolates were from cases of diarrheal disease in animals presented to the Animal Health Laboratory, University of Guelph, some of which had detailed pathological diagnostic descriptions that included cases of fatal enteritis. Other isolates were from diarrheic horses (Dr J. S. Weese, University of Guelph) or calves (Dr K. Leslie, University of Guelph). In addition, some isolates were from fatal necrotizing enteritis in foals or fatal canine hemorrhagic enteritis (Dr. T. Besser, Washington State University, Pullman, Wash.) or originated from undifferentiated diarrheal illness in dogs (Dr. R. J. Carman, TechLabs, Blacksburg, Va.; Dr. V. Perreten, Institute of Veterinary Bacteriology, University of Bern, Switzerland). Positive identifications of *C. perfringens* were based on the presence of the characteristic double zone of hemolysis and colonial morphology as well as the presence of the alpha-toxin gene cpa by PCR.

Cytotoxicity Assay and Cell Lines.

Culture supernatants of equine and canine netE, netF, and netG positive *C. perfringens* isolates were evaluated for cytotoxicity on several cell lines. Equine Ovarian cell line, EO (Dr. E. Nagy, University of Guelph); Madin Darby Bovine Kidney cell line, MDBK (ATCC, CCL-22); Madin Darby Canine Kidney cell line, MDCK (ATCC, CCL-34); Porcine Kidney cell line, PK15 (ATCC, CCL-33); Rat Fischer Fibroblast cell line, 208F (Life Technologies, ON); Mouse Embryo Fibroblast cell line, NIH 3T3 (ATCC, CRL-1658); African green monkey kidney cell line, Vero (ATCC, CCL-81); and human colon epithelial cell line, CaCo-2 (ATCC, HTB-37) were grown in EMEM complete media (EMEM 450 ml, 10% fetal calf serum [VWR International, Radnor, Pa.], 2 mM L-glutamine [Sigma-Aldrich]). The A72, a cell line derived from canine fibroblasts, was maintained in Dulbecco's Modified Eagle Medium (DMEM) supplemented with 10% fetal calf serum [VWR International], 2 mM L-glutamine [Sigma-Aldrich]. The primary chicken hepatocellular carcinoma epithelial cell line, LMH (ATCC, CRL-2117) was grown in Waymouth's complete media (90% Waymouth's MB 752/1 [Invitrogen, ON], 10% fetal calf serum). All cells were incubated at 37° C. in an atmosphere of humidified 5% $CO_2$. To test for cytotoxicity, cell lines were cultured to almost 100% confluence in 96-well plates (Corning Inc., Corning, N.Y.) grown in their respective growth medium in 5% $CO_2$ at 37° C.

For bacterial cytotoxin testing, bacterial supernatants from TPG broth cultures with an $OD_{600}$ of 0.6-0.8 were filtered through a 0.22 μm filter (Fisher Scientific). Subsequently, 100 μl of sterile bacterial culture supernatant was added to the wells, in a 2-fold dilution series up to 1:1024 (v/v) in duplicate for each strain tested. Cytotoxicity was evaluated microscopically over 8 h as described in detail in Mehdizadeh Gohari et al. (2014). *Clostridium perfringens* strains NCTC3110 (cpb-positive) and CW504 (cpa-positive) were used as positive and negative controls, respectively.

Mutation of netE, netF, and netG Toxin Genes and Conjugation:

The generation of *C. perfringens* mutants was conducted as described in Heap et al. (2007). The ClosTron intron targeting and design tool (http://clostron.com) identified possible intron target sites. The insertion sites at the positions 883/884 bp in the netE open-reading frame (ORF), at positions 152/153 bp in the netF ORF, and positions 583/584 bp in the netG ORF were preferentially chosen to generate ClosTron-intron modifications, which were obtained by PCR from primers (IBS, EBS2, EBS1 and EBS universal) designed by the ClosTron website (Table 10). The 350 bp PCR products and pMTL007 ClosTron-shuttle vector were digested with HindIII and BsrGI, ligated and then transformed by heat shock into *E. coli* DH5α. Recombinant plasmids were isolated and sequenced in order to verify sequences of the retargeted intron specific for netE, netF and netG insertions. The recombinants pMTLnetF, pMTLnetE and pMTLnetG containing the modified netE, netF and netG intron were then electroporated into electrocompetent *E. coli* CA434 for conjugation experiments. Conjugation was conducted as described in Heap et al. (2009). Plasmid transfer experiments were carried out with *E. coli* CA434 carrying recombinant plasmids pMTLnetE, pMTLnetF, and pMTLnetG, respectively. Overnight BHI cultures of the resultant

*E. coli CA*434 were used as donor strains and the equine-source *C. perfringens* JP838 strain was used as recipient. Donor and recipient cells were mixed at a ratio of 3:1 and a total of 200 μl of both cultures were spread onto BHI agar without antibiotics and incubated anaerobically at 37° C. overnight. Subsequently, the bacterial growth was removed and resuspended in 1 ml of PBS. Transconjugants were selected on BHI agar plates containing cycloserine (250 μg/ml) and thiamphenicol (15 μg/ml). Transconjugants screening were performed as described in Parreira et al. (2012). Transconjugants were confirmed by PCR amplifications of specific genes (netE, netF and netG) (Table 10).

Complementation of *C. perfringens* JP838ΔnetF:

For complementation assays, the plasmid pJIR750 was used to construct the recombinant pNetF07 which contains the entire netF gene together with the 250 bp upstream region. *Clostridium perfringens* JP838ΔnetF mutant was complemented with pNetF1A by the same conjugation method described above with *E. coli* CA434 as donor strain, using erythromycin and thiamphenicol to select transconjugants. The recombinant plasmid pNetF was also introduced into *C. perfringens* JIR325, a plasmid-less laboratory strain in order to analyze NetF expression and cytotoxicity.

Construction and Purification of Recombinant Toxins NetE, NetF and NetG Using pET-28a.

The chromosomal DNA of *C. perfringens* strain JP728 was used as a template in PCR reactions. PCR reactions were performed with a Platinum PCR SuperMix high-fidelity kit (Invitrogen) and specific primers are described in Table 10. The PCR amplified netE, netF and netG genes were cloned into the EcoRI-HindIII, EcoRI-XhoI, and BamHI-XhoI sites of vector pET-28a vector (Novagen, Gibbstown, N.J.) to generate proteins fused with histidine residues (6-His), then transformed into *E. coli* DH5α. The nucleotide sequences of the cloned PCR products were verified by sequencing. The resulting plasmids (pET28::netE, pET28::netF, pET28::netG) were introduced into *E. coli* BL21-Star (DE3) pLysS. The recombinant *E. coli* BL21 strains harboring recombinant plasmids were grown in LB medium with kanamycin (50 μg/ml) and chloramphenicol (34 μg/ml) at 37° C. until the absorbance at 600 nm reached 0.5, and then induced by adding 1 mM isopropyl-b-D-thiogalactopyranoside (IPTG) at 37° C. for 4 h. Purification of recombinant His-tagged NetE, NetF and NetG proteins from *E. coli* BL21 was performed under denaturing conditions according to the manufacturer's instructions (Qiagen). Briefly, for purification, the cell pellet was resuspended in 5 ml of lysis buffer (100 mM $NaH_2PO_4$, 10 mM Tris-Cl, 8M Urea, pH 8.0). The mixture was stirred for 60 min at room temperature. The lysate was centrifuged at 10,000×g for 30 min at room temperature to harvest the cellular debris. One ml of the 50% affinity chromatography on nickel-nitrilotriacetic acid agarose (Ni-NTA) was added to cleared lysate and mixed gently on a shaker for 60 min at 4° C. The column was washed twice with 4 ml of lysis buffer—pH 6.3, followed by 4 times with 1 ml lysis buffer—pH 5.9, and rNetE, rNetF and rNetG eluted with 4 times lysis buffer—pH 4.5. The final products were characterized by SDS-PAGE analysis.

Construction and Purification of Recombinant Toxins NetE, NetF and NetG using pET43.1a.

The PCR amplified netF gene was cloned into the EcoRI and XhoI sites of vector pET43.1a (Novagen), whereas PCR products of netE and netG genes were cloned into the EcoRI-HindIII and BamHI-XhoI sites of vector pET43.1a. Transformation into expression strain (*E. coli* BL21) and induction was done as described above. Purification of rNetE-NusA, rNetF-NusA and rNetG-NusA was done by Ni-NTA agarose under native conditions following the manufacturer's instructions (Qiagen). The resulting protein expressions and solubility levels were evaluated by SDS gel electrophoresis. Vector pET-43.1a with no insert was used to express poly-His tagged rNusA as control. rNet-NusA proteins were also tested for hemolytic activity with horse red blood cells (Yan et al., 2013). Supernatants derived from JP838 (netE, netF and netG positive strain) and CW504 (cpa positive strain) were used as controls.

Horse Immunization Using rNet-NusA Proteins.

The recombinant fusion proteins were used for polyclonal antibody production in 7 adult horses (3 horses for rNetF-NusA and 2 horses each for rNetE-NusA or rNetG-NusA). A 1:4 ratio of aluminium hydroxide gel and sterile antigen was mixed together using 2.0 mg of antigen in 2 ml PBS, for a total of 2.5 ml per horse. For the primary immunization 1.0 mg of recombinant fusion protein and for the 2 subsequent immunizations 2.0 mg of fusion protein were used. Horses were immunized intramuscularly at day 0, 14, and 28, and bled at these times as well as on day 35 and 42 after initial immunization. Horses were examined for 4 days after each immunization and body reactions to injected antigen were recorded.

Cytotoxin Neutralization by Antibodies to rNetF, rNetE and rNetG.

The neutralization of cytotoxicity by equine polyclonal antibody produced against each of the rNet-NusA proteins was performed with the EO cell line. An overnight culture supernatant of a netE, netF and netG-positive strain (JP728) was prepared as described above. The supernatant was diluted in EMEM medium; the dilution of supernatant used for determination of neutralization titers was 128. Subsequently, serial 2-fold dilutions of sera up to 1:102,400 were made in a new 96-well plate (100 μl/well). Diluted antibodies were transferred into the diluted toxin plate and manually homogenized for 30 sec, then incubated for 2 h at 37° C. After incubation, 100 μl of the toxin-antibody dilution series was added into a plate with confluent EO cells which was incubated in a humidified environment of 5% $CO_2$ at 37° C. for 8 h. The neutralizing antibody titer was that showing an inhibition of 2+ or greater (Roth et al., 1999).

Enzyme-Linked Immunosorbent Assay (ELISA).

rNetE, rNetF and rNetG separated by SDS-PAGE were recovered by electro-elution using the Bio-Rad model 422 electro-eluter according to manufacturer's protocol. Briefly, recombinant proteins were electrophoresed on a 12% polyacrylamide gel and the zone with rNet protein was cut from the gel, macerated into small pieces and then placed in electro-elution tubes containing electrophoretic buffer (25 mM Tris base, 192 mM Glycine and 0.1% SDS). Transferred recombinant proteins underwent dialysis to remove SDS.

For ELISA, 96-well plates (MaxiSorp, Nunc, Roskilde, Denmark) were coated with 0.5 μg/well of individual electro-eluted rNet proteins in carbonate-bicarbonate buffer pH 9.6 for 1 h at 37° C. followed by overnight incubation at 4° C. (Kircanski et al., 2012a). Briefly, plates were washed twice with buffer (phosphate-buffered saline pH 7.4 (PBS), 0.05% Tween 20) and once with PBS, and the coated plates were blocked using blocking buffer (PBS, 0.05% Tween 20, 0.5% fish skin gelatin [Norland HiPure Liquid Gelatin, Norland Products Inc, Cranbury, N.J.]) for 2 h at 37° C. After washing 3 times with wash buffer, 100 μl/well of horse polyclonal serum (2-fold serial dilutions up to 1:409600) were added to the plate in duplicate. Washing buffer with no polyclonal antibodies was used as a negative control. After incubation at room temperature for 2 h, followed by 3 times washings with washing buffer, 100 μl/well of enzyme-labeled detecting goat anti-horse antibody (Jackson ImmunoResearch Laboratories Inc., West Grove, Pa.) (diluted 1:5000 in wash buffer) was applied, and the plate was incubated for another 1 h at room temperature. The plate was then washed 3 times with wash buffer and 100 μl/well of the chromogenic substrate 2,2'-azino-di-[3-ethylbenzthiazoline sulfonate]diammonium salt (ABTS) (Roche Applied Science) was added. The reaction was stopped after 30 min to 1 h of further incubation at room temperature using 0.5%

SDS (50 μl/well) and the OD measured at 405 nm in an ELISA reader (BioTek Instruments Inc., Power Wave XS, Winooski, Vt.).

Western Blot Analysis.

Western immunoblotting was used to assess the specificity of horse polyclonal serum prepared against rNet proteins. For this purpose, 2 type B *C. perfringens* (NCTC3110, NCTC7368), two type C *C. perfringens* (ATCC3628, NCTC3181), and 2 netB-positive *C. perfringens* strains (CP1, CP4) were tested. Broth culture supernatants were mixed with a 1:1 ratio of Laemmli Sample Buffer (Bio-Rad) and separated by SDS-PAGE in 12% acrylamide gel. Subsequently, proteins were transferred onto a nitrocellulose 0.45 μm membranes (BioTrace NT, Gelman Laboratory, Laurent, QC) for 60 min at constant power supply of 95 V. Membranes were then placed in blocking buffer (PBS, 0.05% Tween 20, 0.5% fish skin gelatin) at 4° C. overnight, followed by incubation with serum from horses immunized with 1 of the 3 rNet-NusA proteins at 1:2000 dilution, for 90 min at room temperature. After washing 3 times, the membranes were incubated with alkaline phosphatase-conjugated goat anti-horse IgG (Jackson ImmunoResearch Laboratories) at 1:5000 dilution. Specific protein bands were visualized using the alkaline phosphatase conjugate substrate kit (Bio-Rad) (Kircanski et al., 2012b). BLUeye Prestained Protein Ladder (FroggaBio, ON) was used in Western blot analysis.

Pulse Field Gel Electrophoresis (PFGE):

PFGE was performed to analyze the presence of plasmids in 12 *C. perfringens* isolates (6 canine isolates and 6 equine isolates), as described by Parreira et al. (2012), and on chromosomal DNA to examine the clonality of 35 equine (16 netF+, 19 netF−) and 35 canine (16 netF+, 19 netF−) *C. perfringens* isolates, using the method described by Chalmers et al. (2008). Thirty-two isolates were selected on the basis of the presence of the netF gene, and thirty-eight isolates were randomly selected from fecal isolates from diarrheal or healthy animals that were negative for the netF gene. Electrophoresis was performed in a 1% PFGE-certified gel and separated with the CHEF-III PFGE system (Bio-Rad) in 0.56 Tris-borate-EDTA buffer supplemented with 200 μM thiourea (Fisher Scientific) at 14° C. at 6 V for 19 h with a ramped pulsed time of 1 to 12 sec (plasmid protocol) and 4 to 38 sec (clonality protocol). As a size guide, *C. perfringens* strain 33 were electrophoresed on each gel, with markers being used in lanes 1, 2, 7 and 15. Gels were stained in ethidium bromide and visualized by UV light. Mid-Range II PFG markers (New England Biolabs) were used as the molecular DNA ladder.

Band matching was performed using a 0.8% position tolerance; cluster analysis was completed utilizing the Dice similarity coefficient and unweighted pair group method with arithmetic mean. The isolate host species (equine or canine), laboratory numeric code, and presence of netF (+ or −) were included. Genotypes were designated through application of the Tenover criteria (Tenover et al., 1995) with 60% band pattern similarity equating to a 7-band difference. These genotypes were labelled alphabetically from top to bottom, with a subscript representing the percent relatedness of the banding pattern. Analysis of the PFGE gels was completed utilizing BioNumerics software version 7.1 (Applied Maths, Austin, Tex.).

Preparation of DIG Probes and Plasmid PFGE for Southern Blotting.

DNA probes for all plasmid PFGE Southern blot steps were labelled by PCR amplification in the presence of digoxigenin-11-dUTP (DIG; Roche Applied Science) according to the manufacturer's recommendation. DNA probes were amplified from *C. perfringens* strain JP718. DNA probes for netE and cpe genes were prepared with specific primers (Table 10). DNA from PFGE gels was transferred to nylon membranes (Roche Applied Science, Mannheim, Germany). DNA hybridizations and detection were performed by using the DIG labelling and CSPD substrate according to the manufacturer's recommendation (Roche Applied Science). For Southern blot hybridizations, nylon membranes were prehybridized for at least 2 h at 42° C. in hybridization solution without labelled probe and then hybridized separately at 42° C. with specific DNA probes for 16 h. The membranes were washed at 68° C. under high-stringency conditions. For each different DIG labelled probe, the membrane was first stripped with 0.2 N NaOH and 0.1% sodium dodecyl sulfate, incubated with prehybridization solution, and then reprobed.

Nucleotide Sequence Accession Numbers.

The net toxin sequences were assigned GenBank accession numbers KJ606985 for netE, KJ606986 for netF and KJ606987 for netG.

Statistical Analyses.

Fisher's exact test was used to make Odds Ratio estimates about the association of netF with canine hemorrhagic gastroenteritis or foal necrotizing enteritis, since the test uses the hypergeometric distribution that allows us to make exact statements. Conditional means likelihood estimates (CMLE) of Odd Ratios were obtained, with 95% confidence intervals, except where one of the cell counts was 0, in which case mean unbiased estimates (MUE) were determined (Hirji et al., 1989).

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Tables

TABLE 1

Characterization of Net toxins.

| Protein[1] | Length (aa) | Molecular size (mature protein) in kDa | Predicted Product | E-Value | % of Identity[2] | Localization[3] | Conserved Domain | Accession | PSSM-ID | SignalP[4] |
|---|---|---|---|---|---|---|---|---|---|---|
| NetE | 322 | 36.1 (32.9) | Leukocidin | 3.14E−71 | 254/322(79%) | Extracellular | Leukocidin/Hemolysin toxin family | cl08468 | 244969 | 30-31 |

TABLE 1-continued

Characterization of Net toxins.

| Protein[1] | Length (aa) | Molecular size (mature protein) in kDa | Predicted Product | E-Value | % of Identity[2] | Localization[3] | Conserved Domain | Accession | PSSM-ID | SignalP[4] |
|---|---|---|---|---|---|---|---|---|---|---|
| NetF | 305 | 34.3 (31.7) | Leukocidin | 4.41E−57 | 143/299(48%) | Extracellular | Leukocidin/ Hemolysin toxin family | cl08468 | 244969 | 24-25 |
| NetG | 306 | 34.3 (31.7) | Leukocidin | 2.89E−70 | 143/276(52%) | Extracellular | Leukocidin/ Hemolysin toxin family | cl08468 | 244969 | 24-25 |

[1]Based on strain JP718 genome
[2]Percent amino acid identity (Query length/total length of the subject protein)
[3]Subcellular location as predicted by pSortb
[4]Signal peptide was predicted by SignalP cleavage position

TABLE 2

Cytotoxicity of different cell lines with bacterial culture supernatant of netF-positive (JP726, JP728) and cpb-positive (NCTC3110) *C. perfringens* strains.

| Cell lines[1] | Origin of cell lines | Cytotoxicity[2] NCTC3110 | JP728 (Equine) | JP726 (Canine) |
|---|---|---|---|---|
| EO | Equine | 16 | 128 | 128 |
| MDCK | Canine | N[3] | 4 | 4 |
| A72 | Canine | 4 | 8 | 8 |
| MDBK | Bovine | N | 2 | 2 |
| PK15 | Pig | N | 4 | 4 |
| 208F | Rat | 2 | 2 | 2 |
| NIH 3T3 | Mouse | N | N | N |
| CaCo2 | Human | N | 2 | 2 |
| LMH | Chicken | 2 | N | N |
| Vero | Monkey | N | N | N |

[1]EO: Equine ovarian cell line, MDCK: Madin Darby canine kidney cell line, A72: Canine fibroblasts cell line, MDBK: Madin Darby bovine kidney cell line, PK15: Porcine kidney cell line, 208F: Rat Fischer fibroblast cell line, NIH 3T3: Mouse embryo fibroblast cell line, CaCo2: Human colon epithelial cell line, LMH: Primary chicken hepatocellular carcinoma epithelial cell line, Vero: African green monkey kidney cell line
[2]Cytotoxicity was evident after 8 h of exposure of 2-fold dilution series of the filter-sterilized culture supernatants up to 1:1024 to different cells
[3]No cytotoxicity

TABLE 3

Cytotoxicity of equine ovarian cell line (EO) with different bacterial culture supernatants.

| Strains (toxin genes)[1] | Supernatant dilutions[2] 1:2 | 1:4 | 1:8 | 1:16 | 1:32 | 1:64 | 1:128 | 1:256 |
|---|---|---|---|---|---|---|---|---|
| NCTC3110 (cpb+) | 4+[3] | 4+ | 4+ | 2+ | N[4] | N | N | N |
| JP564 (cpe+/cpb2+) | 4+ | 4+ | 3+ | N | N | N | N | N |
| SM101 (cpe+) | 4+ | 2+ | N | N | N | N | N | N |
| JP728 (netE/F/G+) | 4+ | 4+ | 4+ | 4+ | 4+ | 4+ | 2+ | N |
| JP718 (netE/F/G+) | 4+ | 4+ | 4+ | 4+ | 4+ | 4+ | 2+ | N |
| CW504 (cpa+) | N | N | N | N | N | N | N | N |
| TPG broth control | N | N | N | N | N | N | N | N |

[1]NCTC3110: type B, JP564: type A, SM101: Derivative of NCTC 8798, JP728: equine necrotizing enteritis, JP718: canine hemorrhagic enteritis, CW504: lab strain
[2]Filtered-sterilized bacterial supernatants from TPG broth cultures with an $OD_{600}$ of 0.6-0.8
[3]Cytotoxicity end-point is 2+
[4]No cytotoxicity

TABLE 4

Bacterial strains used.

| Strain | Name | Relevant characteristics | Source |
|---|---|---|---|
| *C. perfringens* | NCTC3110 | Type B | NCTC, UK |
| | NCTC7368 | Type B | NCTC, UK |
| | NCTC3181 | Type C | NCTC, UK |
| | ATCC3628 | Type C | ATCC, USA |
| | SM101 | Derivative of NCTC 8798 | J. Gong, AAFC |
| | CW504 | $Rif^{R2}$ $Nal^{R}$; conjugation recipient | J. I. Rood, Monash University |
| | JIR325 | Strain 13 $Rif^{R}Nal^{R}$; electroporation recipient | J. I. Rood, Monash University |
| | Strain 33 | *C. perfringens* strain 33 was used to normalize the gel and allow for gel-to-gel comparisons | This study |
| | CP1 | netB+ *C. perfringens*/Chicken necrotic enteritis | (Thompson et al., 2006) |
| | CP4 | netB+ *C. perfringens*/Chicken necrotic enteritis | (Thompson et al., 2006) |
| | JP55 | Equine strain/Undifferentiated diarrheal disease | This study |
| | JP60 | Equine strain/Undifferentiated diarrheal disease | This study |
| | JP134 | Canine strain/Undifferentiated diarrheal disease | This study |
| | JP564 | Human strain/Type A | This study |
| | JP718 | Canine strain/Hemorrhagic gastroenteritis | This study |
| | JP726 | Canine strain/Hemorrhagic gastroenteritis | This study |
| | JP728 | Equine strain/Necrotizing enteritis | This study |
| | JP738 | Canine strain/Undifferentiated diarrheal disease | This study |

TABLE 4-continued

Bacterial strains used.

| Strain | Name | Relevant characteristics | Source |
|---|---|---|---|
| | JP771 | Canine strain/Hemorrhagic gastroenteritis | This study |
| | JP799 | Equine strain/Necrotizing enteritis | This study |
| | JP810 | Canine strain/Hemorrhagic gastroenteritis | This study |
| | JP826 | Canine strain/Hemorrhagic gastroenteritis | This study |
| | JP833 | Equine strain/Necrotizing enteritis | This study |
| | JP838 | Equine strain/Hemorrhagic enterocolitis | This study |
| | JP838E-05 | JP838ΔnetE::ErmRAM - ClosTron insertion in netE gene | This study |
| | JP838E-05 | JP838ΔnetF::ErmRAM - ClosTron insertion in netF gene | This study |
| | JP838G-07 | JP838ΔnetG::ErmRAM - ClosTron insertion in netG gene | This study |
| | T504-05ΔnetE | CW504 derived transconjugant $Rif^RNal^RErm^R$ with plasmid pNetE/NetF from JP838E-05 | This study |
| | JPnetF | JIR325 derived transconjugant $Rif^RNal^RErm^R$ with plasmid pNetF07 from JP838E-05 | This study |
| | VN-22C | JP838F-05 $Erm^RCm^R$ complemented with pNetF07 | This study |
| *E. coli* | DH5α | $F^-$Φ80 lacZΔM15Δ (lacZYA-argF)U169 endA1 recA1 hsdr17($r_K^-m_K^-$) deoR thi-1 supE44 gyrA96 relA1 | Stratagene, La Jolla, CA |
| | BL21-Star (DE3) pLysS | *E. coli* B $F^-$ dcm omPT hsdS ($r_B^-m_B^-$) gal λ(DE3) [pLysS Cam] | Invitrogen |
| | CA434 | *E. coli* HB101 carrying the Incβ conjugative plasmid R702 | (Purdy et al., 2002) G. Vedantam, University of Arizona |
| | CA434-netE | *E. coli* CA434 carrying plasmid pMTL::netE | This study |
| | CA434-netF | *E. coli* CA434 carrying plasmid pMTL::netF | This study |
| | CA434-netG | *E. coli* CA434 carrying plasmid pMTL::netG | This study |

TABLE 5

Features of type A canine and equine *Clostridium perfringens* strains.

| | Plasmid | PCR[1] | | | Southern blot[2] | |
|---|---|---|---|---|---|---|
| Strains | number | netE, netF | netG | cpe | netE | cpe |
| JP134 | 1 | − | − | + | − | 70 |
| JP718 | 3 | + | + | + | 75 | 45 |
| JP726 | 3 | + | + | + | 75 | 48 |
| J771 | 3 | + | − | + | 75 | 50 |
| JP810 | 2 | + | + | + | 75 | 48 |
| JP826 | 2 | + | + | + | 75 | 48 |
| JP55 | 3 | + | − | + | 75 | 50 |
| JP60 | 3 | + | − | + | 75 | 50 |
| JP728 | 2 | + | + | + | 75 | 48 |
| JP738 | − | − | − | − | − | − |
| JP799 | 2 | + | + | + | 75 | 48 |
| JP833 | 2 | + | − | + | 75 | 48 |

[1]Genes detected by PCR amplification (−) negative and (+) positive

[2]Approximate size of plasmids in kb

TABLE 6

ELISA cross-reactivity and cytotoxin neutralizing titers to recombinant toxins rNetE, rNetF and rNetG in horses immunized with different rNet-NusA proteins.

| | | Neutralizing anti-serum | ELISA | | | |
|---|---|---|---|---|---|---|
| Horses[1] | Antigens | titers[2] | rNetE | rNetF | rNetG | rNetB |
| 1 | rNetE | 64[3] | 102400 | 6400 | 12800 | 51200 |
| 2 | | 128 | 25600 | 1600 | 1600 | 12800 |
| 3 | rNetF | 25600 | 12800 | 204800 | 12800 | 6400 |
| 4 | | 6400 | 6400 | 102400 | 12800 | 12800 |
| 5 | | 3200 | 12800 | 204800 | 12800 | 6400 |
| 6 | rNetG | 64 | 6400 | 12800 | 51200 | 12800 |
| 7 | | 128 | 51200 | 51200 | 102400 | 51200 |

[1]Immunization: Horses 1, 2, rNetE-NusA; horses 3-5, rNetF-NusA; horses 6, 7, rNetG-NusA

[2]The neutralization of cytotoxicity by polyclonal antibody was performed with the EO cell line

[3]The neutralizing antibody titer was that showing an inhibition of 2+ or greater

TABLE 7

Plasmids used in this study.

| Plasmid | Relevant characteristics | Source |
|---|---|---|
| pJIR750 | *E. coli* - *C. perfringens* shuttle vector, $Cm^R$ | J. I. Rood, Monash University |
| pNetF07 | pJIR750$Cm^R$ containing netF gene and 250 bp of its upstream region | This study |
| pMTL007 | Inducible clostridial expression vector for expression of ClosTron, containing Erm RAM, ColE1, pCB102, $Cm^R$ | (Heap et al., 2007) |

TABLE 7-continued

Plasmids used in this study.

| Plasmid | Relevant characteristics | Source |
|---|---|---|
| pMTLnetE | pMTL007 containing intron retargeted to *C. perfringens* netE (sense insertion at 883-884 bp) | This study |
| pMTLnetF | pMTL007 containing intron retargeted to *C. perfringens* netF (antisense insertion at 152-153 bp) | This study |
| pMTLnetG | pMTL007 containing intron retargeted to *C. perfringens* netG (antisense insertion at 583-584 bp) | This study |
| pET-28a | *E. coli* expression vector. $P_{T7}$, $Kan^R$, ori pBR322, ori f1, lacI, T7, Tag N-terminal 6xHis, C-terminal 6xHis | (Novagen Gibbstown, NJ) |
| pET28::netE | pET28a containing the DNA fragment amplified by PCR using primers netE-F-EcoRI and netE-R-HindIII | This study |
| pET28::netF | pET28a containing the DNA fragment amplified by PCR using primers netF-F-EcoRI and netF-R-XhoI | This study |
| pET28::netG | pET28a containing the DNA fragment amplified by PCR using primers netG-F-BamHI and netG-R-XhoI | This study |
| pET43.1a | *E. coli* expression vector. $P_{T7}$, $Amp^R$, ori pBR322, ori f1, lacI, T7, Tag N-terminal Nus, C-terminal 6xHis | (Novagen, Gibbstown, NJ) |
| pET43::netE | pET43.1a containing the DNA fragment amplified by PCR using primers netE-F-EcoRI and netE-R-HindIII | This study |
| pET43::netF | pET43.1a containing the DNA fragment amplified by PCR using primers netF-F-EcoRI and netF-R-XhoI | This study |
| pET43::netG | pET43.1a containing the DNA fragment amplified by PCR using primers netG-F-BamHI and netG-R-XhoI | This study |

TABLE 8

Summary of partial sequences of scaffold00006 and scaffold00012 from *C. perfringens* typeA strain JP718.

| Scaffold | start-stop | strand | aa | predicted product | hit description | % Identity |
|---|---|---|---|---|---|---|
| 00006 | 138803-138159 | − | 214 | Mobile element protein | integrase catalytic subunit [*Clostridium botulinum* BKT015925] | 93/162(57%) |
| 00006 | 139105-138800 | − | 101 | Mobile element protein | transposase [*Clostridium perfringens*] | 87/102(85%) |
| 00006 | 140777-139809 | − | 322 | Panton-Valentine leukocidin chain S precursor | necrotic enteritis toxin B precursor [*Clostridium perfringens*] | 254/322(79%) |
| 00006 | 141216-141995 | + | 259 | hypothetical protein | hypothetical protein [*Clostridium botulinum*] | 19/41(46%) |
| 00006 | 142255-142683 | + | 142 | hypothetical protein | hypothetical protein [*Clostridium perfringens*] | 95/136(70%) |
| 00006 | 143946-144473 | + | 175 | Signal peptidase I (EC 3.4.21.89) | signal peptidase [*Clostridium perfringens*] | 146/175(83%) |
| 00006 | 144666-144508 | − | 52 | hypothetical protein | hypothetical protein [*Clostridium perfringens*] | 40/52(77%) |
| 00006 | 148122-147964 | − | 52 | hypothetical protein | hypothetical protein [*Clostridium perfringens*] | 50/51(98%) |
| 00006 | 149218-149454 | + | 78 | hypothetical protein | hypothetical protein pCpb2-CP1_46 [*Clostridium perfringens*] | 73/78(94%) |
| 00006 | 149916-150842 | + | 308 | hypothetical protein | hypothetical protein pCpb2-CP1_47 [*Clostridium perfringens*] | 302/308(98%) |
| 00006 | 151318-151524 | + | 68 | hypothetical protein | hypothetical protein [*Clostridium perfringens*] | 44/53(83%) |
| 00006 | 152227-154152 | + | 641 | Histidine kinase | sensory box histidine kinase [*Clostridium perfringens*] | 404/644(63%) |
| 00006 | 154804-155721 | + | 305 | Panton-Valentine leukocidin chain S precursor | necrotic enteritis toxin B precursor [*Clostridium perfringens*] | 143/299(48%) |
| 00006 | 156097-156210 | + | 37 | Mobile element protein | transposase [*Clostridium perfringens*] | 15/34(44%) |
| 00006 | 156278-156703 | + | 141 | Mobile element protein | integrase catalytic subunit [*Clostridium botulinum*] | 51/122(42%) |
| 00012 | 9399-10319 | − | 306 | Panton-Valentine leukocidin chain S precursor | necrotic enteritis toxin B precursor [*Clostridium perfringens*] | 143/276(52%) |
| 00012 | 10698-10528 | − | 52 | hypothetical protein | hypothetical protein [*Clostridium perfringens*] | 42/52(81%) |
| 00012 | 10789-10667 | + | 40 | hypothetical protein | hypothetical protein pNetB-NE10_42 [*Clostridium perfringens*] | 23/29(79%) |
| 00012 | 10886-11119 | − | 77 | Mobile element protein | transposase [*Clostridium kluyveri* DSM 555] | 49/77(64%) |
| 00012 | 11517-11813 | − | 98 | Mobile element protein | transposase IS4 family protein [*Thermoanaerobacter ethanolicus*] | 47/97(48%) |
| 00012 | 53372-53695 | + | 107 | Transcriptional Regulator | PadR family transcriptional regulator [*Clostridium perfringens*] | 107/107(100%) |

TABLE 8-continued

Summary of partial sequences of scaffold00006 and scaffold00012 from *C. perfringens* typeA strain JP718.

| Scaffold | start-stop | strand | aa | predicted product | hit description | % Identity |
|---|---|---|---|---|---|---|
| 00012 | 53699-54340 | + | 213 | hypothetical protein | hypothetical protein pCP8533etx_p48 [*Clostridium perfringens*] | 213/213(100%) |
| 00012 | 55052-54351 | − | 233 | Beta2 toxin | Beta2 toxin [*Clostridium perfringens*] | 232/233(99%) |
| 00012 | 55240-55419 | − | 59 | hypothetical protein | hypothetical protein pBeta2_00080 [*Clostridium perfringens*] | 59/59(100%) |
| 00012 | 55531-55403 | − | 42 | hypothetical protein | hypothetical protein [*Clostridium perfringens*] | 40/42(95%) |
| 00012 | 56336-55677 | + | 219 | Mobile element protein | putative resolvase [*Clostridium perfringens*] | 217/219(99%) |
| 00012 | 57067-56612 | − | 151 | hypothetical protein | hypothetical protein [*Bacillus cereus*] | 61/146(42%) |
| 00012 | 57720-57070 | − | 216 | hypothetical protein | hypothetical protein [*Bacillus cereus*] | 102/219(47%) |
| 00012 | 58121-57876 | − | 81 | hypothetical protein | hypothetical protein pCPF4969_37 [*Clostridium perfringens* CPE str. F4969] | 79/81(98%) |
| 00012 | 61130-59481 | − | 549 | hypothetical protein | hypothetical protein pCPF4969_36 [*Clostridium perfringens* CPE str. F4969] | 540/549(98%) |
| 00012 | 62385-61528 | − | 285 | hypothetical protein | hypothetical protein [*Clostridium perfringens*] | 284/284(100%) |
| 00012 | 67198-65777 | − | 473 | Mobile element protein | IS1151-like transposase [*Clostridium perfringens*] | 472/473(99%) |
| 00012 | 68474-67515 | − | 319 | enterotoxin | enterotoxin [*Clostridium perfringens*] | 319/319(100%) |
| 00012 | 68834-69049 | − | 71 | hypothetical protein | conserved hypothetical protein [*Clostridium perfringens*] | 71/71(100%) |
| 00012 | 70181-69726 | − | 151 | Mobile element protein | IS1469-like transposase [*Clostridium perfringens* CPE str. F4969] | 151/151(100%) |

TABLE 9

Presence of VirR box upstream Net genes.

| scaffold | Gene | Orientation | Distance (bp) | VirR box | SEQ ID NO: |
|---|---|---|---|---|---|
| 00006 | netE | - | 300 | c*CCAGTTT*TACACGAATTT*TGACCAGTTA*T*GTA* | 43 |
| 00006 | netF | + | - | - | |
| 00012 | netG | + | 487 | a*CCAGTTA*T*G*TA*TA*TATTT*TGACCAGT*TT*TACA* | 44 |
| Consensus VirR box (Cheung et al., 2004) italicized | | | | c*CCA*n*TT*n*T*ncatnannnn*TG*n*CCAGTT*n*T*n*CA*c | 45 |

TABLE 10

Primers

| Primer names | 5'-3' | PCR size (bp) | Ref | SEQ ID NO: |
|---|---|---|---|---|
| PCR | | | | |
| Ext-netE-F | AATTCAGTATATTCACATGCAG | 1026 | | 13 |
| Ext-netE-R | CAGTTATACCGATTGTATTAGA | | | 14 |
| netE-F | TAGAAAACGTTCAATTGTATGG | 601 | | 15 |
| netE-R | AGAAAGCGCTGATACAGCTAATAAA | | | 16 |
| netF-F | AACAATATGTACAGGTATAACT | 862 | | 9 |
| netF-R | TTGATAGGTATAATATGGTTCT | | | 10 |
| netG-F | TTGTTCAGGATTAGTAGCATTA | 860 | | 11 |
| netG-R | CATGAGTTGCATAAGTTGGTGT | | | 12 |
| alpha-toxin-F | GCTAATGTTACTGCCGTTGA | 325 | (Nowell et al., 2010) | 17 |
| alpha-toxin-R | CCTCTGATACATCGTGTAAG | | | 18 |
| beta2-F | ATTATGTTTAGGAATACAGTTA | 741 | (Jost et al., 2005) | 19 |
| beta2-R | CAATACCCTTCACCAAATACTC | | | 20 |

TABLE 10-continued

| Primers | | | | |
|---|---|---|---|---|
| Primer names | 5'-3' | PCR size (bp) | Ref | SEQ ID NO: |
| enterotoxin-F | GGAGATGGTTGGATATTAGG | 223 | | 21 |
| enterotoxin-R | GGACCAGCAGTTGTAGATA | | | 22 |
| Mutation | | | | |
| NetE-IBS | AAAAAAGCTTATAATTATCCTTAAACGTCCAACT GGTGCGCCCAGATAGGGTG | 350 | | 23 |
| NetE-EBS-1d | CAGATTGTACAAATGTGGTGATAACAGATAAGT CCAACTGCATAACTTACCTTTCTTTGT | | | 24 |
| NetE-EBS-2 | TGAACGCAAGTTTCTAATTTCGGTTACGTTCCGA TAGAGGAAAGTGTCT | | | 25 |
| NetF-IBS | AAAAAAGCTTATAATTATCCTTAGTCTTCATACC AGTGCGCCCAGATAGGGTG | 350 | | 26 |
| NetF-EBS-1d | CAGATTGTACAAATGTGGTGATAACAGATAAGT CATACCATCTAACTTACCTTTCTTTGT | | | 27 |
| NetF-EBS-2 | TGAACGCAAGTTTCTAATTTCGATTAAGACTCGA TAGAGGAAAGTGTCT | | | 28 |
| NetG-IBS | AAAAAAGCTTATAATTATCCTTATCCTACCATAA CGTGCGCCCAGATAGGGTG | 350 | | 29 |
| NetG-EBS-1d | CAGATTGTACAAATGTGGTGATAACAGATAAGT CCATAACCATAACTTACCTTTCTTTGT | | | 30 |
| NetG-EBS-2 | TGAACGCAAGTTTCTAATTTCGGTTTAGGATCGA TAGAGGAAAGTGTCT | | | 31 |
| EBS-Universal | CGAAATTAGAAACTTGCGTTCAGTAAAC | | | 32 |
| Recombinant Protein | | | | |
| RecNetE-F (EcoRI) | CCGCGAATTCTCTACTAGTTTAGCTCTTGCAAG | 957 | | 33 |
| RecNetE-R (HindIII) | CCGCAAGCTTTAGAAAACGTTCAATTGTATGG | | | 34 |
| RecNetF-F (EcoRI) | CCGCGAATTCAATTCCTTTCCTGAAAGTATTA | 863 | | 35 |
| RecNetF-R (XhoI) | CCGCCTCGAGGTATATAAATTCTACAGTATGA | | | 36 |
| RecNetG-F (BamHI) | CCGCGGATCCGCTACGTTGCCAGAAATTATTG | 866 | | 37 |
| RecNetG-R (XhoI) | CCGCCTCGAGATATTTAAATGTTACTTTATGG | | | 38 |
| SB probes | | | | |
| probeNetE-F | CCTTCAACAGATATATTTCCTCCAA | 419 | | 39 |
| probeNetE-R | ACACAAACTCAAGTGTTTGCAAGT | | | 40 |
| probeCpe-F | GGAGATGGTTGGATATTAGG | 300 | | 41 |
| probeCpe-R | GGACCAGCAGTTGTAGATA | | | 42 |

TABLE 11

| Table of Sequences |
|---|
| NetF nucleotide sequence |
| SEQ ID NO: 1 |
| atgaaaaaaacaatatgtacaggtataactatattttattattattaggg |
| aatattacacaagtaaaagctaattcattcctgaaagtattattaactca |
| aaaggtaaacaagctgaggtttatacatcatcagatgcttctgaaagaga |
| tggtataaagacatctttatcagcatcatttattgaagatccaaacagta |
| ataacttaacagctcttgtttctttaaaaggatttataccttctggatta |
| attaaaacaggaacttattacagtgcaaatatgtattggccaagtaagta |
| taatataaatattgaaactactgatgaaaaaaataatgttaaaattttag |
| aaagcattccaagtaatacgatagaaacagtaagagtaactgaaagtatg |
| ggttatagtattggtggaaatgtttccgttagtaaaaagtcatcttcagt |
| tggagcaaatgctggttttaatgttcaacgttcagtacaatatgagcaac |

TABLE 11-continued

| Table of Sequences |
|---|
| ctgatttcaagacgatacagaaatctgatggaattaggaaggatatggaa |
| catagtgtttaacaagacaaaagatggatatgaccaaaattcgtatcatg |
| ctctatatggcaatcaattatttatgaaatctaggttacataatacaggt |
| gcaaaaaatttagttgaagataaagatttatcaccattaatttctggtgg |
| gttcactcctaatatggtaattgctcttaaggcaccaaaaggcacaaaaa |
| aatcaatgattaatttaaactataacttatatcaagatttatatacttta |
| gagtggtataaaacccaatggtggggagaaaatcgtgttgcaaaagaacc |
| atattatacctatcaaacatatgaacttgattgggagaatcatactgtag |
| aatttatatactaa |

TABLE 11-continued

Table of Sequences

NetG nucleotide sequence

SEQ ID NO: 2 ttgagaagattgttttgttcaggattagtagcattaaccttaataacagg aaatatttcatatgtaagagcagctacgttgccagaaattattgaatcaa atggtaaaaaagcagagctttatacttcttcagatgcaaatgatacgaat gatgtaaaaacttctatatcagcatcatttattgaagatgaacatgatag taatttgactgcacttattaatttaaaaggatttattccatctaaactta taaaaacaggggattattatcatggaagaatggattggccaagcaaatat aggatatctgttttgtcagtagattataatgataatgaagaagtaaagat tatagaaagtattccgagtaataaaatagaaactatacaagtaagtgaaa gtataggatatactgttggtggagaaatatcagctaacaaagagtcagct tctggtggattaaatgctaactatagtgtacaacgttctatttcttatga acagccagactttaaaacagttaaaaaatctgatagtactaaagctgctt catgggatgtagtttttaattgtaataaagatggttatgataggaattct catcacccattttatggaaatcaattatttatgaaatctagattatataa tacaggaattaataatttaactgataataaagatttatcaacattaattt caggtggattttctcctaatatggcagttgctataaagcaccaaaaggta cgaaaaaatcacagatattttaagttatcaaacttatcatgatttatata agctagattggactggaactgaatggtggggttcaaatcaccaagctaaa acaccaacttatgcaactcatgcttatgaaattgattgggagaaccataa agtaacatttaaatattaa NetF amino acid sequence

SEQ ID NO: 3

MKKTICTGITIFSLLLGNITQVKANSFPESIINSKGKQAEVYTSSDASER

DGIKTSLSASFIEDPNSNNLTALVSLKGFIPSGLIKTGTYYSANMYWPSK

YNINIETTDEKNNVKILESIPSNTIETVRVTESMGYSIGGNVSVSKKSSS

VGANAGFNVQRSVQYEQPDFKTIQKSDGIRKASWNIVFNKTKDGYDQNSY

HALYGNQLFMKSRLHNTGAKNLVEDKDLSPLISGGFTPNMVIALKAPKGT

KKSMINLNYNLYQDLYTLEWYKTQWWGENRVAKEPYYTYQTYELDWENHT

VEFIY

NetG amino acid sequence

SEQ ID NO: 4

MRRLFCSGLVALTLITGNISYVRAATLPEIIESNGKKAELYTSSDANDTN

DVKTSISASFIEDEHDSNLTALINLKGFIPSKLIKTGDYYHGRMDWPSKY

RISVLSVDYNDNEEVKIIESIPSNKIETIQVSESIGYTVGGEISANKESA

SGGLNANYSVQRSISYEQPDFKTVKKSDSTKAASWDVVFNCNKDGYDRNS

HHPFYGNQLFMKSRLYNTGINNLTDNKDLSTLISGGFSPNMAVALKAPKG

TKKSQLILSYQTYHDLYKLDWTGTEWWGSNHQAKTPTYATHAYEIDWENH

KVTFKY

NetF-NusA recombinant protein

SEQ ID NO: 5

MNKEILAVVEAVSNEKALPREKIFEALESALATATKKKYEQEIDVRVQID

RKSGDFDTFRRWLVVDEVTQPTKEITLEAARYEDESLNLGDYVEDQIESV

TFDRITTQTAKQVIVQKVREAERAMVVDQFREHEGEIITGVVKKVNRDNI

SLDLGNNAEAVILREDMLPRENFRPGDRVRGVLYSVRPEARGAQLFVTRS

KPEMLIELFRIEVPEIGEEVIEIKAAARDPGSRAKIAVKTNDKRIDPVGA

CVGMRGARVQAVSTELGGERIDIVLWDDNPAQFVINAMAPADVASIVVDE

DKHTMDIAVEAGNLAQAIGRNGQNVRLASQLSGWELNVMTVDDLQAKHQA

EAHAAIDTFTKYLDIDEDFATVLVEEGFSTLEELAYVPMKELLEIEGLDE

PTVEALRERAKNALATIAQAQEESLGDNKPADDLLNLEGVDRDLAFKLAA

RGVCTLEDLAEQGIDDLADIEGLTDEKAGALIMAARNICWFGDEATSGSG

HHHHHHSAGKETAAAKFERQHMDSPPPTGLVPRGSAGSGTIDDDDKSPGA

RGSEFNSFPESIINSKGKQAEVYTSSDASERDGIKTSLSASFIEDPNSNN

LTALVSLKGFIPSGLIKTGTYYSANMYWPSKYNINIETTDEKNNVKILES

IPSNTIETVRVTESMGYSIGGNVSVSKKSSSVGANAGFNVQRSVQYEQPD

FKTIQKSDGIRKASWNIVFNKTKDGYDQNSYHALYGNQLFMKSRLHNTGA

KNLVEDKDLSPLISGGFTPNMVIALKAPKGTKKSMINLNYNLYQDLYTLE

WYKTQWWGENRVAKEPYYTYQTYELDWENHTVEFIYLEHHHHHH-

NetG-NusA recombinant protein

SEQ ID NO: 6

MNKEILAVVEAVSNEKALPREKIFEALESALATATKKKYEQEIDVRVQID

RKSGDFDTFRRWLVVDEVTQPTKEITLEAARYEDESLNLGDYVEDQIESV

TFDRITTQTAKQVIVQKVREAERAMVVDQFREHEGEIITGVVKKVNRDNI

SLDLGNNAEAVILREDMLPRENFRPGDRVRGVLYSVRPEARGAQLFVTRS

KPEMLIELFRIEVPEIGEEVIEIKAAARDPGSRAKIAVKTNDKRIDPVGA

CVGMRGARVQAVSTELGGERIDIVLWDDNPAQFVINAMAPADVASIVVDE

DKHTMDIAVEAGNLAQAIGRNGQNVRLASQLSGWELNVMTVDDLQAKHQA

EAHAAIDTFTKYLDIDEDFATVLVEEGFSTLEELAYVPMKELLEIEGLDE

PTVEALRERAKNALATIAQAQEESLGDNKPADDLLNLEGVDRDLAFKLAA

RGVCTLEDLAEQGIDDLADIEGLTDEKAGALIMAARNICWFGDEATSGSG

HHHHHHSAGKETAAAKFERQHMDSPPPTGLVPRGSAGSGTIDDDDKSPGA

RGSATLPEIIESNGKKAELYTSSDANDTNDVKTSISASFIEDEHDSNLTA

LINLKGFIPSKLIKTGDYYHGRMDWPSKYRISVLSVDYNDNEEVKIIESI

PSNKIETIQVSESIGYTVGGEISANKESASGGLNANYSVQRSISYEQPDF

KTVKKSDSTKAASWDVVFNCNKDGYDRNSHHPFYGNQLFMKSRLYNTGIN

NLTDNKDLSTLISGGFSPNMAVALKAPKGTKKSQLILSYQTYHDLYKLDW

TGTEWWGSNHQAKTPTYATHAYEIDWENHKVTFKYLEHHHHHH

NetF-NusA nucleotide sequence

SEQ ID NO: 7 atgaacaaagaaattttggctgtagttgaagccgtatccaatgaaaaggc gctacctcgcgagaagattttcgaagcattggaaagcgcgctggcgacag caacaaagaaaaaatatgaacaagagatcgacgtccgcgtacagatcgat cgcaaaagcggtgattttgacactttccgtcgctggttagttgttgatga agtcacccagccgaccaaggaaatcacccttgaagccgcacgttatgaag TABLE 11-continued

| Table of Sequences |
|---|
| atgaaagcctgaacctgggcgattacgttgaagatcagattgagtctgtt |
| acctttgaccgtatcactacccagacggcaaaacaggttatcgtgcagaa |
| agtgcgtgaagccgaacgtgcgatggtggttgatcagttccgtgaacacg |
| aaggtgaaatcatcaccggcgtggtgaaaaaagtaaaccgcgacaacatc |
| tctctggatctgggcaacaacgctgaagccgtgatcctgcgcgaagatat |
| gctgccgcgtgaaaacttccgccctggcgaccgcgttcgtggcgtgctct |
| attccgttcgcccggaagcgcgtggcgcgcaactgttcgtcactcgttcc |
| aagccggaaatgctgatcgaactgttccgtattgaagtgccagaaatcgg |
| cgaagaagtgattgaaattaaagcagcggctcgcgatccgggttacgtgc |
| gaaaatcgcggtgaaaaccaacgataaacgtatcgatccggtaggtgctt |
| gcgtaggtatgcgtggcgcgcgtgttcaggcggtgtctactgaactgggt |
| ggcgagcgtatcgatatcgtcctgtgggatgataacccggcgcagttcgt |
| gattaacgcaatggcaccggcagacgttgatctatcgtggtggatgaaga |
| taaacacaccatggacatcgccgttgaagccggtaatctggcgcaggcga |
| ttggccgtaacggtcagaacgtgcgtctggcttcgcaactgagcggttgg |
| gaactcaacgtgatgaccgttgacgacctgcaagctaagcatcaggcgga |
| agcgcacgcagcgatcgacaccttcaccaaatatacgacatcgacgaaga |
| cttcgcgactgttctggtagaagaaggatctcgacgctggaagaattggc |
| ctatgtgccgatgaaagagctgttggaaatcgaaggccttgatgagccga |
| ccgttgaagcactgcgcgagcgtgctaaaaatgcactggccaccattgca |
| caggcccaggaagaaagcctcggtgataacaaaccggctgacgatctgct |
| gaaccttgaaggggtagatcgtgatttggcattcaaactggccgcccgtg |
| gcgtttgtacgctggaagatctcgccgaacagggcattgatgatctggct |
| gatatcgaagggttgaccgacgaaaaagccggagcactgattatggctgc |
| ccgtaatatttgctggttcggtgacgaagcgactagtggttctggtcatc |
| accatcaccatcactccgcgggtaaagaaaccgctgctgcgaaatttgaa |
| cgccagcacatggactcgccaccgccaactggtctggtcccccggggcag |
| cgcgggttctggtacgattgatgacgacgacaagagtccgggagctcgtg |
| gatccgaattcaattcctttcctgaaagtattattaactcaaaaggtaaa |
| caagctgaggtttatacatcatcagatgcttctgaaagagatggtataaa |
| gacatctttatcagcatcatttattgaagatccaaacagtaataacttaa |
| cagacttgtttctttaaaaggatttataccttctggattaattaaaacag |
| gaacttattacagtgcaaatatgtattggccaagtaagtataatataaat |
| attgaaactactgatgaaaaaaataatgttaaaattttagaaagcattcc |
| aagtaatacgatagaaacagtaagagtaactgaaagtatgggttatagta |
| ttggtggaaatgtttccgttagtaaaaagtcatcttcagttggagcaaat |
| gctggttttaatgttcaacgttcagtacaatatgagcaacctgatttcaa |
| gacgatacagaaatctgatggaattaggaaggcttcttggaacatagtgt |
| ttaacaagacaaaagatggatatgaccaaaattcgtatcatgctctatat |

TABLE 11-continued

| Table of Sequences |
|---|
| ggcaatcaattatttatgaaatctaggttacataatacaggtgcaaaaaa |
| tttagttgaagataaagatttatcaccattaatttctggtgggttcactc |
| ctaatatggtaattgctcttaaggcaccaaaaggcacaaaaaaatcaatg |
| attaatttaaactataacttatatcaagatttatatactttagagtggta |
| taaaacccaatggtggggagaaaatcgtgttgcaaaagaaccatattata |
| cctatcaaacatatgaacttgattgggagaatcatactgtagaatttata |
| tacctcgagcaccaccaccaccaccactaatgttaa |
| NetF-NusA nucleotide sequence |
| SEQ ID NO: 7 |
| atgaacaaagaaattttggctgtagttgaagccgtatccaatgaaaaggc |
| gctacctcgcgagaagattttcgaagcattggaaagcgcgctggcgacag |
| caacaaagaaaaaatatgaacaagagatcgacgtccgcgtacagatcgat |
| cgcaaaagcggtgattttgacactttccgtcgctggttagttgttgatga |
| agtcacccagccgaccaaggaaatcacccttgaagccgcacgttatgaag |
| atgaaagcctgaacctgggcgattacgttgaagatcagattgagtctgtt |
| acctttgaccgtatcactacccagacggcaaaacaggttatcgtgcagaa |
| agtgcgtgaagccgaacgtgcgatggtggttgatcagttccgtgaacacg |
| aaggtgaaatcatcaccggcgtggtgaaaaaagtaaaccgcgacaacatc |
| tctctggatctgggcaacaacgctgaagccgtgatcctgcgcgaagatat |
| gctgccgcgtgaaaacttccgccctggcgaccgcgttcgtggcgtgctct |
| attccgttcgcccggaagcgcgtggcgcgcaactgttcgtcactcgttcc |
| aagccggaaatgctgatcgaactgttccgtattgaagtgccagaaatcgg |
| cgaagaagtgattgaaattaaagcagcggctcgcgatccgggttctcgtg |
| cgaaaatcgcggtgaaaaccaacgataaacgtatcgatccggtaggtgct |
| tgcgtaggtatgcgtggcgcgcgtgttcaggcggtgtctactgaactggg |
| tggcgagcgtatcgatatcgtcctgtgggatgataacccggcgcagttcg |
| tgattaacgcaatggcaccggcagacgttgcttctatcgtggtggatgaa |
| gataaacacaccatggacatcgccgttgaagccggtaatctggcgcaggc |
| gattggccgtaacggtcagaacgtgcgtctggcttcgcaactgagcggtt |
| gggaactcaacgtgatgaccgttgacgacctgcaagctaagcatcaggcg |
| gaagcgcacgcagcgatcgacaccttcaccaaatatctcgacatcgacga |
| agacttcgcgactgttctggtagaagaaggcttctcgacgctggaagaat |
| tggcctatgtgccgatgaaagagctgttggaaatcgaaggccttgatgag |
| ccgaccgttgaagcactgcgcgagcgtgctaaaaatgcactggccaccat |
| tgcacaggcccaggaagaaagcctcggtgataacaaaccggctgacgatc |
| tgctgaaccttgaaggggtagatcgtgatttggcattcaaactggccgcc |
| cgtggcgtttgtacgctggaagatctcgccgaacagggcattgatgatct |
| ggctgatatcgaagggttgaccgacgaaaaagccggagcactgattatgg |
| ctgcccgtaatatttgctggttcggtgacgaagcgactagtggttctggt |
| catcaccatcaccatcactccgcgggtaaagaaaccgctgctgcgaaatt |

TABLE 11-continued

Table of Sequences tgaacgccagcacatggactcgccaccgccaactggtctggtcccccggg
gcagcgcgggttctggtacgattgatgacgacgacaagagtccgggagct
cgtggatccgaattcaattcctttcctgaaagtattattaactcaaaagg
taaacaagctgaggtttatacatcatcagatgcttctgaaagagatggta
taaagacatctttatcagcatcatttattgaagatccaaacagtaataac
ttaacagctcttgtttctttaaaaggatttataccttctggattaattaa
aacaggaacttattacagtgcaaatatgtattggccaagtaagtataata
taaatattgaaactactgatgaaaaaaataatgttaaaattttagaaagc
attccaagtaatacgatagaaacagtaagagtaactgaaagtatgggtta
tagtattggtggaaatgtttccgttagtaaaaagtcatcttcagttggag
caaatgctggttttaatgttcaacgttcagtacaatatgagcaacctgat
ttcaagacgatacagaaatctgatggaattaggaaggcttcttggaacat
agtgtttaacaagacaaaagatggatatgaccaaaattcgtatcatgctc
tatatggcaatcaattatttatgaaatctaggttacataatacaggtgca
aaaaatttagttgaagataaagatttatcaccattaatttctggtgggtt
cactcctaatatggtaattgctcttaaggcaccaaaaggcacaaaaaaat
caatgattaatttaaactataacttatatcaagatttatatactttagag
tggtataaaacccaatggtggggagaaaatcgtgttgcaaaagaaccata
ttatacctatcaaacatatgaacttgattgggagaatcatactgtagaat
ttatatacctcgagcaccaccaccaccaccactaatgttaa NetG-NusA nucleotide sequence

SEQ ID NO: 8 atgaacaaagaaattttggctgtagttgaagccgtatccaatgaaaaggc
gctacctcgcgagaagattttcgaagcattggaaagcgcgctggcgacag
caacaaagaaaaaatatgaacaagagatcgacgtccgcgtacagatcgat
cgcaaaagcggtgattttgacactttccgtcgctggttagttgttgatga
agtcacccagccgaccaaggaaatcacccttgaagccgcacgttatgaag
atgaaagcctgaacctgggcgattacgttgaagatcagattgagtctgtt
acctttgaccgtatcactacccagacggcaaaacaggttatcgtgcagaa
agtgcgtgaagccgaacgtgcgatggtggttgatcagttccgtgaacacg
aaggtgaaatcatcaccggcgtggtgaaaaaagtaaaccgcgacaacatc
tctctggatctgggcaacaacgctgaagccgtgatcctgcgcgaagatat
gctgccgcgtgaaaacgccgccctggcgaccgcgttcgtggcgtgctcta
ttccgttcgcccggaagcgcgtggcgcgcaactgttcgtcactcgttcca
agccggaaatgctgatcgaactgttccgtattgaagtgccagaaatcggc
gaagaagtgattgaaattaaagcagcggctcgcgatccgggttctcgtgc
gaaaatcgcggtgaaaaccaacgataaacgtatcgatccggtaggtgctt
gcgtaggtatgcgtggcgcgcgtgttcaggcggtgtctactgaactgggt
ggcgagcgtatcgatatcgtcctgtgggatgataacccggcgcagttcgt
gattaacgcaatggcaccggcagacgttgcttctatcgtggtggatgaag TABLE 11-continued Table of Sequences ataaacacaccatggacatcgccgttgaagccggtaatctggcgcaggcg
attggccgtaacggtcagaacgtgcgtctggcttcgcaactgagcggttg
ggaactcaacgtgatgaccgttgacgacctgcaagctaagcatcaggcgg
aagcgcacgcagcgatcgacaccttcaccaaatatctcgacatcgacgaa
gacttcgcgactgttctggtagaagaaggcttctcgacgctggaagaatt
ggcctatgtgccgatgaaagagctgttggaaatcgaaggccttgatgagc
cgaccgttgaagcactgcgcgagcgtgctaaaaatgcactggccaccatt
gcacaggcccaggaagaaagcctcggtgataacaaaccggctgacgatct
gctgaaccttgaaggggtagatcgtgatttggcattcaaactggccgccc
gtggcgtttgtacgctggaagatctcgccgaacagggcattgatgatctg
gctgatatcgaagggttgaccgacgaaaaagccggagcactgattatggc
tgcccgtaatatttgctggttcggtgacgaagcgactagtggttctggtc
atcaccatcaccatcactccgcgggtaaagaaaccgctgctgcgaaattt
gaacgccagcacatggactcgccaccgccaactggtctggtcccccgggg
cagcgcgggttctggtacgattgatgacgacgacaagagtccgggagctc
gtggatccgctacgttgccagaaattattgaatcaaatggtaaaaaagca
gagctttatacttcttcagatgcaaatgatacgaatgatgtaaaaacttc
tatatcagcatcatttattgaagatgaacatgatagtaatttgactgcac
ttattaatttaaaaggatttattccatctaaacttataaaaacaggggat
tattatcatggaagaatggattggccaagcaaatataggatatctgtttt
gtcagtagattataatgataatgaagaagtaaagattatagaaagtattc
cgagtaataaaatagaaactatacaagtaagtgaaagtataggatatact
gttggtggagaaatatcagctaacaaagagtcagcttctggtggattaaa
tgctaactatagtgtacaacgttctatttcttatgaacagccagacttta
aaacagttaaaaaatctgatagtactaaagctgcttcatgggatgtagtt
tttaattgtaataaagatggttatgataggaattctcatcacccatttta
tggaaatcaattatttatgaaatctagattatataatacaggaattaata
atttaactgataataaagatttatcaacattaatttcaggtggattttct
cctaatatggcagttgctcttaaagcaccaaaaggtacgaaaaaatcaca
gcttattttaagttatcaaacttatcatgatttatataagctagattgga
ctggaactgaatggtggggttcaaatcaccaagctaaaacaccaacttat
gcaactcatgcttatgaaattgattgggagaaccataaagtaacatttaa
atatctcgagcaccaccaccaccaccactaatgttaattaagttgggcgt
tcctaggctgataaaacagaatttgcctggcggcagtagcgcggtggtcc
cacctgaccccatgccgaactcagaagtgaaacgccgtagcgccgatggt
agtgtggggtctccccatgcgagagtagggaactgccaggcatcaaataa
aacgaaaggctcagtcgaaagactgggcctttcgttttatctgttgtttg
tcggtgaacgctctcctgagtaggacaaatccgccgggagcggatttgaa
cgttgcgaagcaacggcccggagggtggcgggcaggacgcccgccataaa TABLE 11-continued Table of Sequences ctgccaggcatcaaattaagcagaaggccatcctgacggatggcctttttgcgtttctacaaactcttttgtttatttttctaaatacattcaaatatgtatccgctgagcaataactagcataaccccttggggcctctaaacgggtcttgaggggttttttgctgaaaggaggaactatatccgga NetE nucleotide sequence

SEQ ID NO: 46 ttgaaaagattaaaaattatgtctactagtttagctcttgcaagtattgttagtacaagtatttttcaacacaaactcaagtgtttgcaagtgaattaggcaatactaagaaaatagagctgaaaaatcaaaatggagaaataataaaagaagatggaaaggaagctattaaatacacttctattgatacttatcatgtaaagggttaaaagcaacattaagtggaacttttgttgaagatcaatattctgataagaaaactgattactaaatttagatgggtttataccttcaggtaagaaagtatctggttctacatattatggaaagatgaagtggcctgaagtttatagaattagtatagaaagcgctgatacagctaataaagtaaaaatagcaaattctatacctaaaaatactatagataaaaaggaggtatctaattcaattggatattcaattggaggaaatatatctgttgaaggtaaaagtggtagtgcaggaataaatgcttcatacagtgtacaaaatactataagctatgaacaacctgattttagaacaatccaaagaaaagatgaagaaaagttagcttcatgggatataaaatttgttgaaactaaagatggttataatctggattcatatcatggtatttatgggaatcaattatttatgaaatcaagattatataataatggttatgaaaactttactgatgatagagatctctcaactttaatttcaggtggcttttcacctaatatggcagtagattaacagcgccaaaagatgctaaagaatctatgataacagttacatataaaagatttgacgatgagtatacttttgaattgggaaactactcaatggaggggatcaaataaacgttcaactgcatgtgaatatactgaatttatgtttaaaattaattgggaaaaccatacaattgaacgttttctataa NetE amino acid sequence

SEQ ID NO: 47

MKRLKIMSTSLALASIVSTSIFSTQTQVFASELGNTKKIELKNQNGEIIKEDGKEAIKYTSIDTSSCKGLKATLSGTFVEDQYSDKKTALLNLDGFIPSGKKVSGSTYYGKMKWPEVYRISIESADTANKVKIANSIPKNTIDKKEVSNSIGYSIGGNISVEGKSGSAGINASYSVQNTISYEQPDFRTIQRKDEEKLASWDIKFVETKDGYNLDSYHGIYGNQLFMKSRLYNNGYENFTDDRDLSTLISGGFSPNMAVALTAPKDAKESMITVTYKRFDDEYTLNWETTQWRGSNKRSTACEYTEFMFKINWENHTIERFL

NetE-NusA nucleotide sequence

SEQ ID NO: 48 atgaacaaagaaattttggctgtagttgaagccgtatccaatgaaaaggcgctacctcgcgagaagattttcgaagcattggaaagcgcgctggcgacagcaacaaagaaaaaatatgaacaagagatcgacgtccgcgtacagatcgatcgcaaaagcggtgattttgacactttccgtcgctggttagttgttgatgaagtcacccagccgaccaaggaaatcacccttgaagccgcacgttatgaagatgaaagcctgaacctgggcgattacgttgaagatcagattgagtctgttacctttgaccgtatcactacccagacggcaaaacaggttatcgtgcagaaagtgcgtgaagccgaacgtgcgatggtggttgatcagttccgtgaacacgaaggtgaaatcatcaccggcgtggtgaaaaaagtaaaccgcgacaacatctctctggatctgggcaacaacgctgaagccgtgatcctgcgcgaagatatgctgccgcgtgaaaacttccgccctggcgaccgcgttcgtggcgtgctctattccgttcgcccggaagcgcgtggcgcgcaactgttcgtcactcgttccaagccggaaatgctgatcgaactgttccgtattgaagtgccagaaatcggcgaagaagtgattgaaattaaagcagcggctcgcgatccgggttctcgtgcgaaaatcgcggtgaaaaccaacgataaacgtatcgatccggtaggtgcttgcgtaggtatgcgtggcgcgcgtgttcaggcggtgtctactgaactgggtggcgagcgtatcgatatcgtcctgtgggatgataacccggcgcagttcgtgattaacgcaatggcaccggcagacgttgcttctatcgtggtggatgaagataaacacaccatggacatcgccgttgaagccggtaatctggcgcaggcgattggccgtaacggtcagaacgtgcgtctggatcgcaactgagcggttgggaactcaacgtgatgaccgttgacgacctgcaagctaagcatcaggcggaagcgcacgcagcgatcgacaccttcaccaaatatctcgacatcgacgaagacttcgcgactgttctggtagaagaaggcttctcgacgctggaagaattggcctatgtgccgatgaaagagctgttggaaatcgaaggccttgatgagccgaccgttgaagcactgcgcgagcgtgctaaaaatgcactggccaccattgcacaggcccaggaagaaagcctcggtgataacaaaccggctgacgatctgctgaaccttgaaggggtagatcgtgatttggcattcaaactggccgcccgtggcgtttgtacgctggaagatctcgccgaacagggcattgatgatctggctgatatcgaagggttgaccgacgaaaaagccggagcactgattatggctgcccgtaatatttgctggttcggtgacgaagcgactagtggttctggtcatcaccatcaccatcactccgcgggtaaagaaaccgctgctgcgaaatttgaacgccagcacatggactcgccaccgccaactggtctggtcccccggggcagcgcgggttctggtacgattgatgacgacgacaagagtccgggagctcgtggatccgaattcatgtctactagtttagctcttgcaagtattgttagtacaagtatttttcaacacaaactcaagtgtttgcaagtgaattaggcaatactaagaaaatagagctgaaaaatcaaaatggagaaataataaaagaagatggaaaggaagctattaaatacacttctattgatacttcttcatgtaaagggttaaaagcaacattaagtggaacttttgttgaagatcaatattctgataagaaaactgctttactaaatttagatgggtttataccttcaggtaagaaagtatctggttctacatattatggaaagatgaagtggcctgaagtttatagaattagtatagaaagcgctgatacagctaataaagtaaaaatagcaaattctatacctaaaaatactatagataaaaaggaggtatctaattcaattggatattcaattggaggaaatatatctgttgaaggtaaaagtggtagtgcaggaataaatgcttcatacagtgtacaaaatactataagctatgaacaacc TABLE 11-continued

| Table of Sequences |
|---|
| tgattttagaacaatccaaagaaaagatgaagaaaagttagatcatggga |
| tataaaatttgttgaaactaaagatggttataatctggattcatatcatg |
| gtatttatgggaatcaattatttatgaaatcaagattatataataatggt |
| tatgaaaactttactgatgatagagatctacaaattaatttcaggtggat |
| ttcacctaatatggcagtagattaacagcgccaaaagatgaaaagaatct |
| atgataacagttacatataaaagatttgacgatgagtatactttgaattg |
| ggaaactactcaatggaggggatcaaataaacgttcaactgcatgtgaat |
| atactgaatttatgtttaaaattaattgggaaaaccatacaattgaacgt |
| tttctactcgagcaccaccaccaccaccact |
| NetE-NusA recombinant protein SEQ ID NO: 49 |
| MNKEILAVVEAVSNEKALPREKIFEALESALATATKKKYEQEIDVRVQID |
| RKSGDFDTFRRWLVVDEVTQPTKEITLEAARYEDESLNLGDYVEDQIESV |
| TFDRITTQTAKQVIVQKVREAERAMVVDQFREHEGEIITGVVKKVNRDNI |
| SLDLGNNAEAVILREDMLPRENFRPGDRVRGVLYSVRPEARGAQLFVTRS |
| KPEMLIELFRIEVPEIGEEVIEIKAAARDPGSRAKIAVKTNDKRIDPVGA |
| CVGMRGARVQAVSTELGGERIDIVLWDDNPAQFVINAMAPADVASIVVDE |
| DKHTMDIAVEAGNLAQAIGRNGQNVRLASQLSGWELNVMTVDDLQAKHQA |
| EAHAAIDTFTKYLDIDEDFATVLVEEGFSTLEELAYVPMKELLEIEGLDE |
| PTVEALRERAKNALATIAQAQEESLGDNKPADDLLNLEGVDRDLAFKLAA |
| RGVCTLEDLAEQGIDDLADIEGLTDEKAGALIMAARNICWFGDEATSGSG |
| HHHHHHSAGKETAAAKFERQHMDSPPPTGLVPRGSAGSGTIDDDDKSPGA |
| RGSEFSELGNTKKIELKNQNGEIIKEDGKEAIKYTSIDTSSCKGLKATLS |
| GTFVEDQYSDKKTALLNLDGFIPSGKKVSGSTYYGKMKWPEVYRISIESA |
| DTANKVKIANSIPKNTIDKKEVSNSIGYSIGGNISVEGKSGSAGINASYS |
| VQNTISYEQPDFRTIQRKDEEKLASWDIKFVETKDGYNLDSYHGIYGNQL |
| FMKSRLYNNGYENFTDDRDLSTLISGGFSPNMAVALTAPKDAKESMITVT |
| YKRFDDEYTLNWETTQWRGSNKRSTACEYTEFMFKINWENHTIERFLKLA |
| AAQLYTRASQPELAPEDPEDLEHHHHHH |

REFERENCES

Alonzo F 3rd, Torres V J (2014) The bicomponent pore-forming leucocidins of *Staphylococcus aureus*. Microbiol Mol Biol Rev 78: 199-230.

Bacciarini L N, Boerlin P, Straub R, Frey J, Grone A (2003) Immunohistochemical localization of *Clostridium perfringens* beta2-toxin in the gastrointestinal tract of horses. Vet Pathol 40: 376-381.

Bannam T L, Teng W L, Bulach D, Lyras D, Rood J I (2006) Functional identification of conjugation and replication regions of the tetracycline resistance plasmid pCW3 from *Clostridium perfringens*. J Bacteriol 188: 4942-4951.

Bannam T L, Yan X X, Harrison P F, Seemann T, Keyburn A L, et al. (2011) Necrotic enteritis-derived *Clostridium perfringens* strain with three closely related independently conjugative toxin and antibiotic resistance plasmids. MBio 2: e00190-11.

Burrows C F (1977) Canine hemorrhagic gastroenteritis. J Am Anim Hosp Assoc 13: 451-458.

Chalmers G, Martin S W, Hunter D B, Prescott J F, Weber L J, et al. (2008) Genetic diversity of *Clostridium perfringens* isolated from healthy broiler chicken at a commercial farm. Net Microbiol 127: 116-127.

Chase K, Jones P, Martin A, Ostrander E A, Lark K G (2009) Genetic mapping of fixed phenotypes: disease frequency as a breed characteristic. J Hered 1: 37-41.

Cheung J K, Dupuy B, Deveson D S, Rood J I (2004) The spatial organization of the VirR boxes is critical for VirR-mediated expression of the perfringolysin O gene, pfoA, from *Clostridium perfringens*. J Bacteriol 186: 3321-3330.

De S, Olson R (2011) Crystal structure of the *Vibrio cholerae* cytolysin heptamer reveals common features among disparate pore-forming toxins. Proc Natl Acad Sci USA 108: 7385-7390.

Deguchi A, Miyamoto K, Kuwahara T, Miki Y, Kaneko I, et al. (2009) Genetic characterization of type A enterotoxigenic *Clostridium perfringens* strains. PLoS One 4: e5598.

Diab S S, Kinde H, Moore J, Shahriar M F, Odani J, et al. (2011) Pathology of *Clostridium perfringens* Type C enterotoxemia in horses. Vet Pathol 49: 255-263.

Donahue M, Williams N (2002) Clostridial enterocolitis in horses. Equine Dis Quart 10: 4-5.

Donaldson M T, Palmer J E (1999) Prevalence of *Clostridium perfringens* enterotoxin and *Clostridium difficile* toxin A in feces of horses with diarrhea and colic. J Am Vet Med Assoc 215: 358-361.

Dyrløv Bendtsen J, Nielsen H, von Heijne G, Brunak S (2004) Improved prediction of signal peptides: SignalP 3.0. J Mol Biol 340: 783-795.

East L M, Savage C J, Traub-Dargatz J L, Dickinson C E, Ellis R P (1998) Enterocolitis associated with *Clostridium perfringens* infection in neonatal foals: 54 cases (1988-1997). J Am Vet Med Assoc 212: 1751-1756.

East L M, Dargatz D A, Traub-Dargatz J L, Savage C J (2000) Foaling-management practices associated with the occurrence of enterocolitis attributed to *Clostridium perfringens* infection in the equine neonate. Prev Vet Med 46: 61-74.

Gardy J L, Laird M R, Chen F, Rey S, Walsh C J, et al. (2005) PSORTb v. 2.0: Expanded prediction of bacterial protein subcellular localization and insights gained from comparative proteome analysis. Bioinformatics 21: 617-623.

Hazlett M J, Kircanski J, Slavic D, Prescott J F (2011) Beta2 toxigenic *Clostridium perfringens* type A colitis in a three-day-old foal. J Vet Diagn Invest 23: 373-376.

Heap J T, Pennington O J, Cartman S T, Carter G P, Minton N P (2007) The ClosTron: a universal gene knock-out system for the genus *Clostridium*. J Microbiol Methods 70: 452-464.

Heap J T, Pennington O J, Cartman S T, Minton N P (2009) A modular system for *Clostridium* shuttle plasmids. J Microbiol Meth 78: 79-85.

Herholz C, Miserez R, Nicolet J, Frey J, Popoff M, et al. (1999) Prevalence of beta2-toxigenic *Clostridium perfringens* in horses with intestinal disorders. J Clin Microbiol 37: 358-361.

Hibberd M C, Neumann A P, Rehberger T G, Siragusa G R (2011) Multilocus sequence typing subtypes of poultry

*Clostridium perfringens* isolates demonstrate disease niche partitioning. J Clin Microbiol 49: 1556-1567.

Hirji K F, Tsiatis A A, Mehta C R (1989) Median unbiased estimation for binary data. Am Stat 43: 7-11.

Huyet J, Naylor C E, Savva C G, Gibert M, Popoff M R, et al. (2013) Structural insights into *Clostridium perfringens* delta toxin pore formation. PLoS One 8: e66673.

Jost B H, Billington S J, Trinh H T, Bueschel D M, Songer J G (2005) Atypical cpb2 genes, encoding beta2-toxin in *Clostridium perfringens* isolates of nonporcine origin. Infect Immun 73: 652-656.

Jost B H, Trinh H T, Songer J G (2006) Clonal relationships among *Clostridium perfringens* of porcine origin as determined by multilocus sequence typing. Vet Microbiol 116: 158-165.

Kanoe M, Inoue S, Abe T, Anzai T, Kamada M, et al. (1990) Isolation of *Clostridium perfringens* from foals. Microbios 64: 153-158.

Keyburn A L, Boyce J D, Vaz P, Bannam T L, Ford M E, et al. (2008) NetB, a new toxin that is associated with avian necrotic enteritis caused by *Clostridium perfringens*. PLoS Pathog 4: e26.

Kircanski J, Parreira V R, Whiteside S, Pei Y, Prescott J F (2012a) The majority of atypical cpb2 genes in *Clostridium perfringens* isolates of different domestic animal origin are expressed. Vet Microbiol 159: 371-374.

Kircanski J, Hodgins D, Soltes G, Pei Y, Parreira V R, et al. (2012b) Development of an antigen-capture enzyme-linked immunosorbent assay for *Clostridium perfringens* beta2-toxin in porcine feces and the neonatal piglet intestine. J Vet Diagn Invest 24: 895-902.

Lepp D, Gong J, Boerlin P, Parreira V R, Songer J G, et al. (2013) Identification of accessory genome regions in poultry *Clostridium perfringens* isolates carrying the NetB plasmid. J Bact 195: 1152-1166.

Li J, Adams V, Bannam T L, Miyamoto K, Garcia J P, et al. (2013) Toxin plasmids of *Clostridium perfringens*. Microbiol Mol Biol Rev 77: 208-233.

Marchler-Bauer A, Anderson J B, Chitsaz F, Derbyshire M K, DeWeese-Scott C, et al. (2009) CDD: specific functional annotation with the Conserved Domain Database. Nucl Acids Res 37: 205-210.

Marks S L (2012) *Clostridium perfringens*- and *Clostridium difficile*-associated diarrhea. In: Greene C E, editors. Infectious diseases of the dog and cat, 4th ed. St. Louis: Saunders Elsevier. pp. 393-398.

McGavin M D, Zachary J F (2007) Pathologic basis of veterinary disease, $4^{th}$ edition. Mosby. 1476 p.

Mehdizadeh Gohari I, Arroyo L, MacInnes J I, Timoney J F, Parreira V R, et al. (2014) Characterization of *Clostridium perfringens* in the feces of adult horses and foals with acute diarrhea. Can J Vet Res 78: 1-7.

Netherwood T, Wood J L, Mumford J A, Chanter N (1998) Molecular analysis of the virulence determinants of *Clostridium perfringens* associated with foal diarrhea. Vet J 155: 289-294.

Nowell V J, Poppe C, Parreira V R, Jiang Y F, Reid-Smith R, et al. (2010) *Clostridium perfringens* in retail chicken. Anaerobe 16: 314-315.

Nowell V J, Kropinski A M, Songer J G, MacInnes J I, Parreira V R, et al. (2012) Genome sequencing and analysis of a Type A *Clostridium perfringens* isolate from a case of bovine clostridial abomasitis. PLoS One 7: e32271.

Obana N, Nakamura K (2011) A novel toxin regulator, the CPE1446-CPE1447 protein heteromeric complex, controls toxin genes in *Clostridium perfringens*. J Bacteriol 193: 4417-4424.

Ohtani K, Hirakawa H, Tashiro K, Yoshizawa S, Kuhara S, et al. (2010) Identification of a two-component VirR/VirS regulon in *Clostridium perfringens*. Anaerobe 16: 258-264.

Parreira V R, Costa M, Eikmeyer F, Blom J, Prescott J F (2012) Sequence of two plasmids from *Clostridium perfringens* chicken necrotic enteritis isolates and comparison with *C. perfringens* conjugative plasmids. PLoS One 7: e49753.

Popoff M R, Bouvet P (2013) Genetic characteristics of toxigenic Clostridia and toxin gene evolution. Toxicon 75: 63-89.

Prescott J F, Johnson J A, Patterson J M, Bulmer W S (1978) Haemorrhagic gastroenteritis in the dog associated with *Clostridium welchii*. Vet Record 103: 116-117.

Purdy D, O'Keeffe T A T, Elmore M, Herbert M, McLeod A, et al. (2002) Conjugative transfer of clostridial shuttle vectors from *Escherichia coli* to *Clostridium difficile* through circumvention of the restriction barrier. Mol Microbiol 46: 439-452.

Quigley J D, Martin K R, Dowlen H H (1995) Concentrations of trypsin inhibitor and immunoglobulins in colostrum of Jersey cows. J Dairy Sci 78: 1573-1577.

Roth F, Jansen K, Petzke S (1999) Detection of neutralizing antibodies against alpha-toxin of different *Clostridium septicum* strains in cell culture. FEMS Immunol Med Microbiol 24: 353-359.

Saitou N, Nei M (1987) The neighbor-joining method: a new method for reconstructing phylogenetic trees. Mol Biol Evol 4: 406-425.

Sasaki J, Goryo M, Asahina M, Makara M, Shisido S, et al. (1999) Hemorrhagic enteritis associated with *Clostridium perfringens* Type A in a dog. J Vet Med Sci 61: 175-177.

Savva C G, Fernandes da Costa S P, Bokori-Brown M, Naylor C E, Cole A R, et al. (2013) Molecular architecture and functional analysis of NetB, a pore-forming toxin from *Clostridium perfringens*. J Biol Chem 288: 3512-3522.

Schlegel B J, Van Dreumel T, Slavic D, Prescott J F (2012) *Clostridium perfringens* type A fatal acute hemorrhagic gastroenteritis in a dog. Can Vet J 53: 549-553.

Songer J G (1996) Clostridial enteric diseases of domestic animals. Clin Microbiol Rev 9: 216-234.

Tenover F C, Arbeit R D, Goering R V, Mickelsen P A, Murray B E, et al. (1995) Interpreting chromosomal DNA restriction patterns produced by pulsed field gel electrophoresis: criteria for bacterial strain typing. J Clin Microbiol 33: 2223-2239.

Thompson D R, Parreira V R, Kulkarni R R, Prescott J F (2006) Live attenuated vaccine-based control of necrotic enteritis of broiler chickens. Vet Microbiol 113: 25-34.

Tillotson K, Traub-Dargatz J L, Dickinson C E, Ellis R P, Morley P S, et al. (2002) Population-based study of fecal shedding of *Clostridium perfringens* in broodmares and foals. J Am Vet Med Assoc 220: 342-348.

Timoney J F, Hartmann M, Fallon L, Fallon E, Walker J (2005) Antibody responses of mares to prepartum vaccination with *Clostridium perfringens* bacterin and beta2 toxin. Vet Rec 157: 810-812.

Traub-Dargatz J L, Jones R L (1993) Clostridia-associated enterocolitis in adult horses and foals. Vet Clin North Am Equine Pract 9: 411-421.

Unterer S, Busch K, Leipig M, Hermanns W, Wolf G, et al. (2014) Endoscopically visualized lesions, histologic findings, and bacterial invasion in the gastrointestinal mucosa of dogs with acute hemorrhagic diarrhea syndromes. J Vet Intern Med 28: 52-58.

Vilei E M, Schlatter Y, Perreten V, Straub R, Popoff M R, et al. (2005) Antibiotic-induced expression of a cryptic cpb2 gene in equine beta2-toxigenic *Clostridium perfringens*. Mol Microbiol 57: 1570-1581.

Waters M, Raju D, Garmory H S, Popoff M R, Sarker M R (2005) Regulated expression of the beta2-toxin gene (cpb2) in *Clostridium perfringens* type A isolates from horses with gastrointestinal diseases. J Clin Microbiol 43: 4002-4009.

Weese J S, Staempfli H R, Prescott J F, Kruth S A, Greenwood S J, et al. (2001) The roles of *Clostridium difficile* and enterotoxigenic *Clostridium perfringens* in diarrhea in dogs. J Vet Intern Med 15: 374-378.

Xiao Y, Wagendorp A, Moezelaar R, Abee T, Wells-Bennik M H (2012) A wide variety of *Clostridium perfringens* type A food-borne isolates that carry a chromosomal cpe gene belong to one multilocus sequence typing cluster. Appl Environ Microbiol 78: 7060-7068.

Yan X, Porter C J, Hardy S P, Steer D, Smith A I, et al. (2013) Structural and functional analysis of pore-forming toxin NetB from *Clostridium perfringens*. MBio 4: e00019-13.

Zdobnov E M, Apweiler R (2001) InterProScan—an integration platform for the signature-recognition methods in InterPro. Bioinformatics 17: 847-848.

The invention claimed is:

1. An isolated polypeptide:

(a) encoded by the nucleic acid sequence set forth as SEQ ID NO:1 or 2;

(b) comprising at least 95% sequence identity to the full length sequence protein encoded by SEQ ID NO:1 or 2;

(c) comprising the amino acid sequence set forth as SEQ ID NO:3 or 4; or (d) comprising at least 95% sequence identity to the full length sequence SEQ ID NO:3 or 4;

Wherein the polypeptide is toxoided.

2. An isolated fusion protein comprising (a) a polypeptide comprising the amino acid sequence set forth as SEQ ID NO: 3 or 4, or a polypeptide comprising at least 95% sequence identity to the full length sequence SEQ ID NO: 3 or 4, fused to (b) a solubilizing protein.

3. The isolated fusion protein of claim 2, wherein the solubilizing protein is NusA.

4. An immunogenic composition comprising the isolated polypeptide of claim 1, and a pharmaceutically acceptable carrier.

5. An immunogenic composition comprising supernatant isolated from a NetF-positive and/or NetG-positive *C. perfringens* strain and an adjuvant; wherein NetF has the amino acid sequence set forth as SEQ ID NO:3 or comprises at least 95% sequence identity to the full length sequence SEQ ID NO:3 and wherein NetG has the amino acid sequence set forth as SEQ ID NO:4 or comprises at least 95% sequence identity to the full length sequence SEQ ID NO:4.

6. The immunogenic composition of claim 5, wherein the supernatant is concentrated.

7. The immunogenic composition of claim 5, further comprising additional isolated NetF or NetG protein or NetF-solubilizing fusion protein or NetG-solubilizing protein.

8. The immunogenic composition of claim 4, further comprising an additional *C. perfringens* toxin protein, wherein the additional *C. perfringens* toxin protein is Cpe, Cpa, NetB, NetE, Cpb2 or TpeL.

* * * * *

SEQUENCE LISTING

```
<160> NUMBER OF SEQ ID NOS: 55

<210> SEQ ID NO 1
<211> LENGTH: 918
<212> TYPE: DNA
<213> ORGANISM: Clostridium perfringens

<400> SEQUENCE: 1

atgaaaaaaa caatatgtac aggtataact atattttctt tattattagg gaatattaca     60

caagtaaaag ctaattcctt tcctgaaagt attattaact caaaaggtaa acaagctgag    120

gtttatacat catcagatgc ttctgaaaga gatggtataa agacatcttt atcagcatca    180

tttattgaag atccaaacag taataactta acagctcttg tttctttaaa aggatttata    240

ccttctggat taattaaaac aggaacttat tacagtgcaa atatgtattg gccaagtaag    300

tataatataa atattgaaac tactgatgaa aaaaataatg ttaaaatttt agaaagcatt    360

ccaagtaata cgatagaaac agtaagagta actgaaagta tgggttatag tattggtgga    420

aatgtttccg ttagtaaaaa gtcatcttca gttggagcaa atgctggttt taatgttcaa    480

cgttcagtac aatatgagca acctgatttc aagacgatac agaaatctga tggaattagg    540

aaggcttctt ggaacatagt gtttaacaag acaaaagatg gatatgacca aaattcgtat    600

catgctctat atggcaatca attatttatg aaatctaggt tacataatac aggtgcaaaa    660

aatttagttg aagataaaga tttatcacca ttaatttctg gtgggttcac tcctaatatg    720

gtaattgctc ttaaggcacc aaaaggcaca aaaaaatcaa tgattaattt aaactataac    780

ttatatcaag atttatatac tttagagtgg tataaaaccc aatggtgggg agaaaatcgt    840

gttgcaaaag aaccatatta tacctatcaa acatatgaac ttgattggga gaatcatact    900

gtagaattta tatactaa                                                  918


<210> SEQ ID NO 2
<211> LENGTH: 921
<212> TYPE: DNA
<213> ORGANISM: Clostridium perfringens

<400> SEQUENCE: 2

ttgagaagat tgttttgttc aggattagta gcattaacct taataacagg aaatatttca     60

tatgtaagag cagctacgtt gccagaaatt attgaatcaa atggtaaaaa agcagagctt    120

tatacttctt cagatgcaaa tgatacgaat gatgtaaaaa cttctatatc agcatcattt    180

attgaagatg aacatgatag taatttgact gcacttatta atttaaaagg atttattcca    240

tctaaactta taaaaacagg ggattattat catggaagaa tggattggcc aagcaaatat    300
```

-continued

```
aggatatctg ttttgtcagt agattataat gataatgaag aagtaaagat tatagaaagt    360

attccgagta ataaaataga aactatacaa gtaagtgaaa gtataggata tactgttggt    420

ggagaaatat cagctaacaa agagtcagct tctggtggat taaatgctaa ctatagtgta    480

caacgttcta tttcttatga acagccagac tttaaaacag ttaaaaaatc tgatagtact    540

aaagctgctt catgggatgt agtttttaat tgtaataaag atggttatga taggaattct    600

catcacccat tttatggaaa tcaattattt atgaaatcta gattatataa tacaggaatt    660

aataatttaa ctgataataa agatttatca acattaattt caggtggatt ttctcctaat    720

atggcagttg ctcttaaagc accaaaaggt acgaaaaaat cacagcttat tttaagttat    780

caaacttatc atgatttata taagctagat tggactggaa ctgaatggtg gggttcaaat    840

caccaagcta aaacaccaac ttatgcaact catgcttatg aaattgattg ggagaaccat    900

aaagtaacat ttaaatatta a                                                921


<210> SEQ ID NO 3
<211> LENGTH: 305
<212> TYPE: PRT
<213> ORGANISM: Clostridium perfringens

<400> SEQUENCE: 3

Met Lys Lys Thr Ile Cys Thr Gly Ile Thr Ile Phe Ser Leu Leu Leu
1               5                   10                  15

Gly Asn Ile Thr Gln Val Lys Ala Asn Ser Phe Pro Glu Ser Ile Ile
            20                  25                  30

Asn Ser Lys Gly Lys Gln Ala Glu Val Tyr Thr Ser Ser Asp Ala Ser
        35                  40                  45

Glu Arg Asp Gly Ile Lys Thr Ser Leu Ser Ala Ser Phe Ile Glu Asp
    50                  55                  60

Pro Asn Ser Asn Asn Leu Thr Ala Leu Val Ser Leu Lys Gly Phe Ile
65                  70                  75                  80

Pro Ser Gly Leu Ile Lys Thr Gly Thr Tyr Tyr Ser Ala Asn Met Tyr
                85                  90                  95

Trp Pro Ser Lys Tyr Asn Ile Asn Ile Glu Thr Thr Asp Glu Lys Asn
            100                 105                 110

Asn Val Lys Ile Leu Glu Ser Ile Pro Ser Asn Thr Ile Glu Thr Val
        115                 120                 125

Arg Val Thr Glu Ser Met Gly Tyr Ser Ile Gly Gly Asn Val Ser Val
    130                 135                 140

Ser Lys Lys Ser Ser Ser Val Gly Ala Asn Ala Gly Phe Asn Val Gln
145                 150                 155                 160

Arg Ser Val Gln Tyr Glu Gln Pro Asp Phe Lys Thr Ile Gln Lys Ser
                165                 170                 175

Asp Gly Ile Arg Lys Ala Ser Trp Asn Ile Val Phe Asn Lys Thr Lys
            180                 185                 190

Asp Gly Tyr Asp Gln Asn Ser Tyr His Ala Leu Tyr Gly Asn Gln Leu
        195                 200                 205

Phe Met Lys Ser Arg Leu His Asn Thr Gly Ala Lys Asn Leu Val Glu
    210                 215                 220

Asp Lys Asp Leu Ser Pro Leu Ile Ser Gly Gly Phe Thr Pro Asn Met
225                 230                 235                 240

Val Ile Ala Leu Lys Ala Pro Lys Gly Thr Lys Lys Ser Met Ile Asn
                245                 250                 255

Leu Asn Tyr Asn Leu Tyr Gln Asp Leu Tyr Thr Leu Glu Trp Tyr Lys
```

-continued

```
            260                 265                 270

Thr Gln Trp Trp Gly Glu Asn Arg Val Ala Lys Glu Pro Tyr Tyr Thr
        275                 280                 285

Tyr Gln Thr Tyr Glu Leu Asp Trp Glu Asn His Thr Val Glu Phe Ile
    290                 295                 300

Tyr
305


<210> SEQ ID NO 4
<211> LENGTH: 306
<212> TYPE: PRT
<213> ORGANISM: Clostridium perfringens

<400> SEQUENCE: 4

Met Arg Arg Leu Phe Cys Ser Gly Leu Val Ala Leu Thr Leu Ile Thr
1               5                   10                  15

Gly Asn Ile Ser Tyr Val Arg Ala Ala Thr Leu Pro Glu Ile Ile Glu
            20                  25                  30

Ser Asn Gly Lys Lys Ala Glu Leu Tyr Thr Ser Ser Asp Ala Asn Asp
        35                  40                  45

Thr Asn Asp Val Lys Thr Ser Ile Ser Ala Ser Phe Ile Glu Asp Glu
    50                  55                  60

His Asp Ser Asn Leu Thr Ala Leu Ile Asn Leu Lys Gly Phe Ile Pro
65                  70                  75                  80

Ser Lys Leu Ile Lys Thr Gly Asp Tyr Tyr His Gly Arg Met Asp Trp
                85                  90                  95

Pro Ser Lys Tyr Arg Ile Ser Val Leu Ser Val Asp Tyr Asn Asp Asn
            100                 105                 110

Glu Glu Val Lys Ile Ile Glu Ser Ile Pro Ser Asn Lys Ile Glu Thr
        115                 120                 125

Ile Gln Val Ser Glu Ser Ile Gly Tyr Thr Val Gly Gly Glu Ile Ser
    130                 135                 140

Ala Asn Lys Glu Ser Ala Ser Gly Gly Leu Asn Ala Asn Tyr Ser Val
145                 150                 155                 160

Gln Arg Ser Ile Ser Tyr Glu Gln Pro Asp Phe Lys Thr Val Lys Lys
                165                 170                 175

Ser Asp Ser Thr Lys Ala Ala Ser Trp Asp Val Val Phe Asn Cys Asn
            180                 185                 190

Lys Asp Gly Tyr Asp Arg Asn Ser His His Pro Phe Tyr Gly Asn Gln
        195                 200                 205

Leu Phe Met Lys Ser Arg Leu Tyr Asn Thr Gly Ile Asn Asn Leu Thr
    210                 215                 220

Asp Asn Lys Asp Leu Ser Thr Leu Ile Ser Gly Gly Phe Ser Pro Asn
225                 230                 235                 240

Met Ala Val Ala Leu Lys Ala Pro Lys Gly Thr Lys Lys Ser Gln Leu
                245                 250                 255

Ile Leu Ser Tyr Gln Thr Tyr His Asp Leu Tyr Lys Leu Asp Trp Thr
            260                 265                 270

Gly Thr Glu Trp Trp Gly Ser Asn His Gln Ala Lys Thr Pro Thr Tyr
        275                 280                 285

Ala Thr His Ala Tyr Glu Ile Asp Trp Glu Asn His Lys Val Thr Phe
    290                 295                 300

Lys Tyr
305
```

<210> SEQ ID NO 5
<211> LENGTH: 844
<212> TYPE: PRT
<213> ORGANISM: Artificial Sequence
<220> FEATURE:
<223> OTHER INFORMATION: NetF-NusA recombinant protein

<400> SEQUENCE: 5

Met Asn Lys Glu Ile Leu Ala Val Val Glu Ala Val Ser Asn Glu Lys
1 5 10 15

Ala Leu Pro Arg Glu Lys Ile Phe Glu Ala Leu Glu Ser Ala Leu Ala
20 25 30

Thr Ala Thr Lys Lys Lys Tyr Glu Gln Glu Ile Asp Val Arg Val Gln
35 40 45

Ile Asp Arg Lys Ser Gly Asp Phe Asp Thr Phe Arg Arg Trp Leu Val
50 55 60

Val Asp Glu Val Thr Gln Pro Thr Lys Glu Ile Thr Leu Glu Ala Ala
65 70 75 80

Arg Tyr Glu Asp Glu Ser Leu Asn Leu Gly Asp Tyr Val Glu Asp Gln
85 90 95

Ile Glu Ser Val Thr Phe Asp Arg Ile Thr Thr Gln Thr Ala Lys Gln
100 105 110

Val Ile Val Gln Lys Val Arg Glu Ala Glu Arg Ala Met Val Val Asp
115 120 125

Gln Phe Arg Glu His Glu Gly Glu Ile Ile Thr Gly Val Val Lys Lys
130 135 140

Val Asn Arg Asp Asn Ile Ser Leu Asp Leu Gly Asn Asn Ala Glu Ala
145 150 155 160

Val Ile Leu Arg Glu Asp Met Leu Pro Arg Glu Asn Phe Arg Pro Gly
165 170 175

Asp Arg Val Arg Gly Val Leu Tyr Ser Val Arg Pro Glu Ala Arg Gly
180 185 190

Ala Gln Leu Phe Val Thr Arg Ser Lys Pro Glu Met Leu Ile Glu Leu
195 200 205

Phe Arg Ile Glu Val Pro Glu Ile Gly Glu Glu Val Ile Glu Ile Lys
210 215 220

Ala Ala Ala Arg Asp Pro Gly Ser Arg Ala Lys Ile Ala Val Lys Thr
225 230 235 240

Asn Asp Lys Arg Ile Asp Pro Val Gly Ala Cys Val Gly Met Arg Gly
245 250 255

Ala Arg Val Gln Ala Val Ser Thr Glu Leu Gly Gly Glu Arg Ile Asp
260 265 270

Ile Val Leu Trp Asp Asp Asn Pro Ala Gln Phe Val Ile Asn Ala Met
275 280 285

Ala Pro Ala Asp Val Ala Ser Ile Val Val Asp Glu Asp Lys His Thr
290 295 300

Met Asp Ile Ala Val Glu Ala Gly Asn Leu Ala Gln Ala Ile Gly Arg
305 310 315 320

Asn Gly Gln Asn Val Arg Leu Ala Ser Gln Leu Ser Gly Trp Glu Leu
325 330 335

Asn Val Met Thr Val Asp Asp Leu Gln Ala Lys His Gln Ala Glu Ala
340 345 350

His Ala Ala Ile Asp Thr Phe Thr Lys Tyr Leu Asp Ile Asp Glu Asp
355 360 365

-continued

```
Phe Ala Thr Val Leu Val Glu Glu Gly Phe Ser Thr Leu Glu Glu Leu
    370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
    450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Thr
                485                 490                 495

Ser Gly Ser Gly His His His His His His Ser Ala Gly Lys Glu Thr
            500                 505                 510

Ala Ala Ala Lys Phe Glu Arg Gln His Met Asp Ser Pro Pro Pro Thr
        515                 520                 525

Gly Leu Val Pro Arg Gly Ser Ala Gly Ser Gly Thr Ile Asp Asp Asp
    530                 535                 540

Asp Lys Ser Pro Gly Ala Arg Gly Ser Glu Phe Asn Ser Phe Pro Glu
545                 550                 555                 560

Ser Ile Ile Asn Ser Lys Gly Lys Gln Ala Glu Val Tyr Thr Ser Ser
                565                 570                 575

Asp Ala Ser Glu Arg Asp Gly Ile Lys Thr Ser Leu Ser Ala Ser Phe
            580                 585                 590

Ile Glu Asp Pro Asn Ser Asn Asn Leu Thr Ala Leu Val Ser Leu Lys
        595                 600                 605

Gly Phe Ile Pro Ser Gly Leu Ile Lys Thr Gly Thr Tyr Tyr Ser Ala
    610                 615                 620

Asn Met Tyr Trp Pro Ser Lys Tyr Asn Ile Asn Ile Glu Thr Thr Asp
625                 630                 635                 640

Glu Lys Asn Asn Val Lys Ile Leu Glu Ser Ile Pro Ser Asn Thr Ile
                645                 650                 655

Glu Thr Val Arg Val Thr Glu Ser Met Gly Tyr Ser Ile Gly Gly Asn
            660                 665                 670

Val Ser Val Ser Lys Lys Ser Ser Ser Val Gly Ala Asn Ala Gly Phe
        675                 680                 685

Asn Val Gln Arg Ser Val Gln Tyr Glu Gln Pro Asp Phe Lys Thr Ile
    690                 695                 700

Gln Lys Ser Asp Gly Ile Arg Lys Ala Ser Trp Asn Ile Val Phe Asn
705                 710                 715                 720

Lys Thr Lys Asp Gly Tyr Asp Gln Asn Ser Tyr His Ala Leu Tyr Gly
                725                 730                 735

Asn Gln Leu Phe Met Lys Ser Arg Leu His Asn Thr Gly Ala Lys Asn
            740                 745                 750

Leu Val Glu Asp Lys Asp Leu Ser Pro Leu Ile Ser Gly Gly Phe Thr
        755                 760                 765

Pro Asn Met Val Ile Ala Leu Lys Ala Pro Lys Gly Thr Lys Lys Ser
    770                 775                 780

Met Ile Asn Leu Asn Tyr Asn Leu Tyr Gln Asp Leu Tyr Thr Leu Glu
```

785 790 795 800

Trp Tyr Lys Thr Gln Trp Trp Gly Glu Asn Arg Val Ala Lys Glu Pro
805 810 815

Tyr Tyr Thr Tyr Gln Thr Tyr Glu Leu Asp Trp Glu Asn His Thr Val
820 825 830

Glu Phe Ile Tyr Leu Glu His His His His His His
835 840

<210> SEQ ID NO 6
<211> LENGTH: 843
<212> TYPE: PRT
<213> ORGANISM: Artificial Sequence
<220> FEATURE:
<223> OTHER INFORMATION: NetG-NusA recombinant protein

<400> SEQUENCE: 6

Met Asn Lys Glu Ile Leu Ala Val Val Glu Ala Val Ser Asn Glu Lys
1 5 10 15

Ala Leu Pro Arg Glu Lys Ile Phe Glu Ala Leu Glu Ser Ala Leu Ala
20 25 30

Thr Ala Thr Lys Lys Lys Tyr Glu Gln Glu Ile Asp Val Arg Val Gln
35 40 45

Ile Asp Arg Lys Ser Gly Asp Phe Asp Thr Phe Arg Arg Trp Leu Val
50 55 60

Val Asp Glu Val Thr Gln Pro Thr Lys Glu Ile Thr Leu Glu Ala Ala
65 70 75 80

Arg Tyr Glu Asp Glu Ser Leu Asn Leu Gly Asp Tyr Val Glu Asp Gln
85 90 95

Ile Glu Ser Val Thr Phe Asp Arg Ile Thr Thr Gln Thr Ala Lys Gln
100 105 110

Val Ile Val Gln Lys Val Arg Glu Ala Glu Arg Ala Met Val Val Asp
115 120 125

Gln Phe Arg Glu His Glu Gly Glu Ile Ile Thr Gly Val Val Lys Lys
130 135 140

Val Asn Arg Asp Asn Ile Ser Leu Asp Leu Gly Asn Asn Ala Glu Ala
145 150 155 160

Val Ile Leu Arg Glu Asp Met Leu Pro Arg Glu Asn Phe Arg Pro Gly
165 170 175

Asp Arg Val Arg Gly Val Leu Tyr Ser Val Arg Pro Glu Ala Arg Gly
180 185 190

Ala Gln Leu Phe Val Thr Arg Ser Lys Pro Glu Met Leu Ile Glu Leu
195 200 205

Phe Arg Ile Glu Val Pro Glu Ile Gly Glu Glu Val Ile Glu Ile Lys
210 215 220

Ala Ala Ala Arg Asp Pro Gly Ser Arg Ala Lys Ile Ala Val Lys Thr
225 230 235 240

Asn Asp Lys Arg Ile Asp Pro Val Gly Ala Cys Val Gly Met Arg Gly
245 250 255

Ala Arg Val Gln Ala Val Ser Thr Glu Leu Gly Gly Glu Arg Ile Asp
260 265 270

Ile Val Leu Trp Asp Asp Asn Pro Ala Gln Phe Val Ile Asn Ala Met
275 280 285

Ala Pro Ala Asp Val Ala Ser Ile Val Val Asp Glu Asp Lys His Thr
290 295 300

Met Asp Ile Ala Val Glu Ala Gly Asn Leu Ala Gln Ala Ile Gly Arg

-continued

```
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
    370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
    450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Thr
                485                 490                 495

Ser Gly Ser Gly His His His His His His Ser Ala Gly Lys Glu Thr
            500                 505                 510

Ala Ala Ala Lys Phe Glu Arg Gln His Met Asp Ser Pro Pro Pro Thr
        515                 520                 525

Gly Leu Val Pro Arg Gly Ser Ala Gly Ser Gly Thr Ile Asp Asp Asp
    530                 535                 540

Asp Lys Ser Pro Gly Ala Arg Gly Ser Ala Thr Leu Pro Glu Ile Ile
545                 550                 555                 560

Glu Ser Asn Gly Lys Lys Ala Glu Leu Tyr Thr Ser Ser Asp Ala Asn
                565                 570                 575

Asp Thr Asn Asp Val Lys Thr Ser Ile Ser Ala Ser Phe Ile Glu Asp
            580                 585                 590

Glu His Asp Ser Asn Leu Thr Ala Leu Ile Asn Leu Lys Gly Phe Ile
        595                 600                 605

Pro Ser Lys Leu Ile Lys Thr Gly Asp Tyr Tyr His Gly Arg Met Asp
    610                 615                 620

Trp Pro Ser Lys Tyr Arg Ile Ser Val Leu Ser Val Asp Tyr Asn Asp
625                 630                 635                 640

Asn Glu Glu Val Lys Ile Ile Glu Ser Ile Pro Ser Asn Lys Ile Glu
                645                 650                 655

Thr Ile Gln Val Ser Glu Ser Ile Gly Tyr Thr Val Gly Gly Glu Ile
            660                 665                 670

Ser Ala Asn Lys Glu Ser Ala Ser Gly Gly Leu Asn Ala Asn Tyr Ser
        675                 680                 685

Val Gln Arg Ser Ile Ser Tyr Glu Gln Pro Asp Phe Lys Thr Val Lys
    690                 695                 700

Lys Ser Asp Ser Thr Lys Ala Ala Ser Trp Asp Val Val Phe Asn Cys
705                 710                 715                 720

Asn Lys Asp Gly Tyr Asp Arg Asn Ser His His Pro Phe Tyr Gly Asn
                725                 730                 735
```

Gln Leu Phe Met Lys Ser Arg Leu Tyr Asn Thr Gly Ile Asn Asn Leu
740 745 750

Thr Asp Asn Lys Asp Leu Ser Thr Leu Ile Ser Gly Gly Phe Ser Pro
755 760 765

Asn Met Ala Val Ala Leu Lys Ala Pro Lys Gly Thr Lys Lys Ser Gln
770 775 780

Leu Ile Leu Ser Tyr Gln Thr Tyr His Asp Leu Tyr Lys Leu Asp Trp
785 790 795 800

Thr Gly Thr Glu Trp Trp Gly Ser Asn His Gln Ala Lys Thr Pro Thr
805 810 815

Tyr Ala Thr His Ala Tyr Glu Ile Asp Trp Glu Asn His Lys Val Thr
820 825 830

Phe Lys Tyr Leu Glu His His His His His His
835 840

<210> SEQ ID NO 7
<211> LENGTH: 2541
<212> TYPE: DNA
<213> ORGANISM: Artificial Sequence
<220> FEATURE:
<223> OTHER INFORMATION: NetF-NusA nucleotide sequence

<400> SEQUENCE: 7
atgaacaaag aaattttggc tgtagttgaa gccgtatcca atgaaaaggc gctacctcgc 60
gagaagattt tcgaagcatt ggaaagcgcg ctggcgacag caacaaagaa aaaatatgaa 120
caagagatcg acgtccgcgt acagatcgat cgcaaaagcg gtgattttga cactttccgt 180
cgctggttag ttgttgatga agtcacccag ccgaccaagg aaatcaccct tgaagccgca 240
cgttatgaag atgaaagcct gaacctgggc gattacgttg aagatcagat tgagtctgtt 300
acctttgacc gtatcactac ccagacggca aaacaggtta tcgtgcagaa agtgcgtgaa 360
gccgaacgtg cgatggtggt tgatcagttc cgtgaacacg aaggtgaaat catcaccggc 420
gtggtgaaaa aagtaaaccg cgacaacatc tctctggatc tgggcaacaa cgctgaagcc 480
gtgatcctgc gcgaagatat gctgccgcgt gaaaacttcc gccctggcga ccgcgttcgt 540
ggcgtgctct attccgttcg cccggaagcg cgtggcgcgc aactgttcgt cactcgttcc 600
aagccggaaa tgctgatcga actgttccgt attgaagtgc cagaaatcgg cgaagaagtg 660
attgaaatta aagcagcggc tcgcgatccg ggttctcgtg cgaaaatcgc ggtgaaaacc 720
aacgataaac gtatcgatcc ggtaggtgct tgcgtaggta tgcgtggcgc gcgtgttcag 780
gcggtgtcta ctgaactggg tggcgagcgt atcgatatcg tcctgtggga tgataacccg 840
gcgcagttcg tgattaacgc aatggcaccg gcagacgttg cttctatcgt ggtggatgaa 900
gataaacaca ccatggacat cgccgttgaa gccggtaatc tggcgcaggc gattggccgt 960
aacggtcaga acgtgcgtct ggcttcgcaa ctgagcggtt gggaactcaa cgtgatgacc 1020
gttgacgacc tgcaagctaa gcatcaggcg gaagcgcacg cagcgatcga caccttcacc 1080
aaatatctcg acatcgacga agacttcgcg actgttctgg tagaagaagg cttctcgacg 1140
ctggaagaat tggcctatgt gccgatgaaa gagctgttgg aaatcgaagg ccttgatgag 1200
ccgaccgttg aagcactgcg cgagcgtgct aaaaatgcac tggccaccat tgcacaggcc 1260
caggaagaaa gcctcggtga taacaaaccg gctgacgatc tgctgaacct tgaaggggta 1320
gatcgtgatt tggcattcaa actggccgcc cgtggcgttt gtacgctgga agatctcgcc 1380
gaacagggca ttgatgatct ggctgatatc gaagggttga ccgacgaaaa agccggagca 1440

-continued

```
ctgattatgg ctgcccgtaa tatttgctgg ttcggtgacg aagcgactag tggttctggt   1500

catcaccatc accatcactc cgcgggtaaa gaaaccgctg ctgcgaaatt tgaacgccag   1560

cacatggact cgccaccgcc aactggtctg gtcccccggg gcagcgcggg ttctggtacg   1620

attgatgacg acgacaagag tccgggagct cgtggatccg aattcaattc ctttcctgaa   1680

agtattatta actcaaaagg taaacaagct gaggtttata catcatcaga tgcttctgaa   1740

agagatggta taaagacatc tttatcagca tcatttattg aagatccaaa cagtaataac   1800

ttaacagctc ttgtttcttt aaaaggattt ataccttctg gattaattaa aacaggaact   1860

tattacagtg caaatatgta ttggccaagt aagtataata taaatattga aactactgat   1920

gaaaaaaata atgttaaaat tttagaaagc attccaagta atacgataga aacagtaaga   1980

gtaactgaaa gtatgggtta tagtattggt ggaaatgttt ccgttagtaa aaagtcatct   2040

tcagttggag caaatgctgg ttttaatgtt caacgttcag tacaatatga gcaacctgat   2100

ttcaagacga tacagaaatc tgatggaatt aggaaggctt cttggaacat agtgtttaac   2160

aagacaaaag atggatatga ccaaaattcg tatcatgctc tatatggcaa tcaattattt   2220

atgaaatcta ggttacataa tacaggtgca aaaaatttag ttgaagataa agatttatca   2280

ccattaattt ctggtgggtt cactcctaat atggtaattg ctcttaaggc accaaaaggc   2340

acaaaaaaat caatgattaa tttaaactat aacttatatc aagatttata tactttagag   2400

tggtataaaa cccaatggtg gggagaaaat cgtgttgcaa aagaaccata ttatacctat   2460

caaacatatg aacttgattg ggagaatcat actgtagaat ttatatacct cgagcaccac   2520

caccaccacc actaatgtta a                                            2541
```

<210> SEQ ID NO 8
<211> LENGTH: 3039
<212> TYPE: DNA
<213> ORGANISM: Artificial Sequence
<220> FEATURE:
<223> OTHER INFORMATION: NetG-NusA nucleotide sequence

<400> SEQUENCE: 8

```
atgaacaaag aaattttggc tgtagttgaa gccgtatcca atgaaaaggc gctacctcgc     60

gagaagattt tcgaagcatt ggaaagcgcg ctggcgacag caacaaagaa aaaatatgaa    120

caagagatcg acgtccgcgt acagatcgat cgcaaaagcg gtgattttga cactttccgt    180

cgctggttag ttgttgatga agtcacccag ccgaccaagg aaatcaccct tgaagccgca    240

cgttatgaag atgaaagcct gaacctgggc gattacgttg aagatcagat tgagtctgtt    300

acctttgacc gtatcactac ccagacggca aaacaggtta tcgtgcagaa agtgcgtgaa    360

gccgaacgtg cgatggtggt tgatcagttc cgtgaacacg aaggtgaaat catcaccggc    420

gtggtgaaaa aagtaaaccg cgacaacatc tctctggatc tgggcaacaa cgctgaagcc    480

gtgatcctgc gcgaagatat gctgccgcgt gaaaacttcc gccctggcga ccgcgttcgt    540

ggcgtgctct attccgttcg cccggaagcg cgtggcgcgc aactgttcgt cactcgttcc    600

aagccggaaa tgctgatcga actgttccgt attgaagtgc cagaaatcgg cgaagaagtg    660

attgaaatta aagcagcggc tcgcgatccg ggttctcgtg cgaaaatcgc ggtgaaaacc    720

aacgataaac gtatcgatcc ggtaggtgct tgcgtaggta tgcgtggcgc gcgtgttcag    780

gcggtgtcta ctgaactggg tggcgagcgt atcgatatcg tcctgtggga tgataacccg    840

gcgcagttcg tgattaacgc aatggcaccg gcagacgttg cttctatcgt ggtggatgaa    900
```

```
gataaacaca ccatggacat cgccgttgaa gccggtaatc tggcgcaggc gattggccgt    960
aacggtcaga acgtgcgtct ggcttcgcaa ctgagcggtt gggaactcaa cgtgatgacc   1020
gttgacgacc tgcaagctaa gcatcaggcg gaagcgcacg cagcgatcga caccttcacc   1080
aaatatctcg acatcgacga agacttcgcg actgttctgg tagaagaagg cttctcgacg   1140
ctggaagaat tggcctatgt gccgatgaaa gagctgttgg aaatcgaagg ccttgatgag   1200
ccgaccgttg aagcactgcg cgagcgtgct aaaaatgcac tggccaccat tgcacaggcc   1260
caggaagaaa gcctcggtga taacaaaccg gctgacgatc tgctgaacct tgaaggggta   1320
gatcgtgatt tggcattcaa actggccgcc cgtggcgttt gtacgctgga agatctcgcc   1380
gaacagggca ttgatgatct ggctgatatc gaagggttga ccgacgaaaa agccggagca   1440
ctgattatgg ctgcccgtaa tatttgctgg ttcggtgacg aagcgactag tggttctggt   1500
catcaccatc accatcactc cgcgggtaaa gaaaccgctg ctgcgaaatt tgaacgccag   1560
cacatggact cgccaccgcc aactggtctg gtcccccggg gcagcgcggg ttctggtacg   1620
attgatgacg acgacaagag tccgggagct cgtggatccg ctacgttgcc agaaattatt   1680
gaatcaaatg gtaaaaaagc agagctttat acttcttcag atgcaaatga tacgaatgat   1740
gtaaaaactt ctatatcagc atcatttatt gaagatgaac atgatagtaa tttgactgca   1800
cttattaatt taaaaggatt tattccatct aaacttataa aaacagggga ttattatcat   1860
ggaagaatgg attggccaag caaatatagg atatctgttt tgtcagtaga ttataatgat   1920
aatgaagaag taaagattat agaaagtatt ccgagtaata aaatagaaac tatacaagta   1980
agtgaaagta taggatatac tgttggtgga gaaatatcag ctaacaaaga gtcagcttct   2040
ggtggattaa atgctaacta tagtgtacaa cgttctattt cttatgaaca gccagacttt   2100
aaaacagtta aaaaatctga tagtactaaa gctgcttcat gggatgtagt ttttaattgt   2160
aataaagatg gttatgatag gaattctcat cacccatttt atggaaatca attatttatg   2220
aaatctagat tatataatac aggaattaat aatttaactg ataataaaga tttatcaaca   2280
ttaatttcag gtggattttc tcctaatatg gcagttgctc ttaaagcacc aaaaggtacg   2340
aaaaaatcac agcttatttt aagttatcaa acttatcatg atttatataa gctagattgg   2400
actggaactg aatggtgggg ttcaaatcac caagctaaaa caccaactta tgcaactcat   2460
gcttatgaaa ttgattggga gaaccataaa gtaacattta aatatctcga gcaccaccac   2520
caccaccact aatgttaatt aagttgggcg ttcctaggct gataaaacag aatttgcctg   2580
gcggcagtag cgcggtggtc ccacctgacc ccatgccgaa ctcagaagtg aaacgccgta   2640
gcgccgatgg tagtgtgggg tctccccatg cgagagtagg gaactgccag gcatcaaata   2700
aaacgaaagg ctcagtcgaa agactgggcc tttcgtttta tctgttgttt gtcggtgaac   2760
gctctcctga gtaggacaaa tccgccggga gcggatttga acgttgcgaa gcaacggccc   2820
ggagggtggc gggcaggacg cccgccataa actgccaggc atcaaattaa gcagaaggcc   2880
atcctgacgg atggcctttt tgcgtttcta caaactcttt tgtttatttt tctaaataca   2940
ttcaaatatg tatccgctga gcaataacta gcataacccc ttggggcctc taaacgggtc   3000
ttgaggggtt ttttgctgaa aggaggaact atatccgga                          3039
```

<210> SEQ ID NO 9
<211> LENGTH: 22
<212> TYPE: DNA
<213> ORGANISM: Clostridium perfringens

<400> SEQUENCE: 9
aacaatatgt acaggtataa ct 22

<210> SEQ ID NO 10
<211> LENGTH: 22
<212> TYPE: DNA
<213> ORGANISM: Clostridium perfringens

<400> SEQUENCE: 10
ttgataggta taatatggtt ct 22

<210> SEQ ID NO 11
<211> LENGTH: 22
<212> TYPE: DNA
<213> ORGANISM: Clostridium perfringens

<400> SEQUENCE: 11
ttgttcagga ttagtagcat ta 22

<210> SEQ ID NO 12
<211> LENGTH: 22
<212> TYPE: DNA
<213> ORGANISM: Clostridium perfringens

<400> SEQUENCE: 12
catgagttgc ataagttggt gt 22

<210> SEQ ID NO 13
<211> LENGTH: 22
<212> TYPE: DNA
<213> ORGANISM: Clostridium perfringens

<400> SEQUENCE: 13
aattcagtat attcacatgc ag 22

<210> SEQ ID NO 14
<211> LENGTH: 22
<212> TYPE: DNA
<213> ORGANISM: Clostridium perfringens

<400> SEQUENCE: 14
cagttatacc gattgtatta ga 22

<210> SEQ ID NO 15
<211> LENGTH: 22
<212> TYPE: DNA
<213> ORGANISM: Clostridium perfringens

<400> SEQUENCE: 15
tagaaaacgt tcaattgtat gg 22

<210> SEQ ID NO 16
<211> LENGTH: 25
<212> TYPE: DNA
<213> ORGANISM: Clostridium perfringens

<400> SEQUENCE: 16
agaaagcgct gatacagcta ataaa 25

<210> SEQ ID NO 17
<211> LENGTH: 20
<212> TYPE: DNA
<213> ORGANISM: Clostridium perfringens

<400> SEQUENCE: 17
gctaatgtta ctgccgttga                                         20

<210> SEQ ID NO 18
<211> LENGTH: 20
<212> TYPE: DNA
<213> ORGANISM: Clostridium perfringens

<400> SEQUENCE: 18
cctctgatac atcgtgtaag                                         20

<210> SEQ ID NO 19
<211> LENGTH: 22
<212> TYPE: DNA
<213> ORGANISM: Clostridium perfringens

<400> SEQUENCE: 19
attatgttta ggaatacagt ta                                      22

<210> SEQ ID NO 20
<211> LENGTH: 22
<212> TYPE: DNA
<213> ORGANISM: Clostridium perfringens

<400> SEQUENCE: 20
caataccctt caccaaatac tc                                      22

<210> SEQ ID NO 21
<211> LENGTH: 20
<212> TYPE: DNA
<213> ORGANISM: Clostridium perfringens

<400> SEQUENCE: 21
ggagatggtt ggatattagg                                         20

<210> SEQ ID NO 22
<211> LENGTH: 19
<212> TYPE: DNA
<213> ORGANISM: Clostridium perfringens

<400> SEQUENCE: 22
ggaccagcag ttgtagata                                          19

<210> SEQ ID NO 23
<211> LENGTH: 53
<212> TYPE: DNA
<213> ORGANISM: Artificial Sequence
<220> FEATURE:
<223> OTHER INFORMATION: NetE-IBS

<400> SEQUENCE: 23
aaaaaagctt ataattatcc ttaaacgtcc aactggtgcg cccagatagg gtg     53

<210> SEQ ID NO 24
<211> LENGTH: 60
<212> TYPE: DNA
<213> ORGANISM: Artificial Sequence
<220> FEATURE:
<223> OTHER INFORMATION: NetE-EBS-1d

<400> SEQUENCE: 24
cagattgtac aaatgtggtg ataacagata agtccaactg cataacttac ctttctttgt   60

<210> SEQ ID NO 25
<211> LENGTH: 49
<212> TYPE: DNA
<213> ORGANISM: Artificial Sequence
<220> FEATURE:
<223> OTHER INFORMATION: NetE-EBS-2

<400> SEQUENCE: 25
tgaacgcaag tttctaattt cggttacgtt ccgatagagg aaagtgtct 49

<210> SEQ ID NO 26
<211> LENGTH: 53
<212> TYPE: DNA
<213> ORGANISM: Artificial Sequence
<220> FEATURE:
<223> OTHER INFORMATION: NetF-IBS

<400> SEQUENCE: 26
aaaaaagctt ataattatcc ttagtcttca taccagtgcg cccagatagg gtg 53

<210> SEQ ID NO 27
<211> LENGTH: 60
<212> TYPE: DNA
<213> ORGANISM: Artificial Sequence
<220> FEATURE:
<223> OTHER INFORMATION: NetF-EBS-1d

<400> SEQUENCE: 27
cagattgtac aaatgtggtg ataacagata agtcatacca tctaacttac ctttctttgt 60

<210> SEQ ID NO 28
<211> LENGTH: 49
<212> TYPE: DNA
<213> ORGANISM: Artificial Sequence
<220> FEATURE:
<223> OTHER INFORMATION: NetF-EBS-2

<400> SEQUENCE: 28
tgaacgcaag tttctaattt cgattaagac tcgatagagg aaagtgtct 49

<210> SEQ ID NO 29
<211> LENGTH: 53
<212> TYPE: DNA
<213> ORGANISM: Artificial Sequence
<220> FEATURE:
<223> OTHER INFORMATION: NetG-IBS

<400> SEQUENCE: 29
aaaaaagctt ataattatcc ttatcctacc ataacgtgcg cccagatagg gtg 53

<210> SEQ ID NO 30
<211> LENGTH: 60
<212> TYPE: DNA
<213> ORGANISM: Artificial Sequence
<220> FEATURE:
<223> OTHER INFORMATION: NetG-EBS-1d

<400> SEQUENCE: 30
cagattgtac aaatgtggtg ataacagata agtccataac cataacttac ctttctttgt 60

<210> SEQ ID NO 31
<211> LENGTH: 49
<212> TYPE: DNA
<213> ORGANISM: Artificial Sequence
<220> FEATURE:
<223> OTHER INFORMATION: NetG-EBS-2

<400> SEQUENCE: 31
tgaacgcaag tttctaattt cggtttagga tcgatagagg aaagtgtct 49

<210> SEQ ID NO 32
<211> LENGTH: 28
<212> TYPE: DNA
<213> ORGANISM: Artificial Sequence
<220> FEATURE:
<223> OTHER INFORMATION: EBS-Universal

<400> SEQUENCE: 32
cgaaattaga aacttgcgtt cagtaaac 28

<210> SEQ ID NO 33
<211> LENGTH: 33
<212> TYPE: DNA
<213> ORGANISM: Artificial Sequence
<220> FEATURE:
<223> OTHER INFORMATION: RecNetE-F (EcoRI)

<400> SEQUENCE: 33
ccgcgaattc tctactagtt tagctcttgc aag 33

<210> SEQ ID NO 34
<211> LENGTH: 32
<212> TYPE: DNA
<213> ORGANISM: Artificial Sequence
<220> FEATURE:
<223> OTHER INFORMATION: RecNetE-R (HindIII)

<400> SEQUENCE: 34
ccgcaagctt tagaaaacgt tcaattgtat gg 32

<210> SEQ ID NO 35
<211> LENGTH: 32
<212> TYPE: DNA
<213> ORGANISM: Artificial Sequence
<220> FEATURE:
<223> OTHER INFORMATION: RecNetF-F (EcoRI)

<400> SEQUENCE: 35
ccgcgaattc aattcctttc ctgaaagtat ta 32

<210> SEQ ID NO 36
<211> LENGTH: 32
<212> TYPE: DNA
<213> ORGANISM: Artificial Sequence
<220> FEATURE:
<223> OTHER INFORMATION: RecNetF-R (XhoI)

<400> SEQUENCE: 36
ccgcctcgag gtatataaat tctacagtat ga 32

<210> SEQ ID NO 37
<211> LENGTH: 32
<212> TYPE: DNA
<213> ORGANISM: Artificial Sequence
<220> FEATURE:
<223> OTHER INFORMATION: RecNetG-F (BamHI)

<400> SEQUENCE: 37
ccgcggatcc gctacgttgc cagaaattat tg 32

<210> SEQ ID NO 38
<211> LENGTH: 32

<212> TYPE: DNA
<213> ORGANISM: Artificial Sequence
<220> FEATURE:
<223> OTHER INFORMATION: RecNetG-R (XhoI)

<400> SEQUENCE: 38
ccgcctcgag atatttaaat gttactttat gg 32

<210> SEQ ID NO 39
<211> LENGTH: 25
<212> TYPE: DNA
<213> ORGANISM: Clostridium perfringens

<400> SEQUENCE: 39
ccttcaacag atatatttcc tccaa 25

<210> SEQ ID NO 40
<211> LENGTH: 24
<212> TYPE: DNA
<213> ORGANISM: Clostridium perfringens

<400> SEQUENCE: 40
acacaaactc aagtgtttgc aagt 24

<210> SEQ ID NO 41
<211> LENGTH: 20
<212> TYPE: DNA
<213> ORGANISM: Clostridium perfringens

<400> SEQUENCE: 41
ggagatggtt ggatattagg 20

<210> SEQ ID NO 42
<211> LENGTH: 19
<212> TYPE: DNA
<213> ORGANISM: Clostridium perfringens

<400> SEQUENCE: 42
ggaccagcag ttgtagata 19

<210> SEQ ID NO 43
<211> LENGTH: 33
<212> TYPE: DNA
<213> ORGANISM: Clostridium perfringens

<400> SEQUENCE: 43
cccagtttta cacgaatttt gaccagttat gta 33

<210> SEQ ID NO 44
<211> LENGTH: 33
<212> TYPE: DNA
<213> ORGANISM: Clostridium perfringens

<400> SEQUENCE: 44
accagttatg tatatatttt gaccagtttt aca 33

<210> SEQ ID NO 45
<211> LENGTH: 34
<212> TYPE: DNA
<213> ORGANISM: Artificial Sequence
<220> FEATURE:
<223> OTHER INFORMATION: NetG
<220> FEATURE:
<221> NAME/KEY: misc_feature
<222> LOCATION: (5)..(5)

<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 45
cccanttntn catnannnnt gnccagttnt ncac 34

<210> SEQ ID NO 46
<211> LENGTH: 969
<212> TYPE: DNA
<213> ORGANISM: Clostridium perfringens

<400> SEQUENCE: 46
ttgaaaagat taaaaattat gtctactagt ttagctcttg caagtattgt tagtacaagt 60
attttttcaa cacaaactca agtgtttgca agtgaattag gcaatactaa gaaaatagag 120
ctgaaaaatc aaaatggaga aataataaaa gaagatggaa aggaagctat taaatacact 180
tctattgata cttcttcatg taaagggtta aaagcaacat taagtggaac ttttgttgaa 240
gatcaatatt ctgataagaa aactgcttta ctaaatttag atgggtttat accttcaggt 300
aagaaagtat ctggttctac atattatgga aagatgaagt ggcctgaagt ttatagaatt 360
agtatagaaa gcgctgatac agctaataaa gtaaaaatag caaattctat acctaaaaat 420
actatagata aaaaggaggt atctaattca attggatatt caattggagg aaatatatct 480
gttgaaggta aaagtggtag tgcaggaata aatgcttcat acagtgtaca aaatactata 540
agctatgaac aacctgattt tagaacaatc caaagaaaag atgaagaaaa gttagcttca 600
tgggatataa aatttgttga aactaaagat ggttataatc tggattcata tcatggtatt 660
tatgggaatc aattatttat gaaatcaaga ttatataata atggttatga aaactttact 720
gatgatagag atctctcaac tttaatttca ggtggctttt cacctaatat ggcagtagct 780
ttaacagcgc caaaagatgc taaagaatct atgataacag ttacatataa aagatttgac 840
gatgagtata ctttgaattg ggaaactact caatggaggg gatcaaataa acgttcaact 900
gcatgtgaat atactgaatt tatgtttaaa attaattggg aaaaccatac aattgaacgt 960
tttctataa 969

<210> SEQ ID NO 47
<211> LENGTH: 322

<212> TYPE: PRT
<213> ORGANISM: Clostridium perfringens

<400> SEQUENCE: 47

```
Met Lys Arg Leu Lys Ile Met Ser Thr Ser Leu Ala Leu Ala Ser Ile
1               5                   10                  15

Val Ser Thr Ser Ile Phe Ser Thr Gln Thr Gln Val Phe Ala Ser Glu
            20                  25                  30

Leu Gly Asn Thr Lys Lys Ile Glu Leu Lys Asn Gln Asn Gly Glu Ile
        35                  40                  45

Ile Lys Glu Asp Gly Lys Glu Ala Ile Lys Tyr Thr Ser Ile Asp Thr
    50                  55                  60

Ser Ser Cys Lys Gly Leu Lys Ala Thr Leu Ser Gly Thr Phe Val Glu
65                  70                  75                  80

Asp Gln Tyr Ser Asp Lys Lys Thr Ala Leu Leu Asn Leu Asp Gly Phe
                85                  90                  95

Ile Pro Ser Gly Lys Lys Val Ser Gly Ser Thr Tyr Tyr Gly Lys Met
            100                 105                 110

Lys Trp Pro Glu Val Tyr Arg Ile Ser Ile Glu Ser Ala Asp Thr Ala
        115                 120                 125

Asn Lys Val Lys Ile Ala Asn Ser Ile Pro Lys Asn Thr Ile Asp Lys
    130                 135                 140

Lys Glu Val Ser Asn Ser Ile Gly Tyr Ser Ile Gly Gly Asn Ile Ser
145                 150                 155                 160

Val Glu Gly Lys Ser Gly Ser Ala Gly Ile Asn Ala Ser Tyr Ser Val
                165                 170                 175

Gln Asn Thr Ile Ser Tyr Glu Gln Pro Asp Phe Arg Thr Ile Gln Arg
            180                 185                 190

Lys Asp Glu Glu Lys Leu Ala Ser Trp Asp Ile Lys Phe Val Glu Thr
        195                 200                 205

Lys Asp Gly Tyr Asn Leu Asp Ser Tyr His Gly Ile Tyr Gly Asn Gln
    210                 215                 220

Leu Phe Met Lys Ser Arg Leu Tyr Asn Asn Gly Tyr Glu Asn Phe Thr
225                 230                 235                 240

Asp Asp Arg Asp Leu Ser Thr Leu Ile Ser Gly Gly Phe Ser Pro Asn
                245                 250                 255

Met Ala Val Ala Leu Thr Ala Pro Lys Asp Ala Lys Glu Ser Met Ile
            260                 265                 270

Thr Val Thr Tyr Lys Arg Phe Asp Asp Glu Tyr Thr Leu Asn Trp Glu
        275                 280                 285

Thr Thr Gln Trp Arg Gly Ser Asn Lys Arg Ser Thr Ala Cys Glu Tyr
    290                 295                 300

Thr Glu Phe Met Phe Lys Ile Asn Trp Glu Asn His Thr Ile Glu Arg
305                 310                 315                 320

Phe Leu
```

<210> SEQ ID NO 48
<211> LENGTH: 2638
<212> TYPE: DNA
<213> ORGANISM: Artificial Sequence
<220> FEATURE:
<223> OTHER INFORMATION: NetE-NusA nucleotide sequence

<400> SEQUENCE: 48

```
atgaacaaag aaattttggc tgtagttgaa gccgtatcca atgaaaaggc gctacctcgc      60
```

-continued

```
gagaagattt tcgaagcatt ggaaagcgcg ctggcgacag caacaaagaa aaaatatgaa    120
caagagatcg acgtccgcgt acagatcgat cgcaaaagcg gtgattttga cactttccgt    180
cgctggttag ttgttgatga agtcacccag ccgaccaagg aaatcaccct tgaagccgca    240
cgttatgaag atgaaagcct gaacctgggc gattacgttg aagatcagat tgagtctgtt    300
acctttgacc gtatcactac ccagacggca aaacaggtta tcgtgcagaa agtgcgtgaa    360
gccgaacgtg cgatggtggt tgatcagttc cgtgaacacg aaggtgaaat catcaccggc    420
gtggtgaaaa aagtaaaccg cgacaacatc tctctggatc tgggcaacaa cgctgaagcc    480
gtgatcctgc gcgaagatat gctgccgcgt gaaaacttcc gccctggcga ccgcgttcgt    540
ggcgtgctct attccgttcg cccggaagcg cgtggcgcgc aactgttcgt cactcgttcc    600
aagccggaaa tgctgatcga actgttccgt attgaagtgc cagaaatcgg cgaagaagtg    660
attgaaatta aagcagcggc tcgcgatccg ggttctcgtg cgaaaatcgc ggtgaaaacc    720
aacgataaac gtatcgatcc ggtaggtgct tgcgtaggta tgcgtggcgc gcgtgttcag    780
gcggtgtcta ctgaactggg tggcgagcgt atcgatatcg tcctgtggga tgataacccg    840
gcgcagttcg tgattaacgc aatggcaccg gcagacgttg cttctatcgt ggtggatgaa    900
gataaacaca ccatggacat cgccgttgaa gccggtaatc tggcgcaggc gattggccgt    960
aacggtcaga acgtgcgtct ggcttcgcaa ctgagcggtt gggaactcaa cgtgatgacc   1020
gttgacgacc tgcaagctaa gcatcaggcg gaagcgcacg cagcgatcga caccttcacc   1080
aaatatctcg acatcgacga agacttcgcg actgttctgg tagaagaagg cttctcgacg   1140
ctggaagaat tggcctatgt gccgatgaaa gagctgttgg aaatcgaagg ccttgatgag   1200
ccgaccgttg aagcactgcg cgagcgtgct aaaaatgcac tggccaccat tgcacaggcc   1260
caggaagaaa gcctcggtga taacaaaccg gctgacgatc tgctgaacct tgaaggggta   1320
gatcgtgatt tggcattcaa actggccgcc cgtggcgttt gtacgctgga agatctcgcc   1380
gaacagggca ttgatgatct ggctgatatc gaagggttga ccgacgaaaa agccggagca   1440
ctgattatgg ctgcccgtaa tatttgctgg ttcggtgacg aagcgactag tggttctggt   1500
catcaccatc accatcactc cgcgggtaaa gaaaccgctg ctgcgaaatt tgaacgccag   1560
cacatggact cgccaccgcc aactggtctg gtcccccggg gcagcgcggg ttctggtacg   1620
attgatgacg acgacaagag tccgggagct cgtggatccg aattcatgtc tactagttta   1680
gctcttgcaa gtattgttag tacaagtatt ttttcaacac aaactcaagt gtttgcaagt   1740
gaattaggca atactaagaa aatagagctg aaaaatcaaa atggagaaat aataaaagaa   1800
gatggaaagg aagctattaa atacacttct attgatactt cttcatgtaa agggttaaaa   1860
gcaacattaa gtggaacttt tgttgaagat caatattctg ataagaaaac tgctttacta   1920
aatttagatg ggtttatacc ttcaggtaag aaagtatctg gttctacata ttatggaaag   1980
atgaagtggc ctgaagttta tagaattagt atagaaagcg ctgatacagc taataaagta   2040
aaaatagcaa attctatacc taaaaatact atagataaaa aggaggtatc taattcaatt   2100
ggatattcaa ttggaggaaa tatatctgtt gaaggtaaaa gtggtagtgc aggaataaat   2160
gcttcataca gtgtacaaaa tactataagc tatgaacaac ctgattttag aacaatccaa   2220
agaaaagatg aagaaaagtt agcttcatgg gatataaaat ttgttgaaac taaagatggt   2280
tataatctgg attcatatca tggtatttat gggaatcaat tatttatgaa atcaagatta   2340
tataataatg gttatgaaaa ctttactgat gatagagatc tctcaacttt aatttcaggt   2400
ggcttttcac ctaatatggc agtagcttta acagcgccaa aagatgctaa agaatctatg   2460
```

```
ataacagtta catataaaag atttgacgat gagtatactt tgaattggga aactactcaa   2520

tggaggggat caaataaacg ttcaactgca tgtgaatata ctgaatttat gtttaaaatt   2580

aattgggaaa accatacaat tgaacgtttt ctactcgagc accaccacca ccaccact     2638


<210> SEQ ID NO 49
<211> LENGTH: 878
<212> TYPE: PRT
<213> ORGANISM: Artificial Sequence
<220> FEATURE:
<223> OTHER INFORMATION: NetE-NusA  recombinant protein

<400> SEQUENCE: 49

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45

Ile Asp Arg Lys Ser Gly Asp Phe Asp Thr Phe Arg Arg Trp Leu Val
    50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
                85                  90                  95

Ile Glu Ser Val Thr Phe Asp Arg Ile Thr Thr Gln Thr Ala Lys Gln
            100                 105                 110

Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
    130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
    210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
    290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335
```

-continued

```
Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
    370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
    450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Thr
                485                 490                 495

Ser Gly Ser Gly His His His His His His Ser Ala Gly Lys Glu Thr
            500                 505                 510

Ala Ala Ala Lys Phe Glu Arg Gln His Met Asp Ser Pro Pro Pro Thr
        515                 520                 525

Gly Leu Val Pro Arg Gly Ser Ala Gly Ser Gly Thr Ile Asp Asp Asp
    530                 535                 540

Asp Lys Ser Pro Gly Ala Arg Gly Ser Glu Phe Ser Glu Leu Gly Asn
545                 550                 555                 560

Thr Lys Lys Ile Glu Leu Lys Asn Gln Asn Gly Glu Ile Ile Lys Glu
                565                 570                 575

Asp Gly Lys Glu Ala Ile Lys Tyr Thr Ser Ile Asp Thr Ser Ser Cys
            580                 585                 590

Lys Gly Leu Lys Ala Thr Leu Ser Gly Thr Phe Val Glu Asp Gln Tyr
        595                 600                 605

Ser Asp Lys Lys Thr Ala Leu Leu Asn Leu Asp Gly Phe Ile Pro Ser
    610                 615                 620

Gly Lys Lys Val Ser Gly Ser Thr Tyr Tyr Gly Lys Met Lys Trp Pro
625                 630                 635                 640

Glu Val Tyr Arg Ile Ser Ile Glu Ser Ala Asp Thr Ala Asn Lys Val
                645                 650                 655

Lys Ile Ala Asn Ser Ile Pro Lys Asn Thr Ile Asp Lys Lys Glu Val
            660                 665                 670

Ser Asn Ser Ile Gly Tyr Ser Ile Gly Gly Asn Ile Ser Val Glu Gly
        675                 680                 685

Lys Ser Gly Ser Ala Gly Ile Asn Ala Ser Tyr Ser Val Gln Asn Thr
    690                 695                 700

Ile Ser Tyr Glu Gln Pro Asp Phe Arg Thr Ile Gln Arg Lys Asp Glu
705                 710                 715                 720

Glu Lys Leu Ala Ser Trp Asp Ile Lys Phe Val Glu Thr Lys Asp Gly
                725                 730                 735

Tyr Asn Leu Asp Ser Tyr His Gly Ile Tyr Gly Asn Gln Leu Phe Met
            740                 745                 750
```

-continued

Lys Ser Arg Leu Tyr Asn Asn Gly Tyr Glu Asn Phe Thr Asp Asp Arg
755 760 765

Asp Leu Ser Thr Leu Ile Ser Gly Gly Phe Ser Pro Asn Met Ala Val
770 775 780

Ala Leu Thr Ala Pro Lys Asp Ala Lys Glu Ser Met Ile Thr Val Thr
785 790 795 800

Tyr Lys Arg Phe Asp Asp Glu Tyr Thr Leu Asn Trp Glu Thr Thr Gln
805 810 815

Trp Arg Gly Ser Asn Lys Arg Ser Thr Ala Cys Glu Tyr Thr Glu Phe
820 825 830

Met Phe Lys Ile Asn Trp Glu Asn His Thr Ile Glu Arg Phe Leu Lys
835 840 845

Leu Ala Ala Ala Gln Leu Tyr Thr Arg Ala Ser Gln Pro Glu Leu Ala
850 855 860

Pro Glu Asp Pro Glu Asp Leu Glu His His His His His His
865 870 875

<210> SEQ ID NO 50
<211> LENGTH: 312
<212> TYPE: PRT
<213> ORGANISM: Staphylococcus aureus

<400> SEQUENCE: 50

Met Val Lys Lys Arg Leu Leu Ala Ala Thr Leu Ser Leu Gly Ile Ile
1 5 10 15

Thr Pro Ile Ala Thr Ser Phe His Glu Ser Lys Ala Asp Asn Asn Ile
20 25 30

Glu Asn Ile Gly Asp Gly Ala Glu Val Val Lys Arg Thr Glu Asp Thr
35 40 45

Ser Ser Asp Lys Trp Gly Val Thr Gln Asn Ile Gln Phe Asp Phe Val
50 55 60

Lys Asp Lys Lys Tyr Asn Lys Asp Ala Leu Ile Leu Lys Met Gln Gly
65 70 75 80

Phe Ile Asn Ser Lys Thr Thr Tyr Tyr Asn Tyr Lys Asn Thr Asp His
85 90 95

Ile Lys Ala Met Arg Trp Pro Phe Gln Tyr Asn Ile Gly Leu Lys Thr
100 105 110

Asn Asp Pro Asn Val Asp Leu Ile Asn Tyr Leu Pro Lys Asn Lys Ile
115 120 125

Asp Ser Val Asn Val Ser Gln Thr Leu Gly Tyr Asn Ile Gly Gly Asn
130 135 140

Phe Asn Ser Gly Pro Ser Thr Gly Gly Asn Gly Ser Phe Asn Tyr Ser
145 150 155 160

Lys Thr Ile Ser Tyr Asn Gln Gln Asn Tyr Ile Ser Glu Val Glu Arg
165 170 175

Gln Asn Ser Lys Ser Val Gln Trp Gly Ile Lys Ala Asn Ser Phe Ile
180 185 190

Thr Ser Leu Gly Lys Met Ser Gly His Asp Pro Asn Leu Phe Val Gly
195 200 205

Tyr Lys Pro Tyr Ser Gln Asn Pro Arg Asp Tyr Phe Val Pro Asp Asn
210 215 220

Glu Leu Pro Pro Leu Val His Ser Gly Phe Asn Pro Ser Phe Ile Ala
225 230 235 240

Thr Val Ser His Glu Lys Gly Ser Gly Asp Thr Ser Glu Phe Glu Ile
245 250 255

```
Thr Tyr Gly Arg Asn Met Asp Val Thr His Ala Thr Arg Arg Thr Thr
            260                 265                 270

His Tyr Gly Asn Ser Tyr Leu Glu Gly Ser Arg Ile His Asn Ala Phe
        275                 280                 285

Val Asn Arg Asn Tyr Thr Val Lys Tyr Glu Val Asn Trp Lys Thr His
    290                 295                 300

Glu Ile Lys Val Lys Gly His Asn
305                 310


<210> SEQ ID NO 51
<211> LENGTH: 317
<212> TYPE: PRT
<213> ORGANISM: Clostridium chauvoei

<400> SEQUENCE: 51

Met Ile Lys Arg Ile Leu Met Leu Ala Leu Ala Thr Thr Thr Ile Phe
1               5                   10                  15

Ser Leu Thr Leu Pro Phe Ser Tyr Lys Ala Val Gln Ala Gln Glu Asn
            20                  25                  30

Thr Cys Ile Val Glu Thr Pro Ser Glu Gly Val Lys Thr Phe Thr Ser
        35                  40                  45

Ser Asp Thr Ala Tyr Ala Asp Tyr Asn Cys Phe Lys Thr Asn Leu Ser
    50                  55                  60

Val Thr Phe Ile Glu Asp Gln His Asn Asn Gln Leu Thr Ala Leu Val
65                  70                  75                  80

Ser Thr Glu Gly Ser Phe Ile Pro Ser Gly Leu Ser Arg Val Gly Gly
                85                  90                  95

Tyr Tyr Gln Ala Asp Met Tyr Trp Pro Ser Lys Tyr Tyr Thr Thr Leu
            100                 105                 110

Thr Thr Tyr Asp Arg Asn Asn Arg Val Lys Ile Thr Lys Ser Ile Pro
        115                 120                 125

Thr Asn Gln Ile Asp Thr Val Ser Val Ser Glu Thr Met Gly Tyr Ser
    130                 135                 140

Ile Gly Gly Ser Leu Ser Ile Glu Tyr Gly Lys Glu Gly Pro Lys Ala
145                 150                 155                 160

Gly Gly Gly Ile Asn Gly Ser Tyr Thr Ala Gln Arg Ser Val Thr Tyr
                165                 170                 175

Asp Gln Pro Asp Tyr Arg Thr Leu Leu Met Lys Asp Ser Val Asn Ser
            180                 185                 190

Ala Ser Trp Glu Val Ala Phe Asn Ala Thr Lys Asp Gly Tyr Asp Arg
        195                 200                 205

Asp Ser Tyr His Gly Ile Tyr Gly Asn Gln Leu Phe Met Arg Tyr Arg
    210                 215                 220

Leu Tyr Asn Thr Gly Ile Asn Asn Leu Thr Thr Asp Asn Asn Leu Ser
225                 230                 235                 240

Ser Leu Ile Val Gly Gly Phe Ser Pro Lys Val Val Ile Ala Leu Thr
                245                 250                 255

Ala Pro Lys Gly Thr Glu Glu Ser Thr Val Lys Val Glu Tyr Asn Arg
            260                 265                 270

Phe Asn Asp Gln Tyr Arg Leu Arg Trp Ser Gly Thr Glu Trp Tyr Gly
        275                 280                 285

Glu Asn Asn Arg Asn Ser Arg Ile Asp Ser Ser Ser Glu Ser Phe Ile
    290                 295                 300

Leu Asn Trp Lys Asn His Thr Val Glu His Ala Gly Tyr
```

```
305                 310                 315


<210> SEQ ID NO 52
<211> LENGTH: 312
<212> TYPE: PRT
<213> ORGANISM: Clostridium botulinum

<400> SEQUENCE: 52

Met Leu Lys Leu Lys Lys Ile Asn Ser Leu Ile Leu Ser Ser Val Leu
1               5                   10                  15

Leu Leu Gly Met Ser Ile Asn Phe Ser Ser Ile Gln Ala Asn Ala Ile
            20                  25                  30

Glu Ser Thr Asp His Val Lys Thr Tyr Thr Ser Thr Asp Val Thr Asp
        35                  40                  45

Asn Asn Tyr Asn His Phe Lys Thr Thr Leu Ser Val Thr Phe Ile Glu
    50                  55                  60

Asp Asp Phe Asp Asn Gln Leu Thr Ala Leu Val Ser Thr Glu Gly Ser
65                  70                  75                  80

Phe Ile Pro Ser Gly Leu Thr Arg Leu Thr Gly Ser Tyr Tyr Ala Asp
                85                  90                  95

Met Tyr Trp Pro Ser Thr Tyr Arg Thr Ile Ile Lys Ser Gln Asp Lys
            100                 105                 110

Asn Asn Ser Ile Lys Ile Ala Lys Ser Ile Pro Ser Asn Gln Ile Lys
        115                 120                 125

Thr Ser Arg Val Ser Glu Thr Met Gly Tyr Ser Ile Gly Gly Asn Ile
    130                 135                 140

Ser Val Glu Gly Asn Lys Asp Gly Gly Lys Ala Ser Gly Gly Val Ser
145                 150                 155                 160

Gly Ser Tyr Asn Ala Ser Arg Ser Val Ser Tyr Asp Gln Pro Glu Tyr
                165                 170                 175

Asn Thr Leu Leu Lys Lys Asp Ser Lys Thr Ala Ala Glu Trp Gln Val
            180                 185                 190

Ser Tyr Asn Glu Asn Lys Asp Gly Tyr Asn Arg Asn Ser Ser His Gly
        195                 200                 205

Ile Tyr Gly Asn Gln Leu Phe Met Lys Ser Arg Leu Gly Asn Trp Gly
    210                 215                 220

Thr Thr Asn Leu Thr Asp Leu Asn Asp Leu Ser Ser Leu Ile Thr Gly
225                 230                 235                 240

Gly Phe Ser Pro Lys Val Val Val Ala Leu Lys Ala Pro Lys Gly Thr
                245                 250                 255

Lys Thr Ser Gly Ile Thr Val Asp Tyr Thr Arg Phe Asn Asp Lys Tyr
            260                 265                 270

Ser Leu Lys Trp Asp Gly Ala Glu Trp Val Gly Gln Asn Asn Asp Ser
        275                 280                 285

Val Ser Leu Ala Asn Thr Glu Ser Thr Phe Leu Leu Asp Trp Glu Asn
    290                 295                 300

His Thr Val Lys Ser Leu Tyr Asn
305                 310


<210> SEQ ID NO 53
<211> LENGTH: 322
<212> TYPE: PRT
<213> ORGANISM: Clostridium perfringens

<400> SEQUENCE: 53

Met Lys Arg Leu Lys Ile Ile Ser Ile Thr Leu Val Leu Thr Ser Val
```

-continued

```
1               5                   10                  15

Ile Ser Thr Ser Leu Phe Ser Thr Gln Thr Gln Val Phe Ala Ser Glu
            20                  25                  30

Leu Asn Asp Ile Asn Lys Ile Glu Leu Lys Asn Leu Ser Gly Glu Ile
        35                  40                  45

Ile Lys Glu Asn Gly Lys Glu Ala Ile Lys Tyr Thr Ser Ser Asp Thr
    50                  55                  60

Ala Ser His Lys Gly Trp Lys Ala Thr Leu Ser Gly Thr Phe Ile Glu
65                  70                  75                  80

Asp Pro His Ser Asp Lys Lys Thr Ala Leu Leu Asn Leu Glu Gly Phe
                85                  90                  95

Ile Pro Ser Asp Lys Gln Ile Phe Gly Ser Lys Tyr Tyr Gly Lys Met
            100                 105                 110

Lys Trp Pro Glu Thr Tyr Arg Ile Asn Val Lys Ser Ala Asp Val Asn
        115                 120                 125

Asn Asn Ile Lys Ile Ala Asn Ser Ile Pro Lys Asn Thr Ile Asp Lys
    130                 135                 140

Lys Asp Val Ser Asn Ser Ile Gly Tyr Ser Ile Gly Gly Asn Ile Ser
145                 150                 155                 160

Val Glu Gly Lys Thr Ala Gly Ala Gly Ile Asn Ala Ser Tyr Asn Val
                165                 170                 175

Gln Asn Thr Ile Ser Tyr Glu Gln Pro Asp Phe Arg Thr Ile Gln Arg
            180                 185                 190

Lys Asp Asp Ala Asn Leu Ala Ser Trp Asp Ile Lys Phe Val Glu Thr
        195                 200                 205

Lys Asp Gly Tyr Asn Ile Asp Ser Tyr His Ala Ile Tyr Gly Asn Gln
    210                 215                 220

Leu Phe Met Lys Ser Arg Leu Tyr Asn Asn Gly Asp Lys Asn Phe Thr
225                 230                 235                 240

Asp Asp Arg Asp Leu Ser Thr Leu Ile Ser Gly Gly Phe Ser Pro Asn
                245                 250                 255

Met Ala Leu Ala Leu Thr Ala Pro Lys Asn Ala Lys Glu Ser Val Ile
            260                 265                 270

Ile Val Glu Tyr Gln Arg Phe Asp Asn Asp Tyr Ile Leu Asn Trp Glu
        275                 280                 285

Thr Thr Gln Trp Arg Gly Thr Asn Lys Leu Ser Ser Thr Ser Glu Tyr
    290                 295                 300

Asn Glu Phe Met Phe Lys Ile Asn Trp Gln Asp His Lys Ile Glu Tyr
305                 310                 315                 320

Tyr Leu
```

<210> SEQ ID NO 54
<211> LENGTH: 318
<212> TYPE: PRT
<213> ORGANISM: Clostridium perfringens

<400> SEQUENCE: 54

```
Met Asn Ser Lys Lys Ile Ile Thr Thr Ile Leu Leu Ser Ser Met Val
1               5                   10                  15

Ile Ala Asn Leu Gly Leu Ala Gln Pro Val Leu Ala Asn Asp Leu Gly
            20                  25                  30

Ser Lys Ser Glu Ile Arg Lys Glu Glu Asn Gly Asn Val Thr Ile Ile
        35                  40                  45

Thr Gln Asn Asn Lys Gln Ile Arg Lys Tyr Ser Ser Thr Asp Ser Ala
```

```
    50                  55                  60

Thr Thr Lys Ser Asn Ser Lys Ile Thr Val Asp Ala Ser Phe Val Asp
65                  70                  75                  80

Asp Lys Phe Ser Ser Glu Met Thr Thr Ile Ile Ser Leu Lys Gly Phe
                85                  90                  95

Ile Pro Ser Gly Arg Lys Ile Phe Ala Leu Ser Lys Tyr Arg Gly Val
            100                 105                 110

Met Arg Trp Pro Ile Lys Tyr Met Val Asp Leu Lys Asn Asn Ser Leu
        115                 120                 125

Asp Ser Ser Val Lys Ile Val Asp Ser Val Pro Lys Asn Thr Ile Ser
    130                 135                 140

Thr Lys Glu Val Asn Asn Thr Ile Ser Tyr Ser Ile Gly Gly Gly Ile
145                 150                 155                 160

Asp Thr Ser Asn Lys Ala Ser Leu Asn Ala Asn Tyr Ala Val Ser Lys
                165                 170                 175

Ser Ile Ser Tyr Val Gln Pro Asp Tyr Asn Thr Ile Gln Thr Asn Asp
            180                 185                 190

Thr Asn Ser Ile Ala Ser Trp Asn Thr Glu Phe Ala Glu Thr Arg Asp
        195                 200                 205

Gly Tyr Asn Val Asn Ser Trp Asn Ile Val Tyr Gly Asn Gln Met Phe
    210                 215                 220

Met Arg Ser Arg Tyr Ser Gly Thr Ser Thr Thr Asn Phe Thr Pro Asp
225                 230                 235                 240

Tyr Gln Leu Ser Ser Leu Ile Thr Gly Gly Phe Ser Pro Asn Phe Gly
                245                 250                 255

Val Val Leu Thr Ala Pro Asn Gly Thr Lys Lys Ser Gln Ile Glu Ile
            260                 265                 270

Ser Leu Lys Arg Glu Ile Asn Ser Tyr His Ile Ala Trp Asp Thr Glu
        275                 280                 285

Trp Gln Gly Arg Asn Tyr Pro Asp Ser Lys Ile Glu Glu Thr Val Lys
    290                 295                 300

Phe Glu Leu Asp Trp Glu Lys His Thr Ile Arg Gln Ile Ser
305                 310                 315


<210> SEQ ID NO 55
<211> LENGTH: 336
<212> TYPE: PRT
<213> ORGANISM: Clostridium perfringens

<400> SEQUENCE: 55

Met Lys Lys Lys Phe Ile Ser Leu Val Ile Val Ser Ser Leu Leu Asn
1               5                   10                  15

Gly Cys Leu Leu Ser Pro Thr Leu Val Tyr Ala Asn Asp Ile Gly Lys
            20                  25                  30

Thr Thr Thr Ile Thr Arg Asn Lys Thr Ser Asp Gly Tyr Thr Ile Ile
        35                  40                  45

Thr Gln Asn Asp Lys Gln Ile Ile Ser Tyr Gln Ser Val Asp Ser Ser
    50                  55                  60

Ser Lys Asn Glu Asp Gly Phe Thr Ala Ser Ile Asp Ala Arg Phe Ile
65                  70                  75                  80

Asp Asp Lys Tyr Ser Ser Glu Met Thr Thr Leu Ile Asn Leu Thr Gly
                85                  90                  95

Phe Met Ser Ser Lys Lys Glu Asp Val Ile Lys Lys Tyr Asn Leu His
            100                 105                 110
```

-continued

```
Asp Val Thr Asn Ser Thr Ala Ile Asn Phe Pro Val Arg Tyr Ser Ile
        115                 120                 125

Ser Ile Leu Asn Glu Ser Ile Asn Glu Asn Val Lys Ile Val Asp Ser
    130                 135                 140

Ile Pro Lys Asn Thr Ile Ser Gln Lys Thr Val Ser Asn Thr Met Gly
145                 150                 155                 160

Tyr Lys Ile Gly Gly Ser Ile Glu Ile Glu Lys Asn Lys Pro Lys Ala
                165                 170                 175

Ser Ile Glu Ser Glu Tyr Ala Glu Ser Ser Thr Ile Glu Tyr Val Gln
            180                 185                 190

Pro Asp Phe Ser Thr Ile Gln Thr Asp His Ser Thr Ser Lys Ala Ser
        195                 200                 205

Trp Asp Thr Lys Phe Thr Glu Thr Thr Arg Gly Asn Tyr Asn Leu Lys
    210                 215                 220

Ser Asn Asn Pro Val Tyr Gly Asn Glu Met Phe Met Tyr Gly Arg Tyr
225                 230                 235                 240

Thr Asn Val Pro Ala Thr Glu Asn Ile Ile Pro Asp Tyr Gln Met Ser
                245                 250                 255

Lys Leu Ile Thr Gly Gly Leu Asn Pro Asn Met Ser Val Val Leu Thr
            260                 265                 270

Ala Pro Asn Gly Thr Glu Glu Ser Ile Ile Lys Val Lys Met Glu Arg
        275                 280                 285

Glu Arg Asn Cys Tyr Tyr Leu Asn Trp Asn Gly Ala Asn Trp Val Gly
    290                 295                 300

Gln Val Tyr Ser Arg Leu Ala Phe Asp Thr Pro Asn Val Asp Ser His
305                 310                 315                 320

Ile Phe Thr Phe Lys Ile Asn Trp Leu Thr His Lys Val Thr Ala Ile
                325                 330                 335
```